US008242090B2

(12) United States Patent
Khachigian

(10) Patent No.: US 8,242,090 B2
(45) Date of Patent: Aug. 14, 2012

(54) VASCULAR THERAPEUTICS

(75) Inventor: Levon M. Khachigian, Ryde (AU)

(73) Assignee: Newsouth Innovations PTY Limited, Sydney NSW (AU)

( * ) Notice: Subject to any disclaimer, the term of this patent is extended or adjusted under 35 U.S.C. 154(b) by 0 days.

(21) Appl. No.: 10/923,197

(22) Filed: Aug. 20, 2004

(65) Prior Publication Data

US 2005/0119213 A1 Jun. 2, 2005

Related U.S. Application Data

(63) Continuation of application No. PCT/AU03/00237, filed on Feb. 27, 2003.

(30) Foreign Application Priority Data

Feb. 27, 2002 (AU) ........................................ PS0780

(51) Int. Cl.
*C12N 15/11* (2006.01)
*C07H 21/04* (2006.01)
*C12Q 1/68* (2006.01)

(52) U.S. Cl. ........................ 514/44 A; 536/24.5; 435/6.1
(58) Field of Classification Search .................... 514/44; 435/6, 4, 325, 375
See application file for complete search history.

(56) References Cited

U.S. PATENT DOCUMENTS

| | | | |
|---|---|---|---|
| 5,837,244 A | | 11/1998 | Karin et al. |
| 5,985,558 A | * | 11/1999 | Dean et al. ......................... 435/6 |
| 7,034,009 B2 | * | 4/2006 | Pavco et al. ..................... 514/44 |
| 2002/0037866 A1 | * | 3/2002 | Schlingensiepen et al. .... 514/44 |
| 2002/0165158 A1 | | 11/2002 | King |
| 2004/0121457 A1 | | 6/2004 | Castellon |
| 2005/0222065 A1 | | 10/2005 | Khachigian |

FOREIGN PATENT DOCUMENTS

| | | |
|---|---|---|
| WO | WO 95/02051 | 1/1995 |
| WO | WO-98/33904 A2 | 8/1998 |
| WO | WO-98/33904 A3 | 8/1998 |
| WO | WO 9833904 A2 * | 8/1998 |
| WO | WO 98/46272 | 10/1998 |
| WO | WO 01/32156 A2 | 5/2001 |
| WO | WO 01/32156 A3 | 5/2001 |

OTHER PUBLICATIONS

Kipshidze et al., Antisense therapy for restenosis following percutaneous coronary intervention., 2005, Expert Opin.Biol.Ther. vol. 5, pp. 79-89.*
O'Brien et al., Gene Therapy for atherosclerotic cardiovascular disease: A time for optimism and caution, 2000, Mayo Clin Proc. vol. 75, pp. 831-834.*
Scherer et al., Approaches for the sequence-specific knockdown of mRNA, Dec. 2003, Nature Biotechnology, vol. 21, pp. 1457-1465.*
Definition of "prevent", Merriam-Webster Online Dictionary.*
Opalinska et al., Nucleic-acid therapeutics: Basic principles and recent applications, Jul. 2002, Nature Reviews Drug Discovery, vol. 1, pp. 503-514.*
Patil et al., DNA-based therapeutics and DNA delivery systems: A comprehensive review, 2005, The AAPS Journal, vol. 7, pp. E61-E77.*
Charlie Schmidt, Negotiating the RNAi patent thicket, Mar. 2007, Nature Biotechnology, vol. 25, pp. 273-275.*
Wang et al., Adnovirus-mediated overexpression of c-Jun and c-Fos induces intercellular adhesion molecule-1 and monocyte chemoattractant protein-1 in human endothelial cells, 1999, Arteriosclerosis, Thrombosis, and Vascular Biology, vol. 19, pp. 2078-2084.*
Sun et al., Catalytic nucleic acids: from lab to applications, 2000, Pharmacological Reviews; vol. 52, pp. 325-347.*
Stanley T. Crooke, Vitravene TM—another piece in the mosaic, 1998, Antisense & Nucleic Acid Drug Development, vol. 8, pp. vii-viii.*
European Approval of Vitravene Triggers $2.5 MM Milestone for Isis, PR Newswire, New York, Aug. 4, 1999, pp. 1 and 2 of print version from ProQuest are enclosed.*
Alfranca et al., c-Jun and Hypoxia-inducible factor 1 funcitonally cooperate in hypoxia-induced gene transcription, Jan. 2002, Molecular and Cellular Biology, vol. 22, pp. 12-22.*
Casey et al., Perspective: Factors controlling ocular angiogenesis, 1997, American Journal of Ophthalmology, vol. 124, pp. 521-529.*
Peter A. Campochiaro, Retinal and choroidal neovascularization, 2000, Journal of Cellular Physiology, vol. 184, pp. 301-310.*
Kraemer et al., Rat embryo fibroblasts transformed by c-Jun display highly metastatic and angiogenic activities in vivo and deregulate gene expression of both angiogenic and antiangiogenic factors, Mar. 1999, Cell Growth & Differentiation, vol. 10, pp. 193-200.*
Laniado-Schwartzman et al., Activation of nuclear factor kB and oncogene expression by 12(R)-hydroxyeicosatrienoic acid, an angiogenic factor in microvessel endothelial cells, 1994. The Journal of Biolotical Chemistry, vol. 269, pp. 24321-24327.*
Levon M. Khachigian, Catalytic DNAs as potential therapeutic agents and sequence-specific molecular tools to dissect biological function, 2000, The Journal of Clinical Investigation, vol. 106, pp. 1189-1195.*
Otani et al., ANgiotensin II-stimulated vascular endothelial growth factor expression in bovine reitnal pericytes, 2000, Investigative Ophthalmology & Visual Science, vol. 41, pp. 1192-1199.*
Roy et al., Reduction of fibronectin expression by intravitreal administration of antisense oligonucleotides, 1999, Nature Biotechnology, vol. 17, pp. 476-479.*
Ren et al., mRNA expression of proto-oncogenes and platelet-derived growth factor in proliferative vitreoretianl diseases, 2000, Japanese Journal of Ophthalmology, vol. 44, pp. 308-311.*
Wang et al., Adenovirus-mediated overexpression of c-Jun and c-Fos induces intercellular adhesion molecule-1 and monocyte chemoattractant protein-1 in human endothelial cells, 1999, Arteriosclerosis, Thrombosis, and Vascular Biology, vol. 19, pp. 2078-2084.*
Mercola, Dan et al. (1995). "Antisense Approaches to Cancer Gene Therapy," *Cancer Gene Therapy* 2(1): 47-59.

(Continued)

*Primary Examiner* — Dana Shin
(74) *Attorney, Agent, or Firm* — Morrison & Foerster LLP

(57) ABSTRACT

The present invention provides a method of preventing or reducing restenosis, neointima formation, graft failure, atherosclerosis, angiogenesis and/or solid tumor growth in a subject The method comprises administering to the subject a prophylactically effective dose of a nucleic acid which decreases the level of c-Jun mRNA, c-Jun mRNA translation or nuclear accumulation or activity of c-Jun. It is preferred that the nucleic acid is a DNAzyme that targets c-Jun mRNA.

2 Claims, 30 Drawing Sheets

OTHER PUBLICATIONS

Khachigian, Levon M. et al. (Jun. 21, 2002): "c-Jun Regulates Vascular Smooth Muscle Cell Growth and Neointima Formation after Arterial Injury," *J. Biol. Chem.* 277(25): 22985-22991.

International Search Report mailed on Jun. 19, 2003, for PCT patent application No. PCT/AU03/00237 filed on Feb. 27, 2003, 4 pages.

Adamis, A. P. et al. (1999). "Angiogenesis and ophthalmic disease," *Angiogenesis* 3:9-14.

Bhushan, M. et al. (2002). "Recent advances in cutaneous angiogenesis," *British Journal of Dermatology* 147:418-425.

Dichtl, W. et al. (2003). "HMG-CoA Reductase Inhibitors Regulate Inflammatory Transcription Factors in Human Endothelial and Vascular Smooth Muscle Cells," *Arteriosclerosis, Thrombosis and Vascular Biology* 23:58-63.

Ferrara, N. et al. (Jun. 2003). "The biology of VEGF and its receptors," *Nature Medicine* 9(6):669-676.

Ito, Y. et al. (Oct. 15, 2003). "Inhibition of Angiogenesis and Vascular Leakiness by Angiopoietin-Related Protein 4," *Cancer Research* 63:6651-6657.

Janssen, Y. et al. (1997). "Differential induction of *c-fos, c-jun*, and apoptosis in lung epithelial cells exposed to ROS or RNS," *American Journal of Physiology: Lung Cellular and Molecular Physiology* 273: L789-L796.

Krzystolik, M. et al. (Mar. 2002). "Prevention of Experimental Choroidal Neovascularization With Intravitreal Anti-Vascular Endothelial Growth Factor Antibody Fragment," *Archives of Ophthalmology* 120(3):338-346.

Leenders, W. et al. (2002). "Design of a Variant of Vascular Endothelial Growth Factor-A (VEGF-A) Antagonizing KDR/Flk-1 and Flt-1," *Laboratory Investigation* 82(4):473-481.

Maldve, R. et al. (1995). "Tumor-Promoting Activity of 2,4-dinitrofluorobenzene," *International Journal of Cancer* 60:545-553.

Momiyama, N. et al. (Aug. 1996). "Suppression of *c-jun* by Antisense Oligonucleotides Inhibits Cell Adhesion but not Respiratory Burst during Phobol Ester-induced Differentiation of U937 Human Monoblastic Cells," *Cell Growth & Differentiation* 7:1005-1012.

Nakamura, H. et al. (2002). "Introduction of DNA enzyme for Egr-1 into tubulointerstitial fibroblasts by electroporation reduced interstitial α-smooth muscle actin expression and fibrosis in unilateral ureteral obstruction (UUO) Rats," *Gene Therapy* 9:495-502.

Ross, R. (1999). "Atherosclerosis-An Inflammatory Disease," *New England Journal of Medicine* 340(2):115-126.

van Nieuw Amerongen, G. P. et al. (2003). "Targets for pharmacological intervention of endothelial hyperpermeability and barrier function," *Vascular Pharmacology* 39:257-272.

Wang, N. et al. (2001). "Adenovirus-Mediated Overexpression of Dominant-Negative Mutant of c-Jun Prevents Intercellular Adhesion Molecule-1 Induction by LDL," *Arteriosclerosis, Thrombosis and Vascular Biology* 21:1414-1420.

Yamada, M. et al. (2003). "Molecular Mechanism and Role of Endothelial Monocyte Chemoattractant Protein-1 Induction by Vascular Endothelial Growth Factor," *Arteriosclerosis, Thrombosis and Vascular Biology* 23:1996-2001.

Zhang, G. et al. (May 5, 2004). "Effect of Deoxyribozymes Targeting c-Jun on Solid Tumor Growth and Angiogenesis in Rodents," *Journal of the National Cancer Institute* 96(9):683-696.

Lu, P.Y. et al. (2005). "In Vivo Application of RNA Interference: From Functional Genomics to Therapeutics," *Advances in Genetics* 54:117-142.

Tuschl, T. et al. (Jun. 2002). "Small Interfering RNAs: A Revolutionary Tool for the Analysis of Gene Function and Gene Therapy," *Molecular Interventions* 2:158-167.

Fichou et al. (2006). "The Potential of Oligonucleotides for Therapeutic Applications," *TRENDS in Biotechnology* 24:563-570.

Sioud, M. (2005). "siRNA Delivery in Vivo," *Methods in Molecular Biology* 309:237-249.

Stephenson et al. (Jan. 1978). "Inhibition of Rouse Sarcoma Viral RNA Translation by a Specific Oligodeoxyribonucleotide," *PNAS* 75:285-288.

Edwards, D.R. et al. (Nov. 15, 1992). "Involvement of AP1 and PEA3 Binding Sites in the Regulation of Murine Tissue Inhibitor of Metalloproteinases-1 (TIMP-1) Transcription," *Biochimica et Biophysica Acta* 1171(1):41-55.

Edwards, D.R. et al. (Nov. 15, 1992). "Involvement of AP1 and PEA3 Binding Sites in the Regulation of Murine Tissue Inhibitor of Metalloproteinases-1 (TIMP-1) Transcription," *Biochimica et Biophysica Acta* 1171(1):41-55. (Abstract Only—2 pages).

Final Office Action mailed Mar. 28, 2007, for U.S. Appl. No. 10/950,013, 18 pages.

Folkman, J. (May 5, 2004). "Angiogenesis and c-Jun," *Journal of the National Cancer Institute* 96(9):644.

Ikenaka, Y. et al. (2003). "Tissue Inhibitor of Metalloproteinases-1 (TIMP-1) Inhibits Tumor Growth and Angiogenesis in the TIMP-1 Transgenic Mouse Model," *Int. J. Cancer* 105:340-346.

Non-Final Office Action mailed Aug. 25, 2006, for U.S. Appl. No. 10/950,013, 11 pages.

Non-Final Office Action mailed Jun. 22, 2007, for U.S. Appl. No. 10/950,013, nine pages.

Pal, S. et al. (Oct. 9, 1998). "Activation of Sp1-Mediated Vascular Permeability Factor/Vascular Endothelial Growth Factor Transcription Requires Specific Interaction with Protein Kinase C $\zeta$," The Journal of Biological Chemistry 273(41):26277-26280.

Pal, S. et al. (Jan. 26, 2001). "Role of Protein Kinase C$\zeta$ in Ras-Mediated Transcriptional Activation of Vascular Permeability Factor/Vascular Endothelial Growth Factor Expression," *The Journal of Biological Chemistry* 276(4):2395-2403.

PRNewswire. (May 5, 2003). "Studies Demonstrate Potential Clinical Utility if siRNA in Ophthalmic Disease," pp. 1 and 2 of print.

Reynolds, A. et al. (Mar. 2004). "Rational siRNA Design for RNA Interference," *Nature Biotechnology* 22:326-330.

Blei, F. et al. (Jun. 1993). "Mechanism of Action of Angiostatic Steroids: Suppression of Plasminogen Activator Activity via Stimulation of Plasminogen Activator Inhibitor Synthesis," *J. Cell Physiol.* 155(3):568-578, Abstract Only.

Chlenski, A. et al. (Dec. 15, 2002). "SPARC Is a Key Schwannian-derived Inhibitor Controlling Neuroblastoma Tumor Angiogenesis," *Cancer Research* 62:7357-7363.

Dibbens, J.A. et al. (Apr. 1999). "Hypoxic Regulation of Vascular Endothelial Growth Factor mRNA Stability Requires the Cooperation of Multiple RNA Elements," *Molecular Biology of the Cell* 10:907-919.

Final Office Action mailed Jan. 24, 2008, for U.S. Appl. No. 10/950,013, filed Sep. 23, 2004, 6 pages.

Martin, D.C. et al. (Aug. 1, 1996). "Inhibition of SV40 T Antigen-induced Hepatocellular Carcinoma in TIMP-1 Transgenic Mice," *Oncogene* 13(3):569-576, Abstract Only.

Rinehart-Kim, J. et al. (2000). "Alterations in the Gene Expression Profile of MCF-7 Breast Tumor Cells in Response to c-Jun," *Int. J. Cancer* 88:180-190.

Wang, N. et al. (Sep. 3, 1999). "c-Jun Triggers Apoptosis in Human Vascular Endothelial Cells," *Circ. Res.* 85:387-393.

Yoshida, S. et al. (Jul. 1997). "Involvement of Interleukin-8, Vascular Endothelial Growth Factor, and Basic Fibroblast Growth Factor in Tumor Necrosis Factor Alpha-Dependent Angiogenesis," *Molecular and Cellular Biology* 17(7):4015-4023.

Elbashir et al. (2002). "Analysis of Gene Function in Somatic Mammalian Cells Using Small Interfering RNAs," *Methods* 26:199-213.

Biswals, S. et al. (Feb. 2002). "Inhibition of Cell Proliferation and AP-1 Activity by Acrolein in Human A549 Lung Adenocarcinoma Cells Due to Thiol Imbalance and Covalent Modifications," *Chemical Research in Toxicology* 15(2):180-186.

Buschwald, A.B. et al. (Feb. 20, 2002). "Decoy Oligodeoxynucleotide Against Activator Protein-1 Reduces Neointimal Proliferation After Coronary Angioplasty in Hypercholesterolemic Minipigs," *Journal of the American College of Cardiology* 39(4):732-738.

Carmeliet, P. et al. (Nov. 2001). "Growing Better Blood Vessels, A Polymer Scaffold that Delivers Two Angiogenic Factors with Distinct Kinetics Shows Promise for Engineering Mature Blood Vessels," *Nature Biotechnology* 19:1019-1020.

European Search Report mailed on Nov. 19, 2009, for EP Patent Application No. 03 702 205.0, 13 pages.

Garrett, K.L. et al. (2001, e-pub. Jul. 3, 2001). "in vivo use of Oligonucleotides to Inhibit Choroidal Neovasularisation in the Eye," *The Journal of Gene Medicine* 3:373-383.

Kurz, H. (2000). "Physiology of Angiogenesis," *Journal of Neuro-Oncoology* 50:17-35.

Non-Final Office Action mailed Aug. 28, 2009, for U.S. Appl. No. 10/950,013, filed Sep. 23, 2004, 21 pages.

Pan, B. et al. (May 1, 2002). "Reversal of Cisplatin Resistance in Human Ovarian Cancer Cell Lines by a *c-jun* Antisense Oligodoexynucleotide (ISIS 10582): Evidence for the Role of Transcription Factor Overexpression in Determining Resistant Phenotype," *Biochemical Pharmacology* 63(9):1699-1707.

Suggs, W.D. et al. (Aug. 1999). "Antisense Oligonucleotides to *c-fos* and *c-jun* Inhibit Intimal Thickening in a Rat Vein Graft Model," *Surgery* 126(2):443-449.

Yamashita, S. et al. (1996). "Temporal and Cell-Type Specific Expression of *c-fos* and *c-jun* Protooncogenes in the Mouse Uterus After Estrogen Stimulation," *Endocrinology* 137(12):5468-5475.

Ahmad, M. et al. (Feb. 20, 1998). "Role of Activating Protein-1 in the Regulation of the Vascular Cell Adhesion Molecule-1 Gene Expression by Tumor Necrosis Factor-α," *The Journal of Biological Chemistry* 278(8):4616-4621.

Bhindi, R. et al. (Oct. 2007). "DNA Enzymes, Short Interfering RNA, and the Emerging Wave of Small-Molecule Nucleic Acid-Based Gene-Silencing Strategies," *The American Journal of Pathology* 17(4):1079-1088.

Bolon, B. et al. (2004). "Osteoclast Numbers in Lewis Rats with Adjuvant-Induced Arthritis: Identification of Preferred Sites and Parameters for Rapid Quantitative Analysis," *Veterinary Pathology*, as posted on www.vet.sagepub.com/content/41/1/30 <http://www.vet.sagepub.com/content/41/1/30>, last visited on May 25, 2010, 41(1):30-36.

Dass, C.R. et al. (2002). "Cellular Uptake, Distribution, and Stability of 10-23 Deoxyribozymes," *Antisense and Nucleic Acid Drug Development* 12:289-299.

De Fougerolles, A.R. et al. (Mar. 2000). "Regulation of Inflammation by Collagen-Binding Integrins α1β1 and α2β1 in Models of Hypersensitivity and Arthritis," *The Journal of Clinical Investigation* 105(6):721-729.

Engelhardt, B. et al. (2004). "Transendothelial Migration of Leukocytes: Through the Front Door or Around the Side of the House?" *Eur. J. Immunol.* 34:2955-2963.

Fahmy, R.G. et al. (Aug. 2003). "Transcription Factor Erg-1 Supports FGF-Dependent Angiogenesis During Neovascularization and Tumor Growth," *Nature Medicine* 9(8):1026-1032.

Fahmy, R.G. et al. (Jul. 2006, e-pub. Jul. 2, 2006). "Suppression of Vascular Permeability and Inflammation by Targeting of the Transcription Factor c-Jun," *Nature Biotechnology* 24(7):856-863.

Final Office Action mailed May 4, 2010, for U.S. Appl. No. 10/950,013, filed Sep. 23, 2004, 23 pages.

Final Office Action mailed Jan. 30, 2009, for U.S. Appl. No. 10/950,013, filed Sep. 23, 2004, 8 pages.

Final Office Action mailed Mar. 28, 2007, for U.S. Appl. No. 10/950,013, filed Sep. 23, 2004, 18 pages.

Hannon, G.J. (Jul. 11, 2002). "RNA Interference," *Nature* 418:244-251.

Hilberg, F. et al. (Sep. 9 1993). "c-Jun is Essential for Normal Mouse Development and Hepatogenesis," *Nature* 365:179-181.

Holmdahl, R. et al. (1989). "Collagen Induced Arthritis as an Experimental Model for Rheumatoid Arthritis, Immunogenetics, Pathogenesis and Autoimmunity," *APMIS* 97:575-584.

Holmdahl, R. et al. (1991). "Multiple Epitopes on Cartilage Type II Collagen are Accessible for Antibody Binding In Vivo," *Autoimmunity* 10:27-34.

Itoh, T. et al. (2002). "The Role of Matrix Metalloproteinase-2 and Matrix metalloproteinase-9 in Antibody-Induced Arthritis," *The Journal of Immunology* 169:2643-2647.

Johnson, R.S. et al. (1993). "A Null Mutation at the *c-jun* Locus Causes Embryonic Lethality and Retarded Cell Growth in Culture," *Genes & Development* 7:1309-1317.

Kagari, T. et al. (2002). "The Importance of IL-1β and TNF-α, and the Noninvolvement of IL-6, in the Development of Monoclonal Antibody-Induced Arthritis," *The Journal of Immunology* 169:1459-1466.

Khachigian, L.M. (2002). "DNAzymes: Cutting a Path to a New Class of Therapeutics," *Current Opinion in Molecular Therapeutics* 4(2):3 pages.

Kovary, L. et al. (Sep. 1991). "The Jun and Fos Protein Families are Both Required for Cell Cycle Progression in Fibroblasts," *Molecular and Cellular Biology* 11(9):4466-4472.

Labasi, J.M. et al. (2002). "Absence of the P2X₇ Receptor Alters Leukocyte Function and Attenuates an Inflammatory Response," *The Journal of Immunology* 168:6436-6445.

Lowe, H.C. et al. (2001). "Catalytic Oligodeoxynucleotides Define a Key Regulatory Role for Early Growth Response Factor-1 in the Porcine Model of Coronary In-Stent Restenosis," *Circulation Research* 89:670-677.

Lowe, H.C. et al. (2002, e-pub. Sep. 27, 2001). "Catalytic Antisense DNA Molecules Targeting Erg-1 Inhibit Neointima Formation Following Permanent Ligation of Rat Common Carotid Arteries," *Thromb Haemost* 87:134-140.

McCoy, J.M. et al. (Sep. 2002). "The Role of Prostaglandin E2 Receptors in the Pathogenesis of Rheumatoid Arthritis," *The Journal of Clinical Investigation* 110(5):651-658.

McManus, M.T. et al (Oct. 2002). "Gene Silencing in Mammals by Small Interfering RNAs," *Nature Review* 3:737-747.

Mettouchi, A. et al. (1994). "SPARC and Thrombospondin Genes are Repressed by the *c-jun* Oncogene in Rate Embryo Fibroblasts," *The EMBO Journal*, 13(23):5668-5678.

Min, W. et al. (1997). "TNF Initiates E-Selectin Transcription in Human Endothelial Cells Through Parallel TRAF-NK-κB and TRAF-RAC/CDC42-JNK-c-June/ATF2 Pathways," *The Journal of Immunology* 159:3508-3518.

Mo, J.A. et al. (1994). "Germline-Encoded IgG Antibodies Bind Mouse Cartilage In Vivo: Epitope- and Idiotype-Specific Binding and Inhibition," *Scand. J. Immunol.* 39:122-130.

Nandakumar, K.S. et al. (Nov. 2003). "Collagen Type II-Specific Monoclonal Antibody-Induced Arthritis in Mice," *American Journal of Pathology* 163(5):1827-1837.

Non-Final Office Action mailed Aug. 18, 2008, for U.S. Appl. No. 10/950,013, filed Sep. 23, 2004, 9 pages.

Santiago, F.S. (Nov. 1999). "New DNA Enzyme Targeting Egr-1 mRNA Inhbitis Vascular Smooth Muscle Proliferation and Regrowth After Injury," *Nature Medicine* 5(11):1264-1269.

Santoro, S.W. et al. (Apr. 1997). "A General Purpose RNA-Cleaving DNA Enzyme," *Proc. Natl. Acad. Sci.* 94:4262-4266.

Schubert, S. et al. (2003). "RNA Cleaving '10-23' DNAzymes with Enhanced Stability and Activity," *Nucleic Acids Research* 31(20):5982-5992.

Shaulian, E. et al. (Dec. 8, 2000). "The Mammalian UV Response: c-Jun Induction is Required for Exit from p53-Imposed Growth Arrest," *Cell* 103:897-907.

Shaulian, E. et al. (2001). "AP-1 in Cell Proliferation and Survival," *Oncogene* 20:2390-2400.

Shen, J. et al. (2006). "Suppression of Ocular Neovascularization with siRNA Targeting VEGF Receptor 1," *Gene Therapy* 13:225-234.

Smith, L.E.H. et al. (Jan. 1994). "Oxygen-Induced Retinopathy in the Mouse," *Investigative Ophthalmology & Visual Science* 35(1):101-111.

Staines, N.A. et al. (1994). "Collagen Arthritis—What Can it Teach Us?" *British Journal of Rheumatology* 3(9)3:798-807.

Terato, K. et al. (Apr. 1, 1992). "Induction of Arthritis with Monoclonal Antibodies to Collagen," *The Journal of Immunologists* 148(7):2103-2108.

Terato, K. et al. (1995). "Collagen-Induced Arthritis in Mice: Synergistic Effect of *E. coli* Lipopolysaccharide Bypasses Epitope Specificity in the Induction of Arthritis with Monoclonal Antibodies to Type II Collagen," *Autoimmunity* 22:137-147.

Van Buul, J.D. et al. (May 2004). "Signaling in Leukocyte Transendothelial Migration," *Arteriosclerosis, Thrombosis, and Vascular Biology*, as posted on www.atvb.ahajournals.org <http://www.atvb.ahajournals.org>, last visited on May 25, 2010, 24:824-833.

Vester, B. et al. (2002, e-pub. Oct. 24, 2002). "LNAzymes: Incorporation of LNA-Type Monomers into DNAzymes Markedly Increases RNA Cleavage," *J. Am.Chem. Soc.* 124(46):13682-13683.

Wang, J. et al. (Feb. 2006). "Transcription Factor T-bet Regulates Inflammatory Arthritis Through its Function in Dendritic Cells," *The Journal of Clinical Investigation* 116(2):414-421.

Williams, R.O. et al. (2005). "Analysing the Effect of Novel Therapies on Cytokine Expression in Experimental Arthritis," *Int. J. Exp. Path.* 86:267-278.

Young, M.R. et al. (Aug. 1999). "Transgenic Mice Demonstrate AP-1 (Activator Protein-1) Transactivation is Required for Tumor Promotion," *Proc. Natl. Acad. Sci.* 96:9827-9832.

Yumoto, K. et al. (Apr. 2, 2002). "Osteopontin Deficiency Protects Joints Against Destruction in Anti-Type II Collagen Antibody-Induced Arthritis in Mice," *PNAS* 99(7):4556-4561.

* cited by examiner

Figure 2C
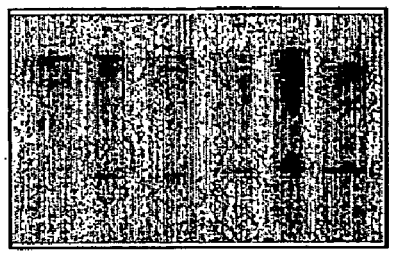
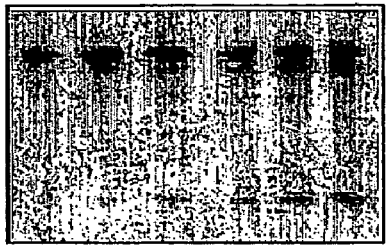
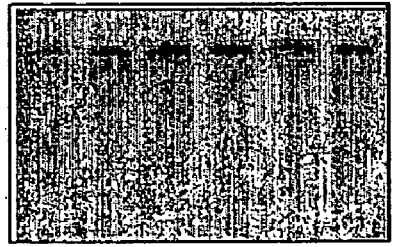

Figure 3A

```
hum c-Jun RNA    1302      1310  | 1312     1320
                  |          |  ▼ |          |
       ...5'-CAA CGC CUCG UUC CUC CCG UC-3'..

GTT GCG GAG   AAG GAG GGC-5'
            3'-L              A       G
                           G        G
                          C          C
                          A          T
                           A        A
                            C      G
                             A T C
                           Dz13
```

```
hum  5'..CAA CGC CUCG UUC CUC CCG UC-3'..
pig  5'..CAA CGC CUCG UUC CUC CAG UC-3'..
rat  5'..CAA CGC CUCG UUC CUC CAG UC-3'..
```

```
         GTT GCG GAG CAAG GAG GGC-5'   As13
   3'-L

GTT GCG GAG   AAG GAG GGC-5'   Dz13
   3'-L              A       G
                  G        G
                 C          C
                 A          T
                  A        A
                   C      G
                    A T C
```

Figure 7A c-Jun cDNA sequence (Accession J04111, NID g186624)

```
   1 ccgggggagg ggaccgggga cccgactgta acagagggcc gagaggcgtg cggcagggggg gagggtagga
  61 gaaagaaggg cccgagag aagaatcttc ggaggcagc ggagcattac ctcatcccgt gagcctccgc
 121 gggcccagag gcgagccaat tagggtggag gggaaggcct tctccatggt gacgggcggg cccgcccccc
 181 tgagagcgac gcagataagt gttgagctcg tgggtgaca tcatgggcta tttttagggg
 241 ttgactggta gcagataagt gttgagctcg ggctggataa ggctcagag ttgcactgag
 301 tgtggctgaa gcagcgaggc gggagtgagg gtgcgcggag gtgcgcggag tcaggcagac agacagacac
 361 agccagccag ccaggtcggc agtatagtcc gaactgcaaa tcttattttc tttcaccttt
 421 ctctctaact gcccagagct agcgcctgtg gctcccgggc tgtgggttcg ggagtgtcca
 481 gagagccttg tctccagccg gccccgggag gagagccctg ctgcccaggc gctgttgaca
 541 gcggcggaaa gcagcggtac cccacgcgcc cgccggggga cgtcggcgag cggctgcagc
 601 agcaaagaac tttcccgggcg gggaggaccg gagacaagtg gcagagtccc ggagcggaact
 661 tttgcaagcc tttcctgcgt cttaggcttc tccacggcgg tcaacggcgg aaggcggcgg
 721 agagccacgc aagagaagaa ggacgtgcgc tcagcttcgc tgcaccggt tgttgaactt
 781 gggcgagcgc gagccggc tgccgggcgc ccctccccc tagcagcgga ggaggggaca
 841 agtcgtcgga gtccggcggg ccaagaccg cgccggaccg gccactgcag ggtccgcact
 901 gatccgctcc gcggggagag cgctcagtgag ggaagtgag ttcgcctgcg gactccgagg
 961 aaccgctgcg cccgaagagc gctcagtgag tgaccgcgac ttttcaaagc cgggtagcgc
1021 gcgcgagtcg acaagtaaga gtgcgggagg catcttaatt aaccctgcgc tccctggagc
1081 gagctggtga ggaggcgca gcgggacga cagccagcgg gtgcgtgcgc tcttagagaa
1141 actttccctg tcaaaggctc gcggggcgc ggtgtcccc cgcttgccag agccctgttg
1201 cggccccgaa acttgtgcgc gcacgccaaa ctaacctcac gtgaagtgac ggactgttct
1261 atgactgcaa agatggaaac gacctttctat gacgatgcc tcaacgcctc gttcctccg
1321 tccgagagcg gaccttatgg ctacagtaac cccaagatcc tgaaacagag catgaccctg
1381 aacctggccg acccagtggg gagcctgaag ccgcacctcc gcgccaagaa ctcgacctc
1441 ctcacctgc ccgacgtggg gctgctcaag ctggcgtgcg ccgagctgga gcgcctgata
1501 atccagtcca gcaacgggca catcaccacc agccgaccc cacccagtt cctgtgccc
1561 aagaacgtga cagatgagca ggagggtttc gccagcggct tcgtgcgcgc cctgcgcgaa
1621 ctgcacagcc agaacacgct gcccagcgtc agcctcggtg ccgagggct acgtcggcgg caacggggca
1681 ggcatggtg ctcccgcggt agcctcggtg ccggtctac gcaggggca gcgcagcgg cggcttcagc
1741 gccagcctgc acagcgagcc acagcgagcc gccgtctac gcaaacctca gcaacttcaa ccaggcgcg
1801 ctgagcagcg gcgcggggc gccctcctac ggcgcggccg gctggcctt tcccgccgcaa
```

Figure 7A (cont)

```
1861  cccagcagc  agcagcagc  gccgcaccac  ctgccccagc  agatgcccgt  gcagcacccg
1921  cggctgcagg  cctgaagga  ggagcctcag  acagtgcccg  agatgccccgg  cgagacacccg
1981  ccctgtccc  ccatcgacat  ggagtcccag  gagcggatca  aggcggagag  gaagcgcatg
2041  aggaaccgca  tcgctgcctc  caagtgccga  aaaaggaagc  tggagagaat  cgcccggctg
2101  gaggaaaaag  tgaaaacctt  gaaagctcag  aactcggagc  tggcgtccac  ggccaacatg
2161  ctcagggaac  aggtggcaca  gcttaaacag  aaagtcatga  accacgttaa  cagtgggtgc
2221  caactcatgc  taacgcagca  gttgcaaaca  tttgaagag  agaccgtcgg  gggctgaggg
2281  gcaacgaaga  aaaaaataa  cacagagaga  cagacttgag  aacttgacaa  gttgcgacgg
2341  agagaaaaaa  gaagtgtccg  agaactaaag  ccaagggtat  ccaagttgga  ctgggttcgg
2401  tctgacggcg  ccccagtgt  gcacgagtgg  gaaggacttg  gtcgcgccct  ccctttggcgt
2461  ggagccaggg  agcggccgcc  tgcgggctgc  ccgctttgc  ggacgggctg  tcccgcgcg
2521  aacggaacgt  tggactttcg  ttaacattga  ccaagaactg  catgaccta  acattcgatc
2581  tcattcagta  ttaaaggggg  gaggggagg  gggttacaaa  ctgcaataga  gactgtagat
2641  tgcttctgta  gtactcctta  agaacacaaa  gcggggggag  ggttggggag  gggcggcagg
2701  agggaggttt  gtgagagcga  ggctgagcct  acagatgaac  tcttctggc  ctgctttcgt
2761  taactgtgta  tgtacatata  tatattttt  aattgatta  gtttgtttgt  ctgtcaataa
2821  acagcttcat  gccttgtaa  gttatttctt  gtttgttgt  aagctgattc  tgcccagtgt
2881  tgtttgtaaa  taagagattt  ggagcactct  gagtttacca  tttgtaataa  agtatataat
2941  tttttatgt  tttgtttctg  aaaattccag  aaagatatt  taagaaaata  caataaacta
3001  ttgaaagta  ctccctaac  ctctttctg  catcatctgt  agatcctagt  ctatctaggt
3061  ttgagttgaaa  gagttaagaa  tgctcgataa  aatcactctc  agtgcttctt  actattaagc
3121  agtaaaaact  gttctctatt  agacttagaa  ataaatgtac  ctgatgtacc  tgatgctatg
3181  tcaggcttca  tactccacgc  tccccagcg  tatctatatg  gaattgctta  ccaaaggcta
3241  gtgcgatgtt  tcaggaggct  ggagaaggg  gggttgcagt  ggagagggac  agcccactga
3301  gaagtcaaac  atttcaaagt  ttggattgca  tcaaagtggca  tgtgctgtga  ccatttataa
3361  tgttagaaat  tttacaatag  gtgcttattc  tcaaagcagg  aattggtggc  agatttaca
3421  aaagatgtat  ccttccaatt  tggaatcttc  tctttgacaa  ttcctagata  aaaagatggc
3481  ctttgtctta  tgaatattta  taacagcatt  ctgtcacaat  aaatgtattc  aaataccaat
3541  aacagatctt  gaattgctcc  ccttactac  ttttttgttc  ccaagttata  tactgaagtt
3601  tttatttta  gttgctgagg  tt
```

Figure 7B c-Jun DNAzyme Target Sites in Human c-Jun mRNA

The internucleotide cleavage site of the DNAzyme in the mRNA is located immediately 3' to the CAPITALISED/BOLDED/UNDERLINED nucleotide The 2 hybridising arms of the DNAzyme (9+9 nt) extend 9 nucleotides of either side of the CAPITALISED/BOLDED/UNDERLINED nucleotide. While the DNAzymes used in this study have 9+9 nt arms, any given DNAzyme is not limited to this length of arm.
The Met start codon ATG (1261-1263) is indicated

```
1141 actttccctg tcaaaggctc cggggggcgc gggtgtcccc cgcttgccag agccctgttg
1201 cggcccgaa acttgtgcgc gcacgccaaa ctaacctcac gtgaagtgac ggactgttct
1261 ATGactgcaa agAtgaaaac gaccttctAt gacgAtgccc tcaacgcctc Gttcctcccg
     Dz9(A1261)                                          Dz10(A1273)
                     Dz11(A1289)
                              Dz12(A1295)
1321 tccgagagcg gaccttatgg ctacagtaac cccaagatcc tgaaacagag catgaccctg
1381 aacctggccg accagtggg gagcctgaag ccgcacctc gcgccaagaa ctcggacctc
1441 ctcacctcgc ccgacgtggg gctgctcaag ctggcgtcgc ccgagctgga gcgcctgAta
                                                                  Dz14(A1498)
                                                          Dz13(G1311)
1501 Atccagtcca gcaacgggca catcaccacc acgccgaccc ccacccagtt cctgtgcccc
     Dz15(A1501)
1561 aagaacgtga cagatgagca ggaggggttc gccgagggct tcgtgcgcgc cctggccgaa
```

VASCULAR THERAPEUTICS

CROSS-REFERENCE TO RELATED APPLICATIONS

This application is a continuation of International Patent Application No.: PCT/AU03/00237, filed on Feb. 27, 2003, which claims priority to Australian Patent Application No.: PS 0780, filed on Feb. 27, 2002, the disclosures of which are all herein incorporated by reference in their entirety.

FIELD OF THE INVENTION

The present invention relates to methods and compositions for reducing or preventing c-Jun mediated cellular processes. In particular, the present invention relates to methods of reducing or preventing neointima formation, atherosclerosis, restenosis, graft failure or angiogenesis involving the use of DNAzymes.

BACKGROUND OF THE INVENTION

The initiating event in the pathogenesis of atherosclerosis and restenosis following angioplasty is injury to cells in the artery wall[1]. Injury or stress stimulates signalling and transcriptional pathways in vascular smooth muscle cells, stimulating their migration and proliferation and the eventual formation of a neointima. Smooth muscle cell proliferation is a key feature of neointima formation, atherosclerosis, restenosis and graft failure.

c-Jun, a prototypical member of the basic region-leucine zipper protein family, is transiently induced following arterial injury in animal models[2,3]. c-Jun forms both homodimers and heterodimers with other bZIP proteins to form the AP-1 transcription factor. While investigations over the last decade have linked AP-1 with proliferation, tumorigenesis and apoptosis, AP-1 has also been implicated in tumor suppression and cell differentiation[4]. Thus, gene-targeting strategies that down-regulate c-Jun expression do not necessarily inhibit cell proliferation.

Kanatani et al, (1996)[5] have shown that antisense oligonucleotides targeting c-Jun dose-dependently reduce the growth-inhibitory effect of dexamethasone and TGFβ. Recent reports indicate that c-Jun $NH_2$-terminal kinase/stress activated protein kinase (JNK), an upstream activator of c-Jun and numerous other transcription factors, is expressed by SMCs in human and rabbit atherosclerotic plaques[6,7] and that dominant negative JNK inhibits neointima formation after balloon injury[8]. c-Jun, however, has not been localised in human atherosclerotic lesions, nor has it been shown to play a functional role in arterial repair after injury.

It is clear, however, that the finding that c-Jun, or any other given gene, is inducibly expressed in the artery wall following balloon angioplasty does not necessarily translate to it playing a positive regulatory role in transcription, proliferation or neointima formation. For example, it has been shown that three transcriptional repressors (NAB2, GCF2, and YY1) are activated in vascular smooth muscle cells by mechanical injury in vitro, as well as in the rat artery wall. NAB2 directly binds the zinc finger transcription factor Egr-1 and represses Egr-1-mediated transcription[9]. GCF2 is a potent repressor of the expression of PDGF-A, a well-established mitogen for vascular smooth muscle cells, and inhibits smooth muscle cell proliferation[10]. Similarly, YY1 overexpression blocks smooth muscle cell growth without affecting endothelial cell proliferation[11].

c-Jun can repress, as well as activate transcription. c-Jun binds the corepressor TG-interacting factor (TGIF) to suppress Smad2 transcriptional activity[12]. c-Jun also blocks transforming growth factor beta-mediated transcription by repressing the transcriptional activity of Smad3[13].

c-Jun can inhibit, as well as stimulate proliferation. Using antisense oligonucleotides to c-Jun, Kanatani and colleagues demonstrated that inhibition of human monocytoid leukemia cell growth by TGF-beta and dexamethasone is mediated by enhanced c-Jun expression[5].

c-Jun, however, has not been directly linked to the complex process of angiogenesis, which underlies many common human diseases including solid tumor growth and corneal disease. Angiogenesis is a complex multi-step process involving proteolytic degradation of the basement membrane and surrounding extracellular matrix, microvascular endothelial cell proliferation, migration, tube formation and structural re-organisation[14].

DNAzymes

In human gene therapy, antisense nucleic acid technology has been one of the major tools of choice to inactivate genes whose expression causes disease and is thus undesirable. The anti-sense approach employs a nucleic acid molecule that is complementary to, and thereby hybridizes with, an mRNA molecule encoding an undesirable gene. Such hybridization leads to the inhibition of gene expression by mechanisms including nucleolytic degradation or steric blockade of the translational machinery.

Anti-sense technology suffers from certain drawbacks. Anti-sense hybridization results in the formation of a DNA/target mRNA heteroduplex. This heteroduplex serves as a substrate for RNAse H-mediated degradation of the target mRNA component. Here, the DNA anti-sense molecule serves in a passive manner, in that it merely facilitates the required cleavage by endogenous RNAse H enzyme. This dependence on RNAse H confers limitations on the design of anti-sense molecules regarding their chemistry and ability to form stable heteroduplexes with their target mRNA's. Anti-sense DNA molecules also suffer from problems associated with non-specific activity and, at higher concentrations, even toxicity.

As an alternative to anti-sense molecules, catalytic nucleic acid molecules have shown promise as therapeutic agents for suppressing gene expression, and are widely discussed in the literature[15-21]. Thus, unlike a conventional anti-sense molecule, a catalytic nucleic acid molecule functions by actually cleaving its target mRNA molecule instead of merely binding to it. Catalytic nucleic acid molecules can only cleave a target nucleic acid sequence if that target sequence meets certain minimum requirements. The target sequence must be complementary to the hybridizing regions of the catalytic nucleic acid, and the target must contain a specific sequence at the site of cleavage.

Catalytic RNA molecules ("ribozymes") are well documented[15,22,23], and have been shown to be capable of cleaving both RNA[15] and DNA[20] molecules. Indeed, the development of in vitro selection and evolution techniques has made it possible to obtain novel ribozymes against a known substrate, using either random variants of a known ribozyme or random-sequence RNA as a starting point[16,24,25].

Ribozymes, however, are highly susceptible to enzymatic hydrolysis within the cells where they are intended to perform their function. This in turn limits their pharmaceutical applications.

Recently, a new class of catalytic molecules called "DNAzymes" was created[26,27]. DNAzymes are single-stranded, and cleave both RNA[16,27] and DNA[21]. A general model for the DNAzyme has been proposed, and is known as the "10-23" model. DNAzymes following the "10-23" model, also referred to simply as "10-23 DNAzymes", have a catalytic domain of 15 deoxyribonucleotides, flanked by two substrate-recognition domains of variable deoxyribonucleotide arm length. In vitro analyses show that this type of DNAzyme can effectively cleave its substrate RNA at purine: pyrimidine junctions under physiological conditions[27].

DNAzymes show promise as therapeutic agents. However, DNAzyme success against a disease caused by the presence of a known mRNA molecule is not predictable. This unpredictability is due, in part, to two factors. First, certain mRNA secondary structures can impede a DNAzyme's ability to bind to and cleave its target mRNA. Second, the uptake of a DNAzyme by cells expressing the target mRNA may not be efficient enough to permit therapeutically meaningful results.

Investigation of the precise regulatory role of c-Jun in the injured artery wall and indeed, in other disease settings such as angiogenesis, has been hampered by the lack of a specific pharmacological inhibitor. DNAzymes represent a new class of gene targeting agent with specificity conferred by the sequence of nucleotides in the two arms flanking a catalytic core[27], with advantages over ribozymes of substrate specificity and stability[27,28]. To date, neither c-Jun nor indeed any other Jun family member has been targeted using catalytic nucleic acid strategies.

SUMMARY OF THE INVENTION

The present inventors have demonstrated using a DNAzyme targeting c-Jun, that c-Jun plays a positive role in restenosis, neointima formation, atherosclerosis, graft failure and angiogenesis.

In a first aspect the present invention consists in a method of preventing or reducing angiogenesis and/or neovascularisation in a subject, the method comprising administering to the subject a prophylactically effective dose of a nucleic acid which decreases the level of c-Jun mRNA, c-Jun mRNA translation or nuclear accumulation or activity of c-Jun.

In a second aspect the present invention consists in a method of treating or inhibiting a condition selected from the group consisting of restenosis, neointima formation, graft failure and atherosclerosis in a subject, the method comprising administering to the subject a prophylactically effective dose of a nucleic acid which decreases the level of c-Jun mRNA, c-Jun mRNA translation or nuclear accumulation or activity of c-Jun.

In a third aspect the present invention consists in a method of treating or inhibiting solid tumour growth in a subject, the method comprising administering to the subject a prophylactically effective dose of a nucleic acid which decreases the level of c-Jun mRNA, c-Jun mRNA translation or nuclear accumulation or activity of c-Jun.

In a preferred embodiment of the present invention, the nucleic acid is selected from the group consisting of a DNAzyme targeted against c-Jun, a c-Jun antisense oligonucleotide, a ribozyme targeted against c-Jun, and a ssDNA targeted against c-Jun dsDNA such that the ssDNA forms a triplex with the c-Jun dsDNA. In an alternative embodiment the nucleic acid is dsRNA targeted against c-Jun mRNA, a nucleic acid molecule which results in production of dsRNA targeted against c-Jun mRNA or small interfering RNA molecules targeted against c-Jun mRNA.

In a fourth aspect, the present invention provides a method of screening for an agent which inhibits restenosis, neointima formation, graft failure, atherosclerosis, angiogenesis, and/or solid tumour growth the method comprising testing a putative agent for the ability to inhibit induction of c-Jun, decrease expression of c-Jun or decrease the nuclear accumulation or activity of c-Jun.

In a fifth aspect, the present invention consists in a catalytic nucleic acid which specifically cleaves c-Jun mRNA in the region of residues A287 to A1501.

In a sixth aspect the present invention consists in an antisense oligonucleotide which specifically binds c-Jun mRNA in the region of residues U1296 to G1497.

In a seventh aspect the present invention consists in a pharmaceutical composition comprising the catalytic nucleic acid of the fifth aspect of the invention or the antisense oligonucleotide of the sixth aspect of the invention and a pharmaceutically acceptable carrier.

In an eighth aspect the present invention consists in an angioplastic stent for inhibiting onset of restenosis comprising an angioplastic stent operably coated with a prophylactically effective dose of a nucleic acid which decreases the level of c-Jun mRNA, c-Jun mRNA translation or nuclear accumulation or activity of c-Jun.

In a ninth aspect, the present invention consists in a method for inhibiting the onset of restenosis, neointima formation, graft failure and/or atherosclerosis in a subject undergoing angioplasty comprising topically administering a stent according to the eighth aspect of the invention to the subject at around the time of angioplasty.

BRIEF DESCRIPTION OF FIGURES

FIG. 7. A, c-Jun cDNA sequence (Accession J04111, NID g186624) (SEQ ID NO:1). B, Location of DNAzyme target sites in c-Jun mRNA (SEQ ID NO:33). (SEQ ID NO: 23: hybridising arms of the DNAzyme (9+9 nt) Dz9 (A1261). SEQ ID NO: 24: hybridising arms of the DNAzyme (9+9 nt) Dz10 (A1273). SEQ ID NO: 25: hybridising arms of the DNAzyme (9+9 nt) Dz11 (A1289). SEQ ID NO: 26: hybridising arms of the DNAzyme (9+9 nt) Dz12 (A1295). SEQ ID NO: 27: hybridising arms of the DNAzyme (9+9 nt) Dz13 (G1311). SEQ ID NO: 28: hybridising arms of the DNAzyme (9+9 nt) Dz14 (A1498). SEQ ID NO: 29 hybridising arms of the DNAzyme (9+9 nt) DZ15 (A1501).)

DETAILED DESCRIPTION OF THE INVENTION

Figure 1:
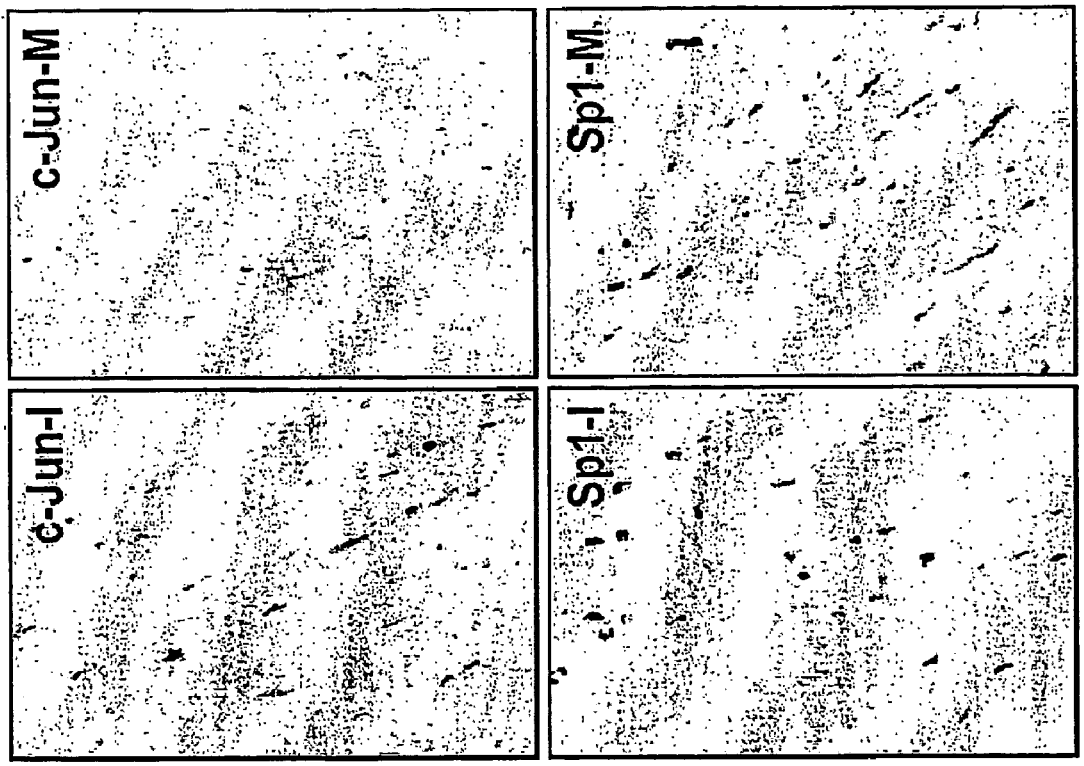
FIG. 1. c-Jun and Sp1 expression in human atherosclerotic lesions. Immunohistochemical staining for c-Jun and Sp1 in 5 μm sections of human carotid atherosclerotic lesions. The intima and media are indicated in the figure. Staining is representative of three independent samples.

The present inventors have demonstrated c-Jun expression by smooth muscle cells in the human atheromatous lesion (FIG. 1). c-Jun is poorly, if at all, expressed by smooth muscle cells in the normal media. In contrast, the zinc finger transcription factor Sp1 is expressed in both the intima and media (FIG. 1).

Neointima formation is a characteristic feature of common vascular pathologies, such as atherosclerosis and post-angioplasty restenosis, and involves smooth muscle cell proliferation.

In addition to its expression by smooth muscle cells, the present inventors have also demonstrated that c-Jun is linked to the complex process of angiogenesis. In particular, expression of c-Jun was found in vascularized primary human melanoma which has not been previously described.

A gene-specific DNAzyme targeting c-Jun (designated Dz13) was generated. Dz13 cleaves c-Jun RNA and inhibits inducible c-Jun protein expression in vascular smooth muscle cells with a potency exceeding its exact non-catalytic antisense oligodeoxynucleotide equivalent. Moreover, Dz13 abrogated smooth muscle cell repair after injury in vitro and neointima formation in rat carotid arteries in vivo.

Dz13 also blocked endothelial proliferation, migration and microtubule formation with a potency exceeding its exact non-catalytic antisense oligodeoxynucleotide equivalent. It inhibited neovascularisation in rat cornea and melanoma growth in mice.

These findings demonstrate the pivotal regulatory role of c-Jun in neointima formation in the injured artery wall, as well as angiogenesis.

In a first aspect the present invention consists in a method of preventing or reducing angiogenesis and/or neovascularisation in a subject, the method comprising administering to the subject a prophylactically effective dose of a nucleic acid which decreases the level of c-Jun mRNA, c-Jun mRNA translation or nuclear accumulation or activity of c-Jun.

In a second aspect the present invention consists in a method of treating or inhibiting a condition selected from the group consisting of restenosis, neointima formation, graft failure and atherosclerosis in a subject, the method comprising administering to the subject a prophylactically effective dose of a nucleic acid which decreases the level of c-Jun mRNA, c-Jun mRNA translation or nuclear accumulation or activity of c-Jun.

In a third aspect the present invention consists in a method of treating or inhibiting solid tumour growth in a subject, the method comprising administering to the subject a prophylactically effective dose of a nucleic acid which decreases the level of c-Jun mRNA, c-Jun mRNA translation or nuclear accumulation or activity of c-Jun.

In a preferred embodiment of the first aspect of the invention the angiogenesis is ocular angiogenesis.

In a preferred embodiment of the third aspect of the invention the solid tumour is melanoma.

Although the subject may be any animal or human, it is preferred that the subject is a human.

As will be recognised by those skilled in this field there are a number of means by which the method of the present invention-may be achieved.

In a preferred embodiment, the method is achieved by cleavage of c-Jun mRNA by a sequence-specific DNAzyme. In a further preferred embodiment, the DNAzyme comprises
  (i) a catalytic domain which cleaves mRNA at a purine:pyrimindine cleavage site;
  (ii) a first binding domain contiguous with the 5' end of the catalytic domain; and
  (iii) a second binding domain contiguous with the 3' end of the catalytic domain,
  wherein the binding domains are sufficiently complementary to two regions immediately flanking a purine:pyrimidine cleavage site within the c-Jun mRNA such that the DNAzyme cleaves the c-Jun mRNA.

As used herein, "DNAzyme" means a DNA molecule that specifically recognizes and cleaves a distinct target nucleic acid sequence, which may be either DNA or RNA.

In a preferred embodiment, the binding domains of the DNAzyme are complementary to the regions immediately flanking the cleavage site. It will be appreciated by those skilled in the art, however, that strict complementarity may not be required for the DNAzyme to bind to and cleave the c-Jun mRNA.

The binding domain lengths (also referred to herein as "arm lengths") can be of any permutation, and can be the same or different. In a preferred embodiment, the binding domain lengths are at least 6 nucleotides. Preferably, both binding domains have a combined total length of at least 14 nucleotides. Various permutations in the length of the two binding domains, such as 7+7, 8+8 and 9+9, are envisioned. Preferably, the length of the two binding domains are 9+9.

The catalytic domain of a DNAzyme of the present invention may be any suitable catalytic domain. Examples of suitable catalytic domains are described in Santoro and Joyce, 1997[27] and U.S. Pat. No. 5,807,718. In a preferred embodiment, the catalytic domain has the nucleotide sequence GGCTAGCTACAACGA (SEQ ID NO:4).

It is preferred that the DNAzyme cleavage site is within the region of residues A287 to A1501, more preferably U1296 to G1497, of the c-Jun mRNA. It is particularly preferred that the cleavage site within the c-Jun mRNA is the GU site corresponding to nucleotides 1311-1312.

In a further preferred embodiment, the DNAzyme has the sequence

```
                                              (SEQ. ID NO: 5)
       5'-cgggaggaaGGCTAGCTACAACGAgaggcgttg-3'.
```

In applying DNAzyme-based treatments, it is preferable that the DNAzymes be as stable as possible against degradation in the intra-cellular milieu. One means of accomplishing this is by incorporating a 3'-3' inversion at one or more termini of the DNAzyme. More specifically, a 3'-3' inversion (also referred to herein simply as an "inversion") means the covalent phosphate bonding between the 3' carbons of the terminal nucleotide and its adjacent nucleotide. This type of bonding is opposed to the normal phosphate bonding between the 3' and 5' carbons of adjacent nucleotides, hence the term "inversion". Accordingly, in a preferred embodiment, the 3'-end nucleotide residue is inverted in the building domain contiguous with the 3' end of the catalytic domain. In addition to inversions, the instant DNAzymes may contain modified nucleotides. Modified nucleotides include, for example, N3'-P5' phosphoramidate linkages, and peptide-nucleic acid linkages. These are well known in the art.

In a particularly preferred embodiment, the DNAzyme includes an inverted T at the 3' position.

In order to increase resistance to exonucleolytic degradation and helical thermostability locked nucleic acid analogues can be produced. Further information regarding these analogues is provided in Vester et al, J. Am. Chem. Soc., 2002, 124, 13682-13683, the disclosure of which is incorporated herein by cross reference.

In another embodiment, the method is achieved by inhibiting translation of the c-Jun mRNA using synthetic antisense DNA molecules that do not act as a substrate for RNase and act by sterically blocking gene expression.

In another embodiment, the method is achieved by inhibiting translation of the c-Jun mRNA by destabilising the mRNA using synthetic antisense DNA molecules that act by directing the RNase degradation of the c-Jun mRNA present in the heteroduplex formed between the antisense DNA and mRNA.

In one preferred embodiment of the present invention, the antisense oligonucleotide comprises a sequence which hybridises to c-Jun within the region of residues U1296 to G1497.

It will be understood that the antisense oligonucleotide need not hybridise to this whole region. It is preferred that the antisense oligonucleotide has the sequence CGGGAG-GAACGAGGCGTTG (SEQ ID NO:6).

In another embodiment, the method is achieved by inhibiting translation of the c-Jun mRNA by cleavage of the mRNA by sequence-specific hammerhead ribozymes and derivatives of the hammerhead ribozyme such as the Minizymes or Mini-ribozymes or where the ribozyme is derived from:
(i) the hairpin ribozyme,
(ii) the Tetrahymena Group I intron,
(iii) the Hepatitis Delta Viroid ribozyme or
(iv) the Neurospera ribozyme.

It will be appreciated by those skilled in the art that the composition of the ribozyme may be;
(i) made entirely of RNA,
(ii) made of RNA and DNA bases, or
(iii) made of RNA or DNA and modified bases, sugars and backbones Within the context of the present invention, the ribozyme may also be either;
(i) entirely synthetic or
(ii) contained within a transcript from a gene delivered within a virus-derived vector, expression plasmid, a synthetic gene, homologously or heterologously integrated into the patients genome or delivered into cells ex vivo, prior to reintroduction of the cells of the patient, using one of the above methods.

It is preferred that the ribozyme cleaves the c-Jun mRNA in the region of residues U1296 to G1497.

In another embodiment, the method is achieved by inhibition of the ability of the c-Jun gene to bind to its target DNA by expression of an antisense c-Jun mRNA.

In a still further embodiment the nucleic acid is dsRNA targeted against c-Jun mRNA, a nucleic acid molecule which results in production of dsRNA targeted against c-Jun mRNA or small interfering RNA molecules targeted against c-Jun mRNA. So called "RNA interference" or "RNAi" is well known and further information regarding RNAi is provided in Hannon, Nature, Vol 418, 2002, 24251, and McManus et al, Nature Reviews: Genetics, Vol 3, 2002,737-747, the disclosures of which are incorporated herein by cross-reference.

In one embodiment, the method is achieved by targeting the c-Jun gene directly using triple helix (triplex) methods in which a ssDNA molecule can bind to the dsDNA and prevent transcription.

In another embodiment, the method is achieved by inhibiting transcription of the c-Jun gene using nucleic acid transcriptional decoys. Linear sequences can be designed that form a partial intramolecular duplex which encodes a binding site for a defined transcriptional factor.

In another embodiment, the method is achieved by inhibition of c-Jun activity as a transcription factor using transcriptional decoy methods.

In another embodiment, the method is achieved by inhibition of the ability of the c-Jun gene to bind to its target DNA by drugs that have preference for GC rich sequences. Such drugs include nogalamycin, hedamycin and chromomycin A3[29].

Administration of the inhibitory nucleic acid may be effected or performed using any of the various methods and delivery systems known to those skilled in the art. The administering can be performed, for example, intravenously, orally, via implant, transmucosally, transdermally, topically, intramuscularly, subcutaneously or extracorporeally. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition. In one embodiment the delivery vehicle contains $Mg^{2+}$ or other cation(s) to serve as co-factor(s) for efficient DNAzyme bioactivity.

Transdermal delivery systems include patches, gels, tapes and creams, and can contain excipients such as solubilizers, permeation enhancers (e.g., fatty acids, fatty acid esters, fatty alcohols and amino adds), hydrophilic polymers (e.g., polycarbophil and polyvinylpyrolidone), and adhesives and tackifiers (e.g., polyisobutylenes, silicone-based adhesives, acrylates and polybutene).

Transmucosal delivery systems include patches, tablets, suppositories, pessaries, gels and creams, and can contain excipients such as solubilizers and enhancers (e.g., propylene glycol, bile salts and amino adds), and other vehicles (e.g., polyethylene glycol, fatty add esters and derivatives, and hydrophilic polymers such as hydroxypropylmethylcellulose and hyaluronic acid).

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

Topical delivery systems include, for example, gels and solutions, and can contain excipients such as solubilizers, permeation enhancers (e.g., fatty acids, fatty add esters, fatty alcohols and amino acids), and hydrophilic polymers (e.g., polycarbophil and polyvinylpyrolidone). In the preferred embodiment, the pharmaceutically acceptable carrier is a liposome or a biodegradable polymer. Examples of carriers which can be used in this invention include the following: (1) Fugene6® (Roche); (2) SUPERFECT®(Qiagen); (3) Lipofectamine 2000®(GIBCO BRL); (4) CellFectin, 1:1.5 (M/M) liposome formulation of the cationic lipid N,NI,NII,NIII-tetramethyl-N,NI,NII,NIII-tetrapalmitylspermine and dioleoyl phosphatidyl-ethanolamine (DOPE)(GIBCO BRL); (5) Cytofectin GSV, 2:1 (M/M) liposome formulation of a cationic lipid and DOPE (Glen Research); (6) DOTAP (N-[1-(2,3-dioleoyloxy)-N,N,N-trimethyl-ammoniummethylsulfate) (Boehringer Mannheim); and (7) Lipofectamine, 3:1 (M/M) liposome formulation of the polycationic lipid DOSPA and the neutral lipid DOPE (GIBCO BRL).

Delivery of the nucleic acids described may also be achieved via one or more, of the following non-limiting examples of vehicles:
(a) liposomes and liposome-protein conjugates and mixtures;
(b) non-liposomal lipid and cationic lipid formulations;
(c) activated dendrimer formulations;
(d) within a polymer formulation such as polyethylenimine (PEI) or pluronic gels or within ethylene vinyl acetate copolymer (EVAc). The polymer is preferably delivered intra-luminally;

(e) within a viral-liposome complex, such as Sendai virus;
(f) as a peptide-DNA conjugate;
(g) using catheters to deliver intra-luminal formulations of the nucleic acid as a solution or in a complex with a liposome;
(h) catheter delivery to adventitial tissue as a solution or in a complex with a liposome;
(i) the nucleic acid may be bound to a delivery agent such as a targeting moiety, or any suitable carrier such as a peptide or fatty acid molecule;
(j) the nucleic acid may be delivered by a double angioplasty balloon device fixed to catheter; or
(k) the nucleic acid could be delivered on a specially prepared stent of the Schatz-Palmaz or derivative type. The stent could be coated with a polymer or agent impregnated with nucleic acid that allows controlled release of the molecules at the vessel wall.

Determining the prophylactically effective dose of the instant pharmaceutical composition can be done based on animal data using routine computational methods. In one embodiment, the prophylactically effective does contains between about 0.1 mg and about 1 g of the instant DNAzyme. In another embodiment, the prophylactically effective dose contains between about 1 mg and about 100 mg of the instant DNAzyme. In a further embodiment, the prophylactically effective does contains between about 10 mg and about 50 mg of the instant DNAzyme. In yet a further embodiment, the prophylactically effective does contains about 25 mg of the instant DNAzyme.

In the case of the prevention or reduction of angiogenesis or inhibition of solid tumour growth, in a preferred embodiment, the agent is injected into or proximal the tumour. Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

It is also envisaged that nucleic acid agents targeting c-Jun may be administered by ex vivo transfection of cell suspensions, thereby inhibiting angiogenesis.

In a fourth aspect, the present invention provides a method of screening for an agent which inhibits restenosis, neointima formation, atherosclerosis, graft failure and/or angiogenesis, the method comprising testing a putative agent for the ability to inhibit induction of c-Jun, decrease expression of c-Jun or decrease the nuclear accumulation or activity of c-Jun.

The putative agent may be tested for the ability to inhibit c-Jun by any suitable means. For example, the test may involve contacting a cell which expresses c-Jun with the putative agent and monitoring the production of c-Jun mRNA (by, for example, Northern blot analysis) or c-Jun protein (by, for example, immunohistochemical analysis or Western blot analysis or electrophoretic mobility shift assay). Other suitable tests will be known to those skilled in the art.

In a fifth aspect the present invention consists in a catalytic nucleic acid which specifically cleaves c-Jun mRNA in the region of residues A287 to A1501, preferably U1296 to G1497.

In a preferred embodiment, the catalytic nucleic acid is a sequence-specific DNAzyme comprising
  (i) a catalytic domain which cleaves mRNA at a purine: pyrimidine cleavage site;
  (ii) a first binding domain contiguous with the 5' end of the catalytic domain; and
  (iii) a second binding domain contiguous with the 3' end of the catalytic domain,
  wherein the binding domains are sufficiently complementary to two regions immediately flanking a purine:pyrimidine cleavage site within the c-Jun mRNA such that the DNAzyme cleaves the c-Jun mRNA in the region of residues U1296 to G1497.

It is particularly preferred that the cleavage site within the c-Jun mRNA is the GU site corresponding to nucleotides 1311-1312.

In a preferred embodiment, the binding domains of the DNAzyme are complementary to the regions immediately flanking the cleavage site. It will be appreciated by those skilled in the art, however, that strict complementarity may not be required for the DNAzyme to bind to and cleave the c-Jun mRNA.

The binding domain lengths (also referred to herein as "arm lengths") can be of any permutation, and can be the same or different. In a preferred embodiment, the binding domain lengths are at least 6 nucleotides. Preferably, both binding domains have a combined total length of at least 14 nucleotides. Various permutations in the length of the two binding domains, such as 7+7, 8+8 and 9+9, are envisioned. Preferably, the length of the two binding domains are 9+9.

The catalytic domain of a DNAzyme of the present invention may be any suitable catalytic domain. Examples of suitable catalytic domains are described in Santoro and Joyce, 1997[27] and U.S. Pat. No. 5,807,718. In a preferred embodiment, the catalytic domain has the nucleotide sequence GGCTAGCTACAACGA.

In a further preferred embodiment, the DNAzyme has the sequence (SEQ. ID NO: 5)
5'-cgggaggaaGGCTAGCTACAACGAgaggcgttg-3'.

In applying DNAzyme-based treatments, it is preferable that the DNAzymes be as stable as possible against degradation in the intra-cellular milieu. One means of accomplishing this is by incorporating a 3'-3' inversion at one or more termini of the DNAzyme. More specifically, a 3'-3' inversion (also referred to herein simply as an "inversion") means the covalent phosphate bonding between the 3' carbons of the terminal nucleotide and its adjacent nucleotide. This type of bonding is opposed to the normal phosphate bonding between the 3' and 5' carbons of adjacent nucleotides, hence the term "inversion". Accordingly, in a preferred embodiment, the 3'-end nucleotide residue is inverted in the building domain contiguous with the 3' end of the catalytic domain. In addition to inversions, the instant DNAzymes may contain modified nucleotides. Modified nucleotides include, for example, N3'-P5' phosphoramidate linkages, and peptide-nucleic acid linkages. These are well known in the art.

In a particularly preferred embodiment, the DNAzyme includes an inverted T at the 3' position.

In another embodiment, the catalytic nucleic acid is a sequence-specific hammerhead ribozyme and derivatives of the hammerhead ribozyme such as the Minizymes or Miniribozymes or where the ribozyme is derived from:
  (i) the hairpin ribozyme,
  (ii) the Tetrahymena Group I intron,
  (iii) the Hepatitis Delta Viroid ribozyme or
  (iv) the Neurospera ribozyme
wherein the ribozyme cleaves the c-Jun mRNA in the region of residues U1296 to G1497.

It will be appreciated by those skilled in the art that the composition of the ribozyme may be;
(i) made entirely of RNA,
(ii) made of RNA and DNA bases, or
(iii) made of RNA or DNA and modified bases, sugars and backbones.

Within the context of the present invention, the ribozyme may also be either;
(i) entirely synthetic or
(ii) contained within a transcript from a gene delivered within a virus-derived vector, expression plasmid, a synthetic gene, homologously or heterologously integrated into the patients genome or delivered into cells ex vivo, prior to reintroduction of the cells of the patient, using one of the above methods.

In a sixth aspect the present invention consists in an antisense oligonucleotide which specifically binds c-Jun mRNA in the region of residues U1296 to G1497.

It will be understood that the antisense oligonucleotide need not hybridise to this whole region. It is preferred that the antisense oligonucleotide has the sequence CGGGAG-GAACGAGGCGTTG (SEQ ID NO:6).

In a seventh aspect the present invention consists in a pharmaceutical composition comprising the catalytic nucleic acid of the fifth aspect of the invention or the antisense oligonucleotide of the sixth aspect of the invention and a pharmaceutically acceptable carrier.

In an eighth aspect the present invention consists in an angioplastic stent for inhibiting onset of restenosis comprising an angioplastic stent operably coated with a prophylactically effective dose of a nucleic acid which decreases the level of c-Jun mRNA, c-Jun mRNA translation or nuclear accumulation or activity of c-Jun.

It is preferred that the agent is the catalytic nucleic acid of the fifth aspect of the invention or the antisense oligonucleotide of the sixth aspect of the invention In a ninth aspect the present invention consists in a method for inhibiting the onset of restenosis in a subject undergoing angioplasty comprising topically administering a stent according to the eighth aspect of the invention to the subject at around the time of angioplasty.

Angioplastic stents, also known by other terms such as "intravascular stents" or simple "stents", are well known in the art. They are routinely used to prevent vascular closure due to physical anomalies such as unwanted inward growth of vascular tissue due to surgical trauma. They often have a tubular, expanding lattice-type structure appropriate for their function, and can optionally be biodegradable.

In this invention, the stent can be operably coated with the instant pharmaceutical composition using any suitable means known in the art. Here, "operably coating" a stent means coating it in a way that permits the timely release of the pharmaceutical composition into the surrounding tissue to be treated once the coated stent is administered. Such coating methods, for example, can use the polymer polypyrrole.

As used herein, administration "at around the time of angioplasty" can be performed during the procedure, or immediately before or after the procedure. The administering can be performed according to known methods such as catheter delivery.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood, preferred forms thereof will now be described with reference to the following non-limiting and Examples.

Methods

DNAzymes, in vitro Transcript and Cleavage Experiments

DNAzymes were synthesized by Oligos Etc. or TriLink with a 3'-3'-linked inverted T and purified by HPLC. A $^{32}$P-labeled 668 nt c-Jun RNA transcript was prepared by in vitro transcription (using T7 polymerase) of pBluescript containing the insert, cut previously with XbaI. Reactions were performed in a total volume of 20 µl containing 10 mM $MgCl_2$, 5 mM Tris pH 7.5, 150 mM NaCl, 0.5 pmol of in vitro transcribed substrate and 10 pmol DNAzyme, unless dose-dependent cleavage experiments were performed, where stoichiometry is indicated in the figure. Reactions were allowed to proceed for various times at 37° C. and quenched by transferring an aliquot to tubes containing formamide loading buffer. Samples were run on 12% denaturing polyacrylamide gels and autoradiographed overnight at −80° C.

Smooth Muscle Cell Culture, Transfection, Proliferation and Wounding Assays

Smooth muscle cells derived from human and porcine coronary arteries were obtained from Cell Applications, Inc (San Diego, Calif.), and cultured in Waymouth's medium, pH 7.4, containing 10% fetal bovine serum, 50 µg/ml streptomycin and 50 IU/ml penicillin at 37° C. in a humidified atmosphere of 5% $CO_2$. In all in vitro experiments, smooth muscle cells were not used beyond passage 7. Transfections were performed in smooth muscle cells six h after the change of medium to serum-free, and again at the time of serum-stimulation 24 h after the start of arrest, using FuGENE6 according to the manufacturer's instructions (Roche). In proliferation assays, growth-arrested smooth muscle cells in 96 well plates (Nunc-InterMed) were transfected with the indicated concentration of DNAzyme or oligonucleotide, then exposed to 5% FBS at 37° C. for 72 h. The cells were trypsinized and the suspension quantitated in an automated Coulter counter. In wounding assays, confluent smooth muscle cells in chamber slides (Nunc-InterMed) transfected with DNAzyme were injured by scraping with a sterile toothpick. Cells were treated with mitomycin C (Sigma) (20 µM) for 2 h prior to injury to block proliferation. Seventy-two h after injury, the cells were washed with PBS, pH 7.4, fixed with formaldehyde and stained with hematoxylin and eosin.

Antibodies

Western immunoblot, and immunohistochemical analysis on human carotid endarterectomy specimens, were performed using rabbit polyconal anti-peptide antibodies targeting c-Jun and Sp1 (Santa Cruz Biotechnology) essentially as described[11,30].

Common Carotid Injury and Evaluation of Neointima Formation

Sprague Dawley rats (450 g males) were anaesthetised using ketamine (60 mg/kg, i.p.) and xylazine (8 mg/kg, i.p.). The left common and external carotid arteries were exposed via a midline neck incision, and a ligature was applied to the external carotid proximal to the bifurcation. Two hundred μl (at 4° C.) containing DNAzyme (750 μg), of FuGENE6 (30 μl), MgCl$_2$ (1 mM) and P127 Pluronic gel (BASF) was applied around the vessel, 6 h prior to and again at the time of ligation. The solution gelified after contact with the vessel at 37° C. The incision was sutured and the rats allowed to recover. Animals were sacrificed 21 days after injury by lethal injection of ketamine/xylazine, and perfusion fixed with 10% (v:v) formaldehyde at 120 mm Hg. Carotids were placed in 10% formaldehyde, embedded in 3% (w:v) agarose, fixed in paraffin and sectioned 1000 μm from the tie. Neointimal and medial areas in 5 μm sections stained with hematoxylin and eosin were determined morphometrically and expressed as a mean ratio per group of 6 rats.

Endothelial Cell Culture and Transfection

Human microvascular endothelial cells-1 (HMEC-1) were grown in MCDB131 medium (GIBCO BRL) containing 10% fetal bovine serum (FBS), 2 mM L-glutamine, 10 ng/ml epidermal growth factor, 1 μg/ml hydrocortisone, and 5 U/ml penicillin/streptomycin. Murine brain microvascular endothelial cells (bEND-3) were cultured in Dulbecco's modified Eagles medium (DMEM GIBCO BRL) containing 10% fetal calf serum, 2 mM L-glutamine and 5 U/ml penicillin/streptomycin. DNAzyme transfections were performed with FuGENE6 using subconfluent cells (60-70%) 6 h after the initiation of growth-arrest in serum-free medium. The cells were transfected a second time in medium containing serum 18 h after the initial transfection.

Western Blot Analysis

Growth-quiescent endothelial cells transfected twice with DNAzyme were incubated in serum for 2 h prior to the preparation of total cell extracts in 150 mM NaCl, 50 mM Tris-HCl (pH 7.5), 1% sodium deoxycholate, 0.1% SDS, 1% Triton X-100, 5 mM EDTA, 10 μg/ml leupeptin, 1% aprotinin and 2 mM PMSF. These extracts were resolved on 12% PAGE gels, transferred onto PVDF nylon membranes and probed with the indicated antibodies (Santa Cruz Biotechnology). Proteins were detected by chemiluminescence (NEN).

Preparation of Nuclear Extracts and EMSA

Cells were scraped into ice-cold phosphate-buffered saline (PBS), pelleted and resuspended in lysis buffer containing 10 mM Hepes, pH 7.9, 1.5 mM MgCl$_2$, 10 mM KCl, 0.5% NP-40, 1 mM DTT, 0.5 mM PMSF, 4 μg/ml aprotinin and 10 μg/ml leupeptin. After incubation on ice for 5 min. the pellets were resuspended in 20 mM Hepes, pH7.9, 15 mM MgCl$_2$, 420 mM NaCl, 0.2 mM EDTA, 1 mM DTT, 0.5 mM PMSF, 4 μg/ml aprotinin and 10 μg/ml leupeptin, shaking at low speed for 20 min. The supernatant was mixed with an equal volume of 20 mM Hepes, pH 7.9, 100 mM KCl, 0.2 mM EDTA, 20% glycerol, 1 mM DTT, 0.5 mM PMSF, 4 μg/ml aprotinin and 10 μg/ml leupeptin. Double-stranded oligonucleotides were 5'-end-labeled with ($\gamma^{32}$P)ATP using T4 polynucleotide kinase (NEB). Reactions were performed in the presence of 10 mM Tris-HCl, pH7.5, 50 mM NaCl, 0.5 mM DTT, 0.5 mM EDTA, 1 mM MgCl$_2$, 5% glycerol, 2.5 μg poly dI-dC with 150,000 cpm of probe for 20 min at room temperature. Bound complexes were resolved by non-denaturing 8% PAGE in tris-borate-EDTA buffer system. For supershift studies nuclear extracts were incubated with 2 μg of c-Jun antibody 10 min prior to the addition of the $^{32}$P-labeled probe.

Endothelial Proliferation and Wounding Assays

Growth-quiescent endothelial cells treated with DNAzyme were incubated in medium containing serum for 2 days prior to trypsinization, resuspension in Isoton II (Coulter Electronics) and quantitation using a Coulter counter (Coulter Z series). Endothelial cells transfected with DNAzyme were grown to confluence and injured by scraping with a P200 tip. Two days after injury, the cells were washed twice in PBS, pH 7.4, fixed in 4% paraformaldehyde (v/v), and stained in hematoxylin and eosin prior to photomicroscopy. Cell numbers in the denuded zone of each group were determined under 100× magnification in triplicate in a blinded manner.

Microtubule Formation Assay

Endothelial cells were grown in 100 mm petri-dishes were transfected with DNAzyme then trypsinized and resuspended (30,000 cells per well) into 96 well plates coated with 100 μl of matrigel (BD Biosciences). Microtubule formation was quantified by microscopy under 400× magnification in a blinded manner.

HMEC-1 Migration and Invasion

Polycarbonate membranes (12 μm pore size) were coated overnight with matrigel (1 mg/ml) (BD Biosciences) or collagen type I (1 mg/ml) (Sigma) and air-dried. A suspension of endothelial cells (4×10$^5$/ml) previously transfected with DNAzyme was placed in the upper chamber of modified Boyden chambers. Media in the lower chamber was supplemented with FGF-2 (20 ng/ml). After a 24 h incubation at 37° C., filters were fixed in methanol, stained with hematoxylin and cells that had migrated to the underside of the membrane were quantitated under 400× magnification.

RT-PCR

Cells were transfected with 0.4 μM of Dz13 or Dz13scr 6 h after arrest. Eighteen h later, the cells were incubated with TGF-beta1 (10 ng/ml, Promega) and transfected again with 0.4 μM Dz13 or Dz13scr. Total RNA was prepared using Trizol (Invitrogen) after 24 h. Single strand cDNA was synthesized from 4 μg total RNA in a 20-μl volume reaction with 200 U reverse transcriptase (Superscript II), 500 μM dNTPs, and 0.5 μg oligo (dt)15 (Life Technologies). PCR was performed in a 20 μl volume with 1 U DNA polymerase, 100 μM dNTPs, 30 mM MgCl$_2$ (Invitrogen) and 0.1 μM primers. MMP-2 PCR was performed at 95° C. for 30 s, 57° C. for 30 s, and 72° C. for 40 s over 22 cycles. The predicted MMP-2 amplification product was 446 bp. cDNA samples were normalized to GAPDH (452 bp product). Primers were as follows:

```
                                              (SEQ. ID NO: 15)
MMP-2:
Forward 5'-GGG ACA AGA ACC AGA TCA CAT AC-3', (SEQ. ID NO: 16)
Reverse 5'-CTT CTC AAA GTT GTA GGT GGT GG-3';

(SEQ. ID NO: 17)
GAPDH:
Forward 5'-ACC ACA GTC CAT GCC ATC AC-3', (SEQ. ID NO: 18)
Reverse 5'-TCC ACC ACC CTG TTG CTG TA-3'.
```

MMP-2 ELISA

Endothelial cells transfected with DNAzyme were incubated with 10 ng/ml TGF-beta1 for 2 days in medium supplemented with 0.1% FBS. Conditioned media was harvested, centrifuged, normalized for equal protein, and levels of MMP-2 determined using commercial ELISA (Amersham Biosciences).

SDS-PAGE and Gelatin Zymography

Bovine type B gelatin (Sigma) was impregnated into a standard 10% PAGE resolving gel mixture (4% stacking) at a final concentration of 1 mg/ml. Where indicated, endothelial cells transfected with DNAzyme were co-transfected with 10 μg of a c-Jun expression vector. Equal amounts of protein were loaded and electrophoresis was performed at 4° C. Gels were then soaked in 2.5% Triton X-100 (Sigma) and incubated in substrate buffer (50 mM Tris HCl, pH 7.6, 10 mM $CaCl_2$, and 0.02% $NaN_3$) overnight at 37° C. The gels were stained for 1 h in 0.2% Coomassie Blue R-250 (Bio-Rad) in water, methanol and glacial acetic acid as 5:4:1, then gels were finally destained to reveal gelatinolytic activity and photographed.

Immunohistochemistry

Sections of formalin-fixed, paraffin-embedded human cutaneous malignant melanoma in paraffin were stained with rabbit anti-peptide polyclonal antibodies to c-Jun or CD31 or goat anti-peptide antibodies to MMP-2, as previously described[66]. Immunoreactivity was revealed following incubation of the sections with either biotinylated-secondary anti-rabbit or anti-goat antibody, as appropriate.

Rat Corneal Neovascularization Model

The corneas of 7 w.o. Sprague Dawley rats were implanted with 0.57 mm diameter nitrocellulose filter disks that had previously been soaked for at least 30 min in 30 µM $VEGF_{165}$ in 82 mM Tris-HCl (pH 6.9). DNAzyme (100 µg) or vehicle alone was subsequently administered into the conjunctiva adjacent to the disk following implantation. Corneas were carefully removed prior to quantitation of the (i) area of occupied by neovascularization (calculated as 0.2×π×clock hours occupied by vascularization×maximum vessel length) and (ii) the number of vessels growing within the cornea 5 d after implantation.

Tumor Xenograft Mouse Models

B16F10 cells ($5 \times 10^4$) were injected s.c. into the dorsal midback region of C57BL/J6 (6 w.o.) mice with 750 µg of DNAzyme in 200 µl of matrigel. Body weight and tumour dimensions were measured digitally at the times indicated in the figure. Tumor volumes (mm³) were determined using the equation length×width×height×0.52.

Results

Figure 2A:
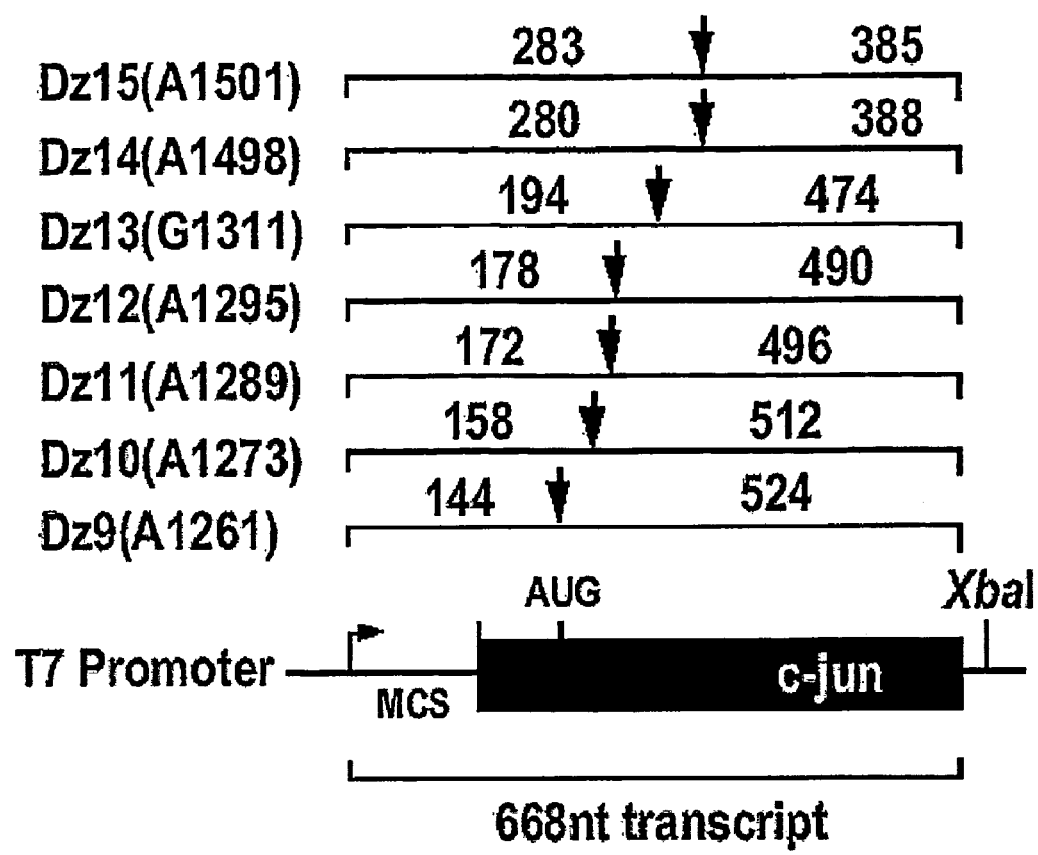
FIG. 2. Cleavage of in vitro transcribed c-Jun RNA and inhibition of c-Jun induction by c-Jun DNAzymes. a, Representation of DNAzyme cleavage sites (arrows) in c-Jun RNA and sizes of expected products. The specific purine hosting the 3' cleavage is indicated for each candidate DNAzyme. Numbering is based on the human c-Jun complete cds (Accession J04111, NID g186624). The expression vector used for the T7 RNA polymerase-dependent generation of c-Jun RNA is indicated. b, Integrity analysis of DNAzyme (34 nt) (upper panel) and 668 nt c-Jun RNA (middle panel) and panning or nucleolytic activity of candidate DNAzymes after 1 h at 37° C. (lower panel). DNAzyme integrity was determined by 5'-end labelling with $\gamma^{32}$P-dATP and T4 RNA polymerase prior to resolution on 12% denaturing polyacrylamide gels. Transcript integrity was determined by random labelling with $\alpha^{32}$P-UTP and T7 polynucleotide kinase prior to resolution on 12% denaturing polyacrylamide gels. The figure shows the 668 nt transcript after the reaction was allowed to proceed for the times indicated. Subsequent experiments used the 30 min run-off. c, Time- and dose-dependence of Dz13 cleavage of c-Jun RNA. The 474 and 194 nt products are indicated. d, Western blot analysis for c-Jun protein. Extracts of smooth muscle cells (10 μg) transfected with 0.5 μM of DNAzyme (Dz13 or Dz13scr) were assessed for c-Jun immunoreactivity (39 kDa) using rabbit polyclonal anti-peptide antibodies (Santa Cruz Biotechnology). The Coomassie bluestain gel shows unbiased loading.
Figure 2B:
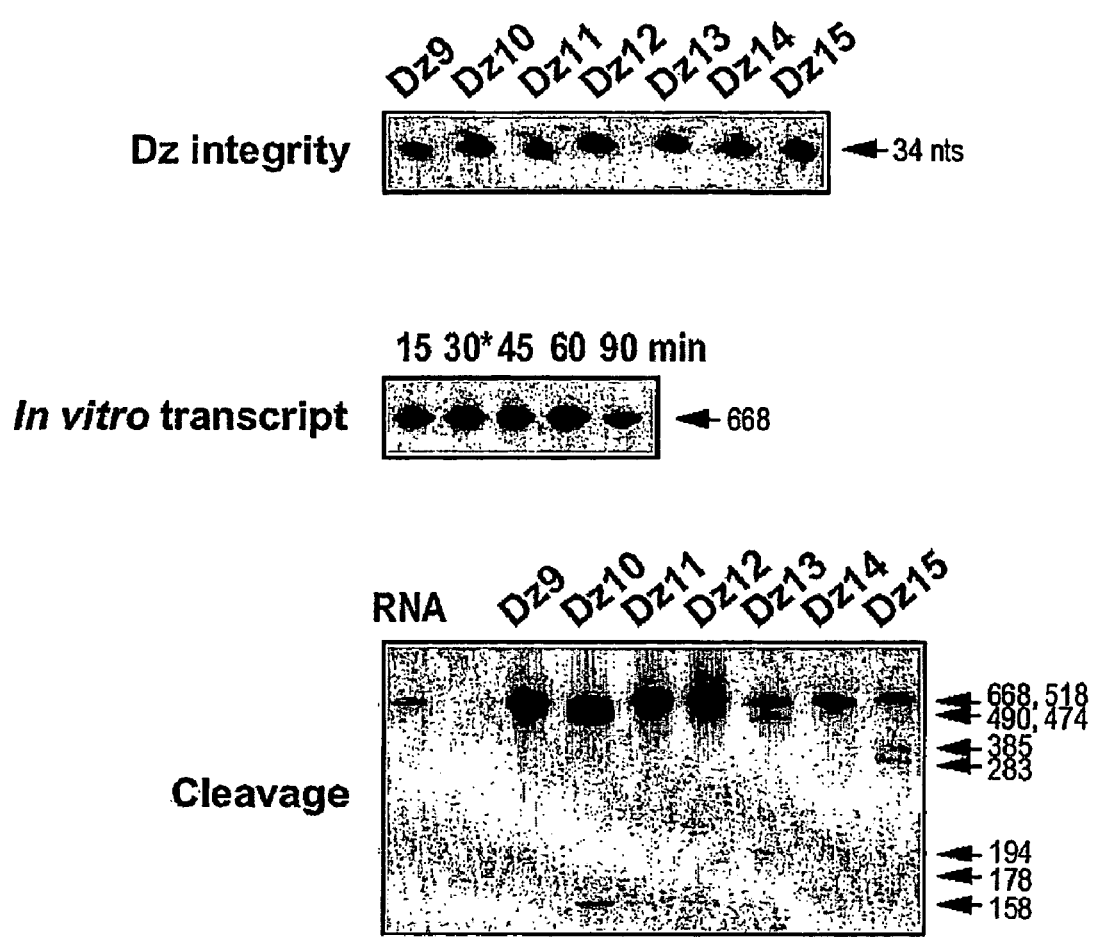
Figure 2D:
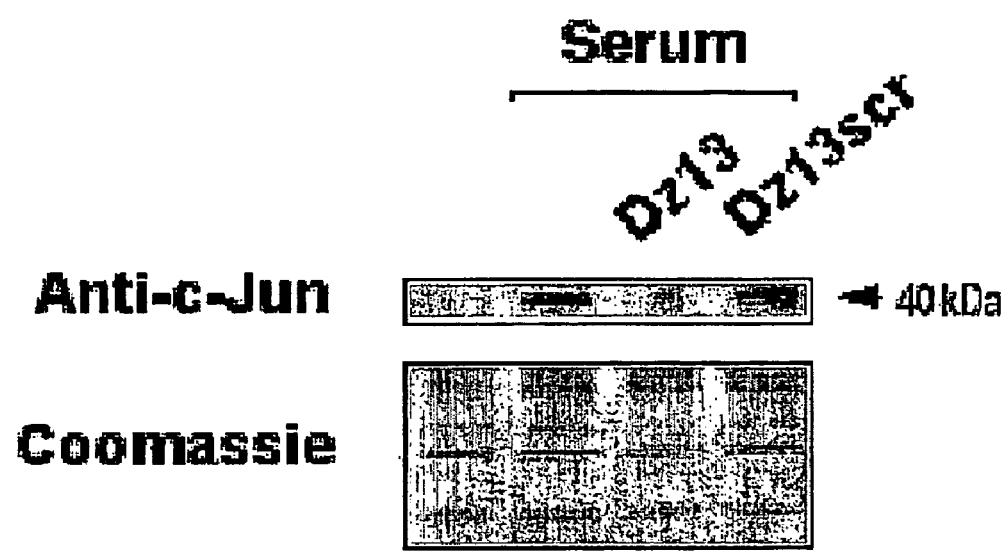

Dz13 Cleaves c-Jun RNA and Blocks Inducible c-Jun Expression in Vascular Smooth Muscle Cells Seven DNAzymes (FIG. 2A), bearing two nine nucleotide hybridising arms and a single 15 nt catalytic motif[27] targeting various regions of low free energy[31] were evaluated for their capacity to cleave $^{32}$P-labeled in vitro transcribed c-Jun RNA. The seven DNAzymes and c-Jun transcript were first resolved by denaturing electrophoresis to ensure structural integrity (FIG. 2B). The 668 nt c-Jun transcript was cleaved by DNAzymes Dz10, Dz12, Dz13, Dz14 and Dz15, but not by Dz9 and Dz11 within 1 h at 37° C. under physiological conditions (FIG. 2B). One of the active DNAzymes, Dz13, targeting the $G^{1311}U$ junction (where the translational start site in human c-Jun mRNA is located at $A^{1261}UG$), cleaved the transcript within 15 min in both a time-dependent (FIG. 2C, upper panel) and dose-dependent (FIG. 2C, lower panel) manner, generating 474 and 194 nt products. DNAzyme Dz13scr, in which the hybridizing arms of Dz13 were scrambled without disturbing the integrity of the catalytic domain, failed to cleave the substrate at any time or stoichiometric ratio (FIG. 2C). To demonstrate Dz13 inhibition of endogenous c-Jun in primary human arterial smooth muscle cells, we performed Western blot analysis on growth-quiescent cells previously transfected with 0.5 µM Dz13 or Dz13scr and exposed to serum for 2 h at 37° C. Serum-inducible c-Jun immunoreactivity (39 kDa) was strongly inhibited by Dz13, whereas its scrambled counterpart had no effect (FIG. 2D).

All of the c-Jun DNAzymes screened targeted regions in the mRNA likely to be exposed in solution, based on a Zukerian prediction of regions of low free energy in the mRNA, and preference for the 5' end of the mRNA, where the translational apparatus attaches and moves along the chain. The present study shows that Zuker analysis does not guarantee the efficacy of any given DNAzyme in intact cells, since only some, but not all the DNAzyme sequences that cleave in vitro transcribed c-Jun mRNA could actually inhibit cell proliferation. This may be due (although not confined) to differences in conformation and site accessibility between in vitro transcribed mRNA and endogenous mRNA, DNAzyme transfection efficiency, the concentration of ions and other DNAzyme cofactors in the local cellular millieu, and the possible existence of DNA-binding proteins (such as growth factors, signalling molecules, etc) having unintended preference for certain nucleotide sequences thereby reducing the amount of bioavailable DNAzyme.

The inability of the Zuker analysis to accurately predict DNAzyme efficiency does not hinder the design of effective DNAzyme. Once a particular target is selected, eg c-Jun it is a routine task to design and test a range of DNAzymes which target the particular mRNA, as shown in FIG. 2.

Dz13 Blocks Vascular Smooth Muscle Cell Proliferation

Figure 3B:
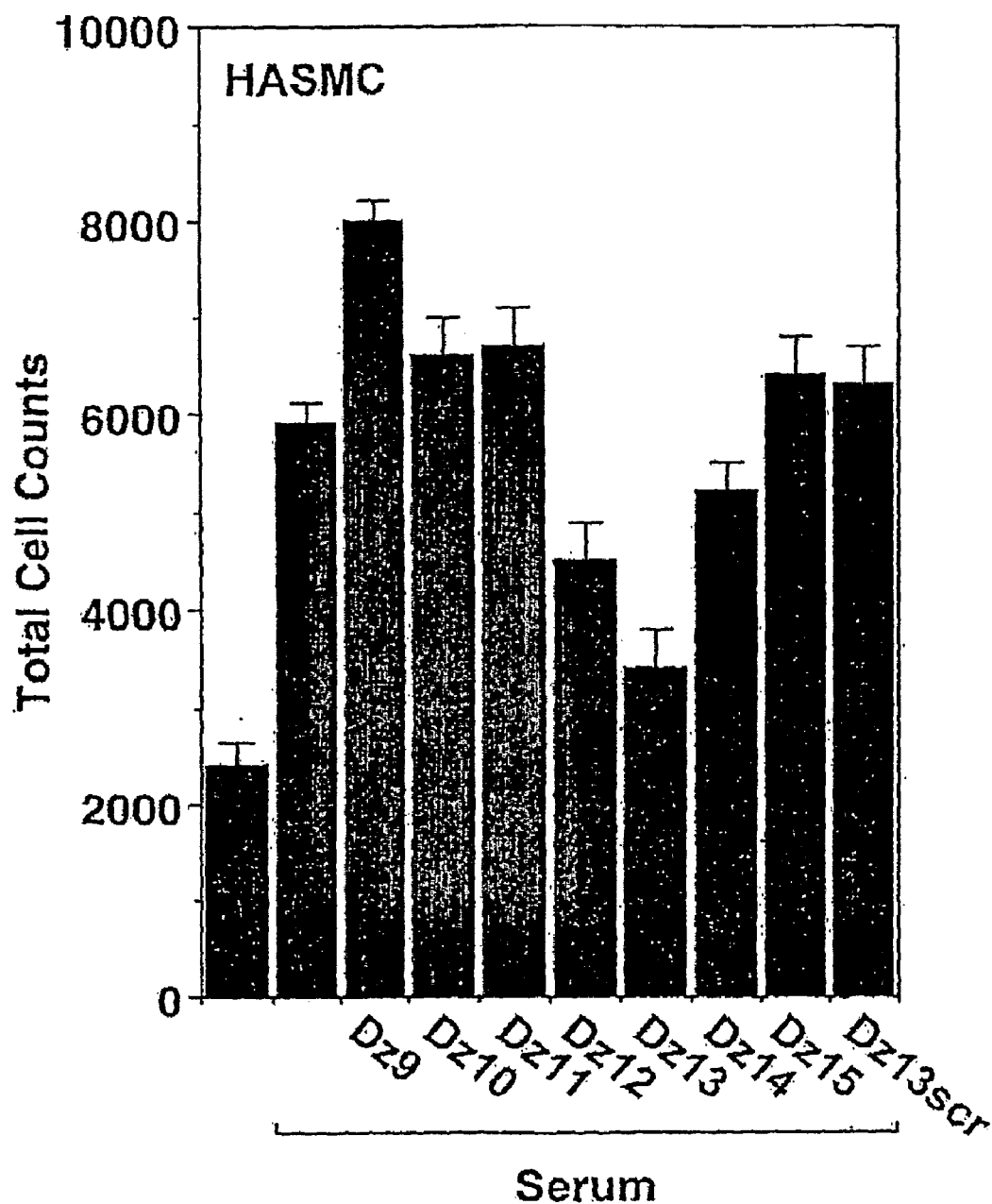
FIG. 3. c-Jun DNAzyme inhibition of smooth muscle cell proliferation. a, Schematic representation of c-Jun DNAzyme Dz13 and target site ($G^{1311}T$) in human c-Jun mRNA (upper panel), comparison of Dz13 target site in human, porcine and rat c-Jun mRNA (middle panel), and comparison of As13 and Dz13 (lower panel). The translational start site of human c-Jun mRNA is located at $A^{1261}TG$. (SEQ ID NOS:13, 22, 13, 19, 20, 21, 22). b, Effect of c-Jun DNAzymes (0.5 µM) on serum-inducible primary human smooth muscle cell (HASMC) proliferation inhibited by Dz13. Sequence of Dz13scr is 5'-GCG ACG TGA GGC TAG CTA CAA CGA GTG GAG GAG X-3' (SEQ ID NO:2), where X is a 3'-3'-linked inverted T. c, Serum-inducible porcine smooth muscle cell proliferation (PASMC) inhibited by 0.5 µM of Dz13. d, Human smooth muscle cell proliferation is inhibited by Dz13 and As13 in a dose-dependent manner. The concentrations of DNAzyme (0.1-0.4 µM) are indicated in the figure. The sequence of As13scr is 5'-GCG ACG TGA C GTG GAG GAG X-3', where X is a 3'3'-linked inverted T (SEQ ID NO:3).
Figure 3C:
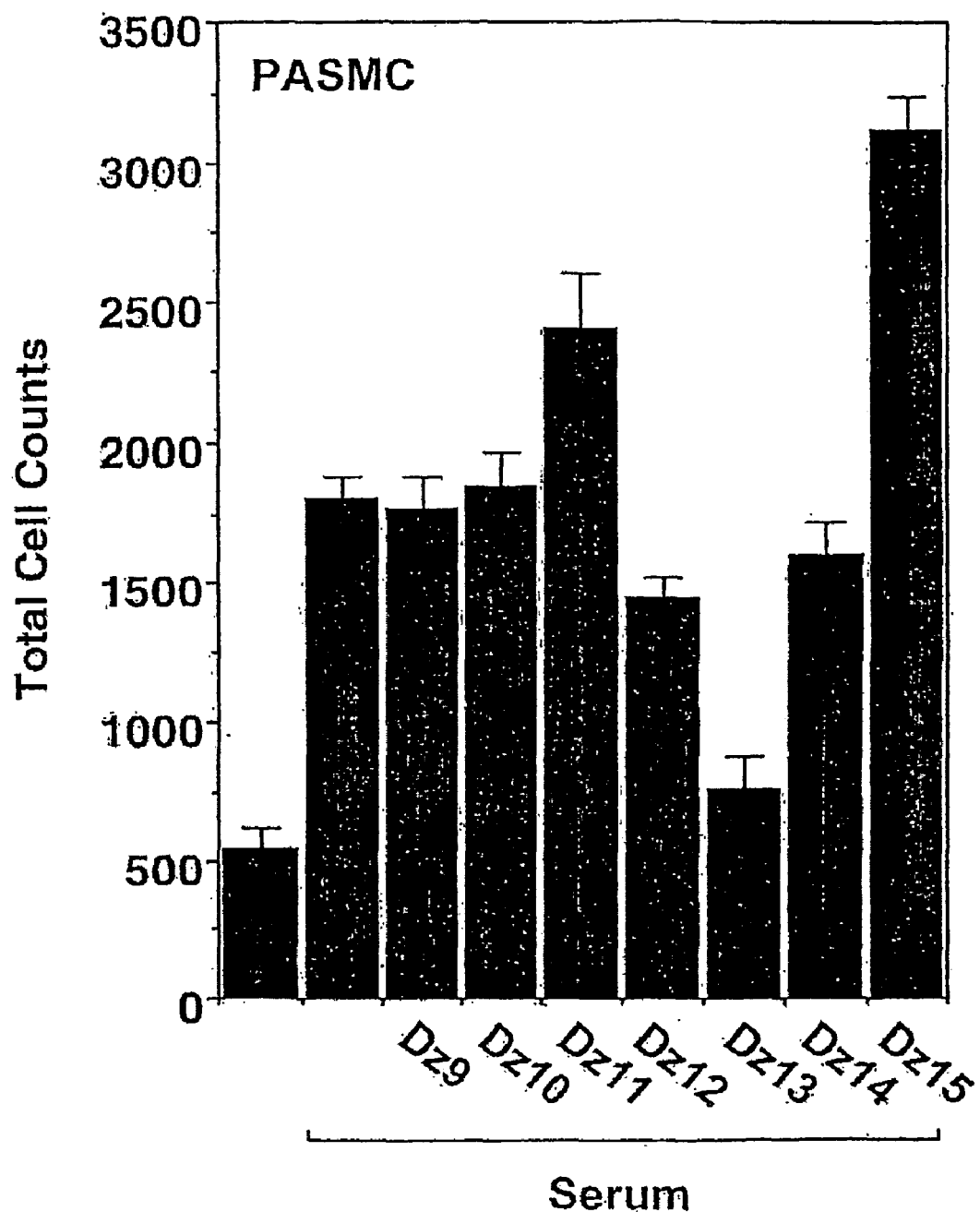
Figure 3D:
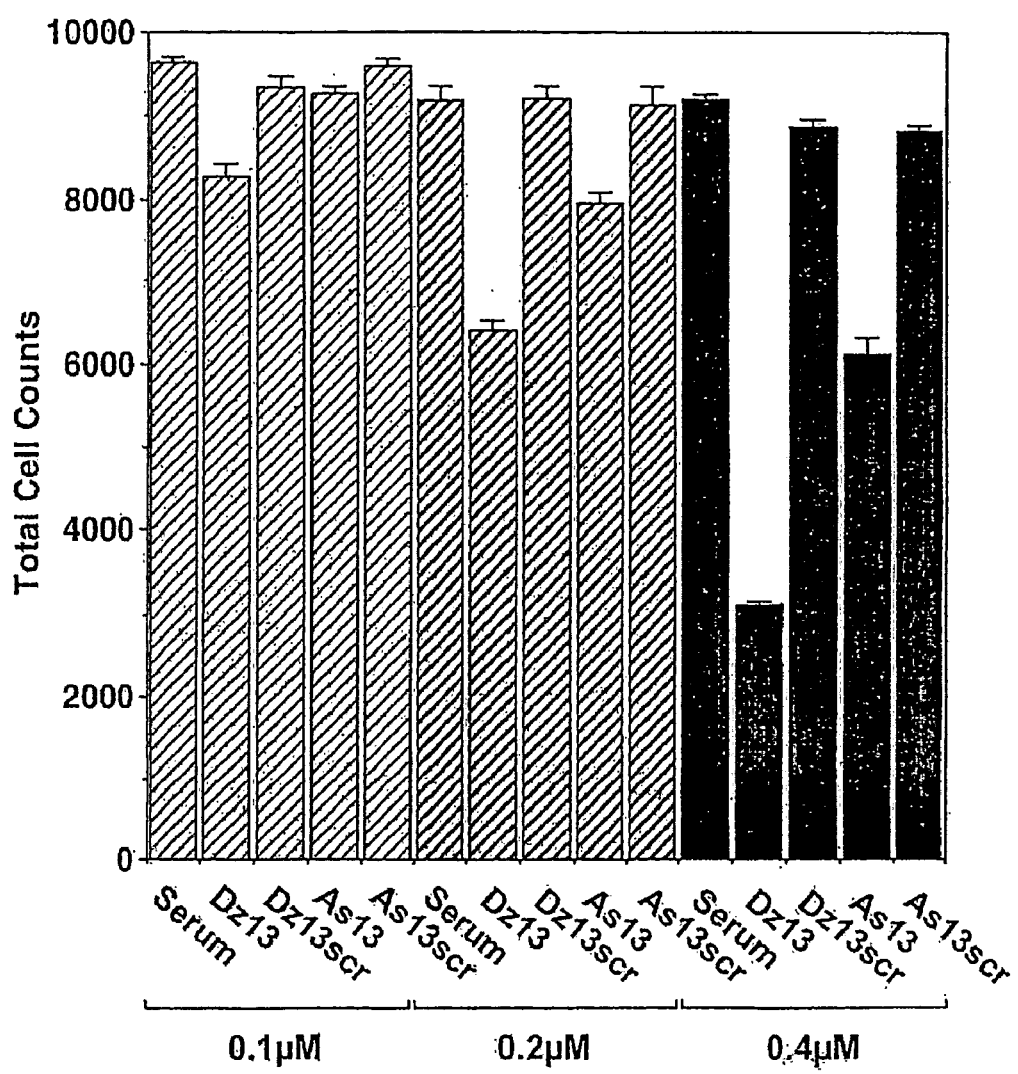

We next determined the influence of Dz13 and the panel of c-Jun DNAzymes on the growth of primary vascular smooth muscle cells derived from human and porcine arteries. The Dz13 target site in c-Jun RNA is conserved between human, pig and rat except for a single C nt at position 1319 which is an A in pig and rat c-Jun RNA (FIG. 3A, upper and middle panels). DNAzyme catalytic efficiency is largely unaffected by substitution of a single pyrimidine nt in the substrate with a purine[32], as in this case. Dz13 (0.5 µM) completely blocked serum-inducible proliferation in both cell types (FIGS. 3B & C) and was the most potent of the entire DNAzyme panel. Dz13 inhibition was dose-dependent and detectable at concentrations as low as 100 nM (FIG. 3D). In contrast, Dz13scr failed to inhibit smooth muscle cell proliferation (FIG. 3B), consistent with its inability to affect serum-inducible c-Jun protein (FIG. 2D). Surprisingly, some DNAzymes (Dz9, Dz11, Dz15) stimulated proliferation beyond the effect of serum alone (FIGS. 3B & C). Additionally, Dz10, which cleaved the c-Jun transcript as effectively as Dz13 (FIG. 2B) failed to modulate smooth muscle cell proliferation in either cell type, unlike Dz13 (FIGS. 3B & C). To demonstrate greater potency of the c-Jun DNAzyme compared to its exact antisense oligonucleotide counterpart, we generated As13 which, like Dz13, comprises a phosphodiester backbone and a 3'-3' linked inverted T, but has no catalytic core (FIG. 3A). As13 produced dose-dependent inhibition, however, Dz13 was twice as potent an inhibitor (FIG. 3D).

Figure 4:
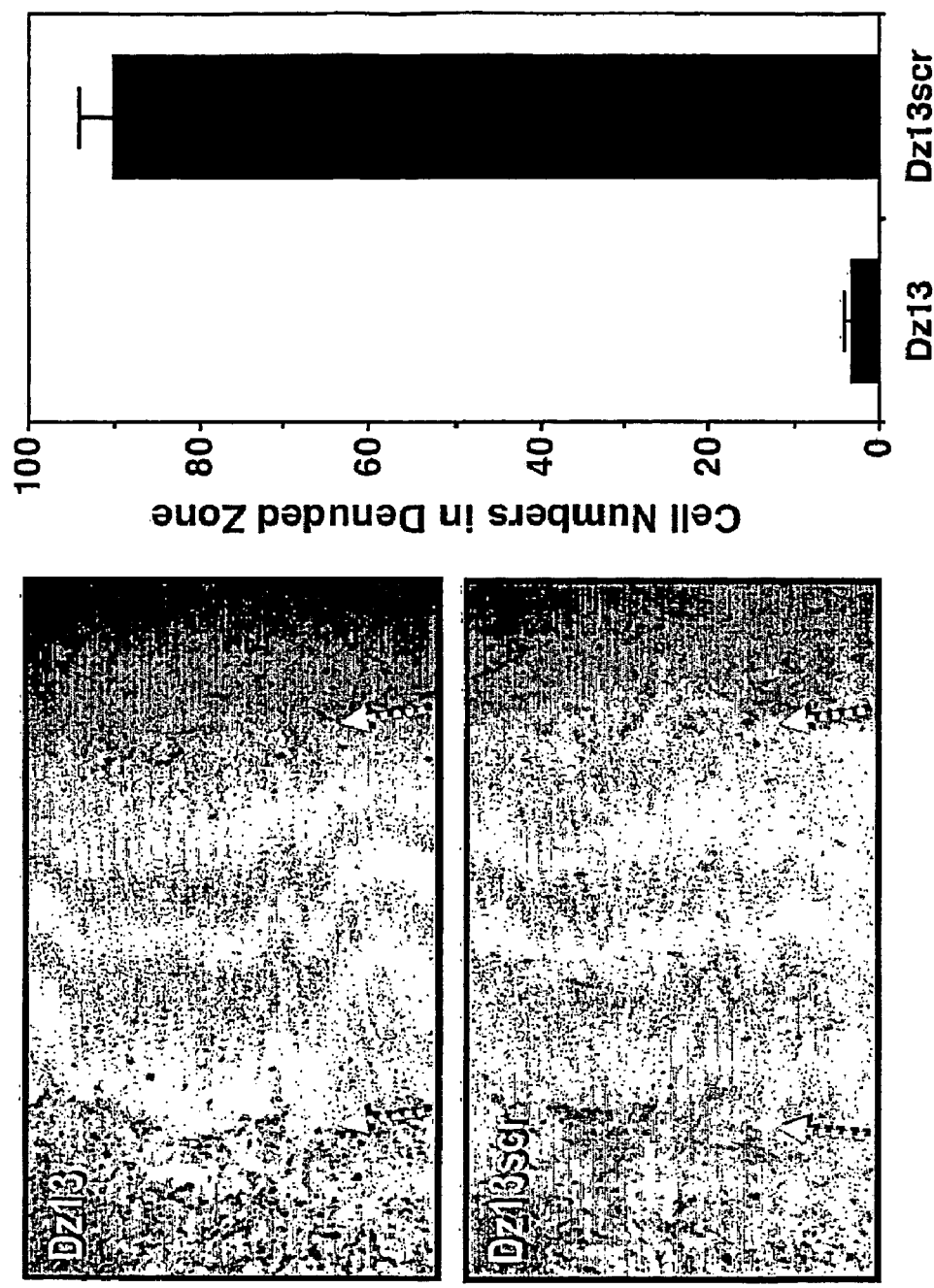
FIG. 4. c-Jun DNAzyme inhibition of smooth muscle cell repair. Smooth muscle cell regrowth in the denuded zone three days after scraping and transfection with 0.5 µM of Dz13 or Dz13scr. The cells were fixed and stained with hematoxylin and eosin prior to micrography.
Figure 5A:
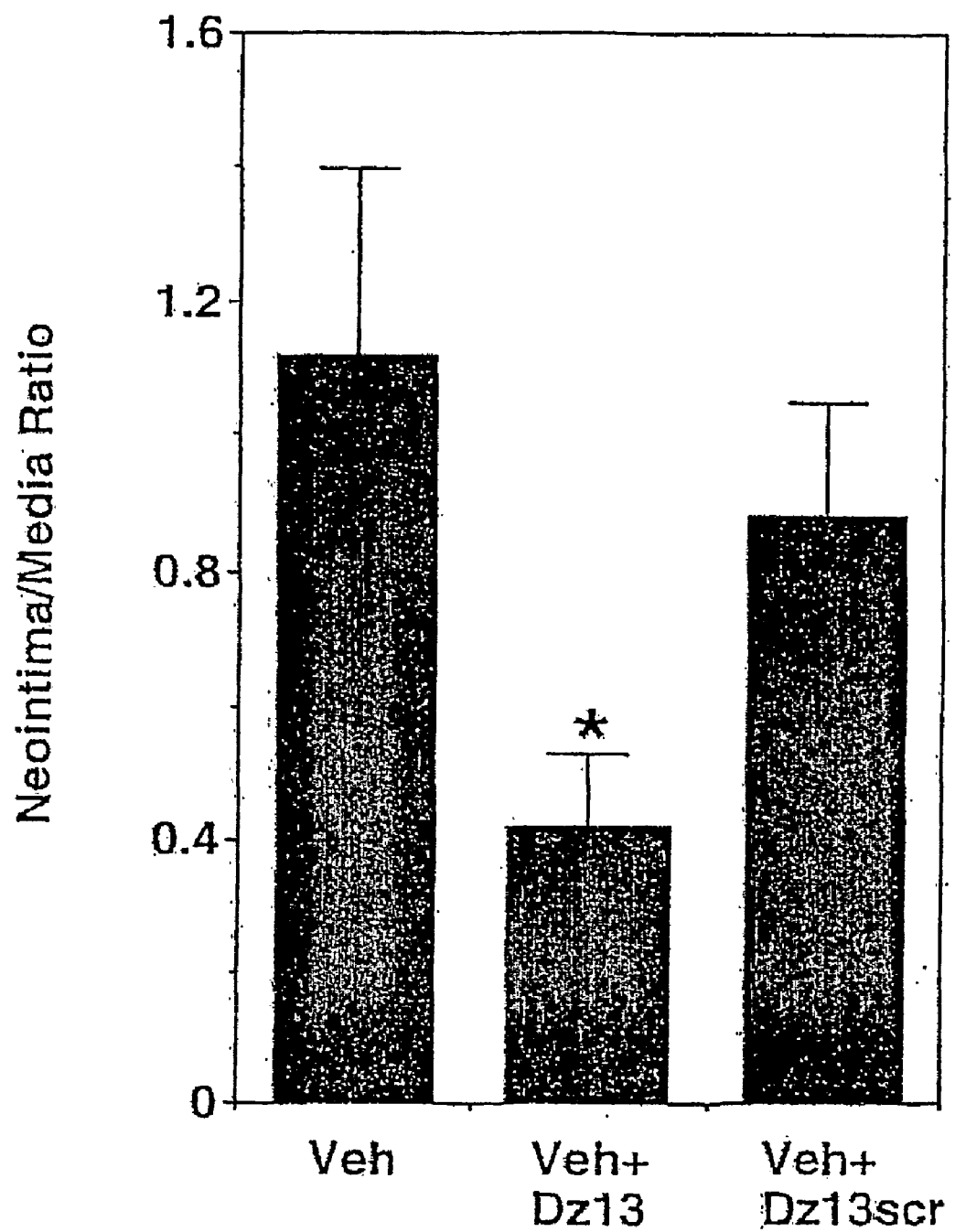
FIG. 5. Blockade of neointimal thickening in rat common carotid arteries. a, Neointima/media ratios for each group (vehicle alone, vehicle containing Dz13, vehicle containing Dz13scr) 21d after injury. * indicates P<0.05 compared with vehicle and vehicle containing Dz13scr groups using Student's t-test. The vehicle and vehicle containing Dz13scr groups were not statistically different. b, Representative cross-sections stained with haematoxylin-eosin. N and single line denotes neointima, M and triple line denotes media, arrow denotes preinjured intima. Thrombosis was occasionally observed and not confined to any particular group. c, Immunoperoxidase staining for c-Jun protein six hours after arterial injury. d, Immunoperoxidase staining for Sp1 six hours after arterial injury. DNAzyme in vehicle (FuGENE6, $MgCl_2$, PBS, pH 7.4) was applied to the carotid in Pluronic gel (BASF) at the time of injury. Three weeks subsequently the arteries were perfusion-fixed and 5 µm sections taken for immunohistochemical and morphometric analysis.
Figure 5B:
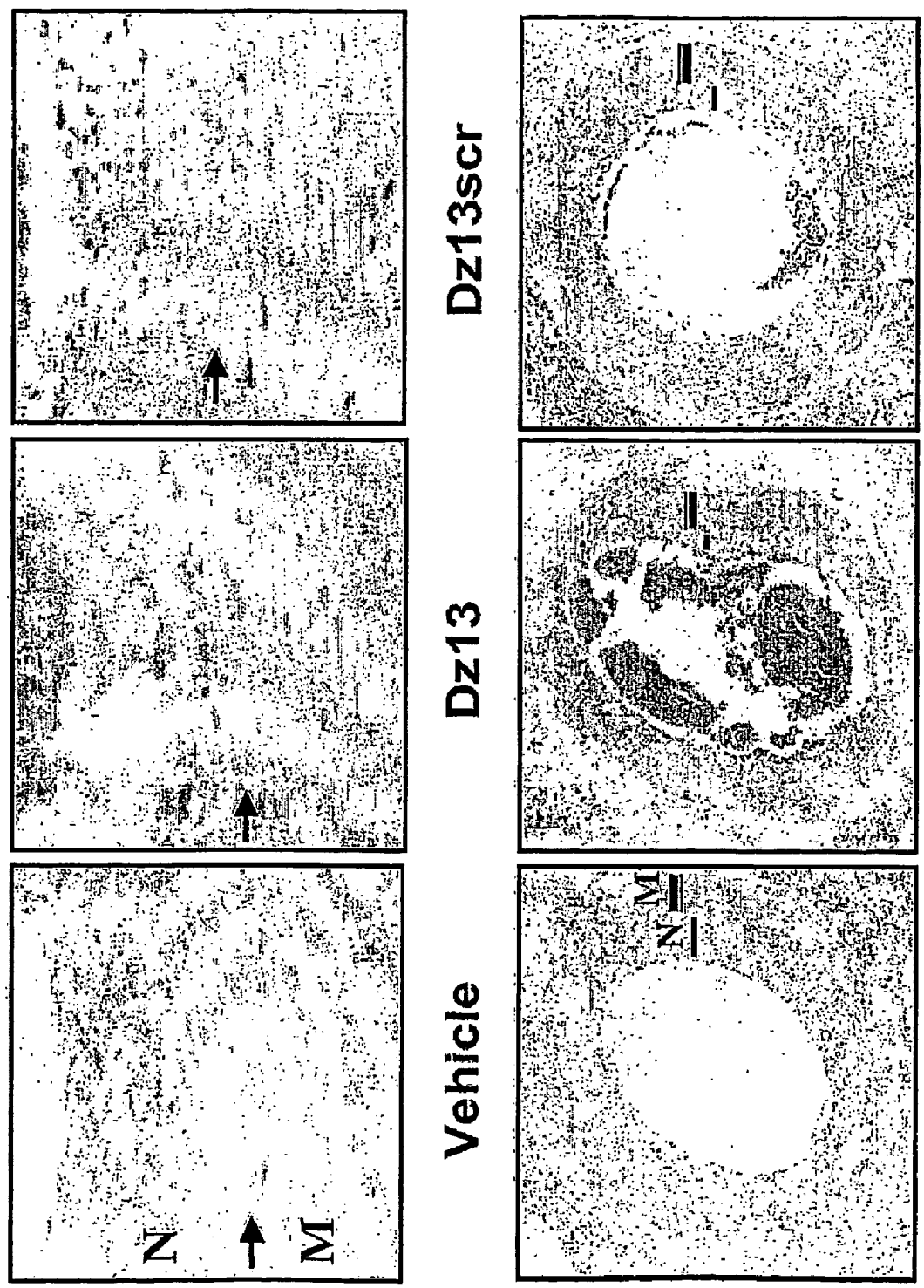
Figure 5C:
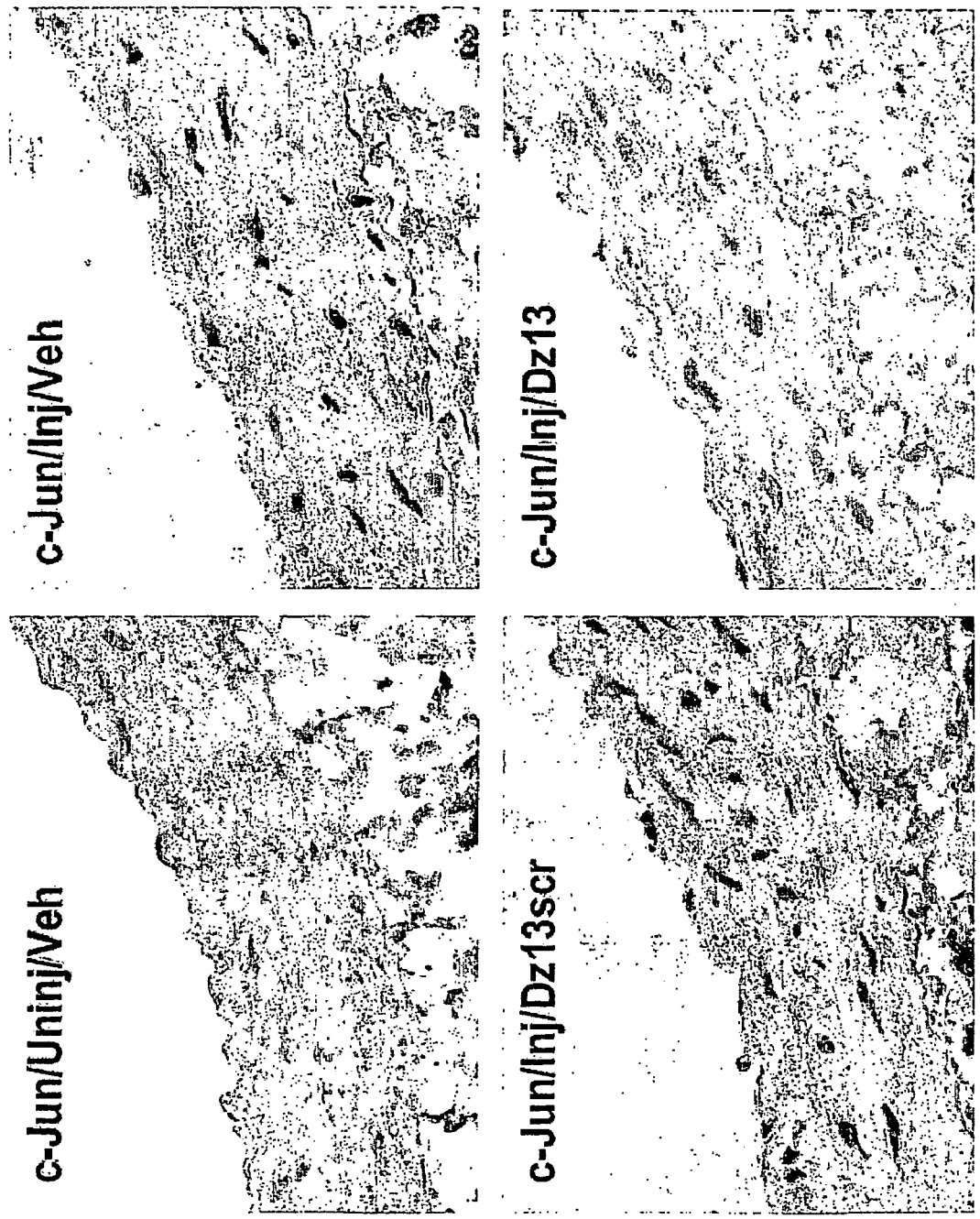
Figure 5D:
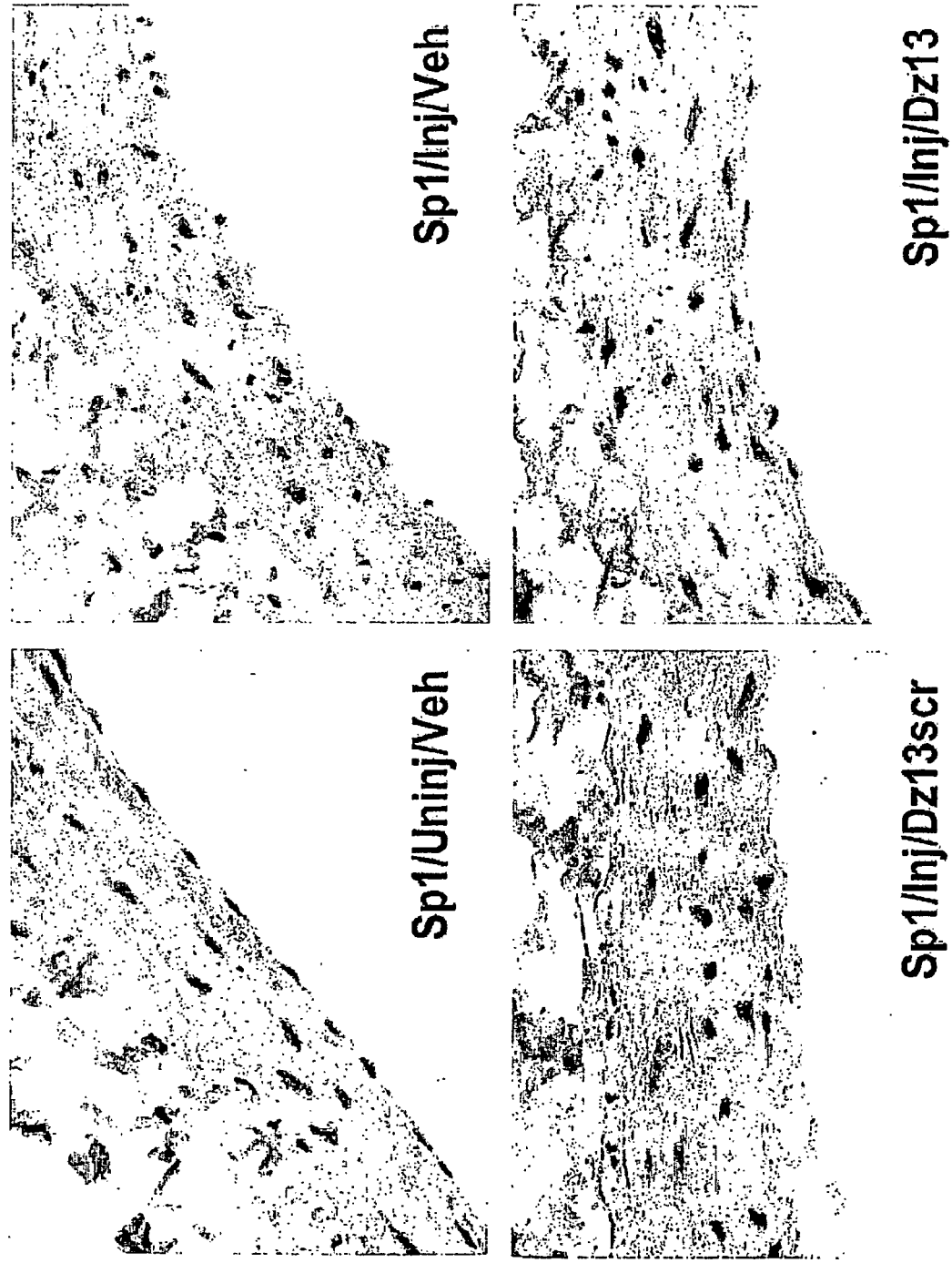

Dz13 Inhibits Vascular Smooth Muscle Cell Repair After Injury in vitro and Intimal Thickening in Rat Carotid Arteries Smooth muscle cell regrowth at the wound edge following mechanical scraping in an in vitro model[33] was abolished by the presence of 0.5 µM Dz13 (FIG. 4), whereas repair in the presence of Dz13scr was not different from wells without oligonucleotide (FIG. 4). Since smooth muscle cell proliferation and repair are processes negatively regulated by Dz13, we next determined whether the c-Jun DNAzyme could influence intimal thickening after ligation injury to rat carotid arteries. The arterial response to injury in rats has provided critical insights on the cellular and molecular events underlying the formation of lesions[34]. Neointima formation three weeks after injury and local administration of Dz13scr was not significantly different from that observed in the vehicle alone group (FIGS. 5A & B). However, intimal thickening was suppressed by Dz13 of the order of 60% (FIGS. 5A & B). Immunohistochemnical analysis revealed that Dz13 blocked the induction of c-Jun immunoreactivity in the smooth muscle cells of the arterial media, whereas Dz13scr had no effect (FIG. 5C). In contrast, neither DNAzyme had any influence on levels of Sp1 (FIG. 5C). Together, these data demonstrate a crucial role for c-Jun in smooth muscle cell proliferation, wound repair and neointima formation.

Arterial neointima formation has previously been inhibited by phosphorothioate-linked antisense oligonucleotides directed against certain transcription factors and cell cycle regulatory molecules, including the p65 subunit of NFκ-B[35], c-myb[36], c-myc[37], and cdc2 kinase/proliferating-cell nuclear antigen (PCNA)[38]. By directly comparing a phosphodiester-linked DNAzyme with an antisense oligonucleotide targeting the same sequence in c-Jun mRNA, each of identical arm length and bearing a 3'-3'-inverted T, this study demonstrates superior inhibition by the former molecule at any given concentration. c-Jun DNAzymes could serve as new, more potent gene-specific tools to probe the precise function(s) of this transcription factor in a wide array of fundamental cellular processes.

Since c-Jun has been implicated in the pathogenesis of other fibroproliferative-inflammatory processes, such as arthritis[39], neoplasia[40], acute lung injury[41], scarring[42], UV-induced corneal damage[43] and osteoperosis[44], DNAzymes targeting c-Jun and other key regulatory molecules[33] may, alone or in combination, show promise in efforts to inhibit proliferative vascular disease and other pathological processes.

Involvement of c-Jun in Angiogenesis

Microvascular endothelial cells have become an important target in cancer therapy, since angiogenesis, the formation of new blood vessels, is an absolute requirement for tumor cell growth and metastasis. It is also a key process in the pathogenesis of other common human diseases such as arthritis and diabetic retinopathy. Angiogenesis is a complex processes involving endothelial cell proliferation, migration, and microtubule formation.

Dz13 Inhibits c-Jun Protein Expression, DNA-binding Activity, Migration, Proliferation and Tubule Formation by Microvascular Endothelial Cells.

c-Jun, unlike the zinc finger transcription factor Sp1, is poorly expressed in growth-quiescent human microvascular endothelial cells but is induced within 2 h of exposure to serum. Dz13, a DNAzyme targeting the $G^{1311}U$ junction in the coding region of human c-Jun mRNA, blocked c-Jun protein expression at a concentration of 0.4 µM. In contrast, c-Jun activation was not affected by the same concentration of Dz13scr, which bears the active catalytic domain of Dz13 flanked by scrambled 9+9 nt arms but retaining the 3'-3'-linked inverted T that confers stability[33]. As13, the antisense oligonucleotide counterpart of Dz13 (including the 3' inverted T) lacking the catalytic domain of the DNAzyme, also inhibited inducible c-Jun protein expression, whereas the scrambled version, As13scr, had no effect. Sp1 levels were not changed by any of the molecules tested (data not shown).

A faint nucleoprotein complex was produced following electrophoretic mobility shift analysis using a $^{32}$P-labeled oligonucleotide bearing a consensus binding element for c-Jun and nuclear extracts from quiescent microvascular endothelial cells. The intensity of this complex increased within 2 h of exposure to serum. Inducible DNA-binding activity was abolished either by Dz13 (0.4 µM) and preincubation of the extracts with c-Jun antibodies (2 µg), whereas Dz13scr had no effect (data not shown).

The preceding findings revealed the capacity of c-Jun DNAzymes to block c-Jun protein expression and DNA-binding activity in a sequence-specific manner. We next determined the effect of these molecules on endothelial tubule formation, proliferation and migration.

Figure 6:
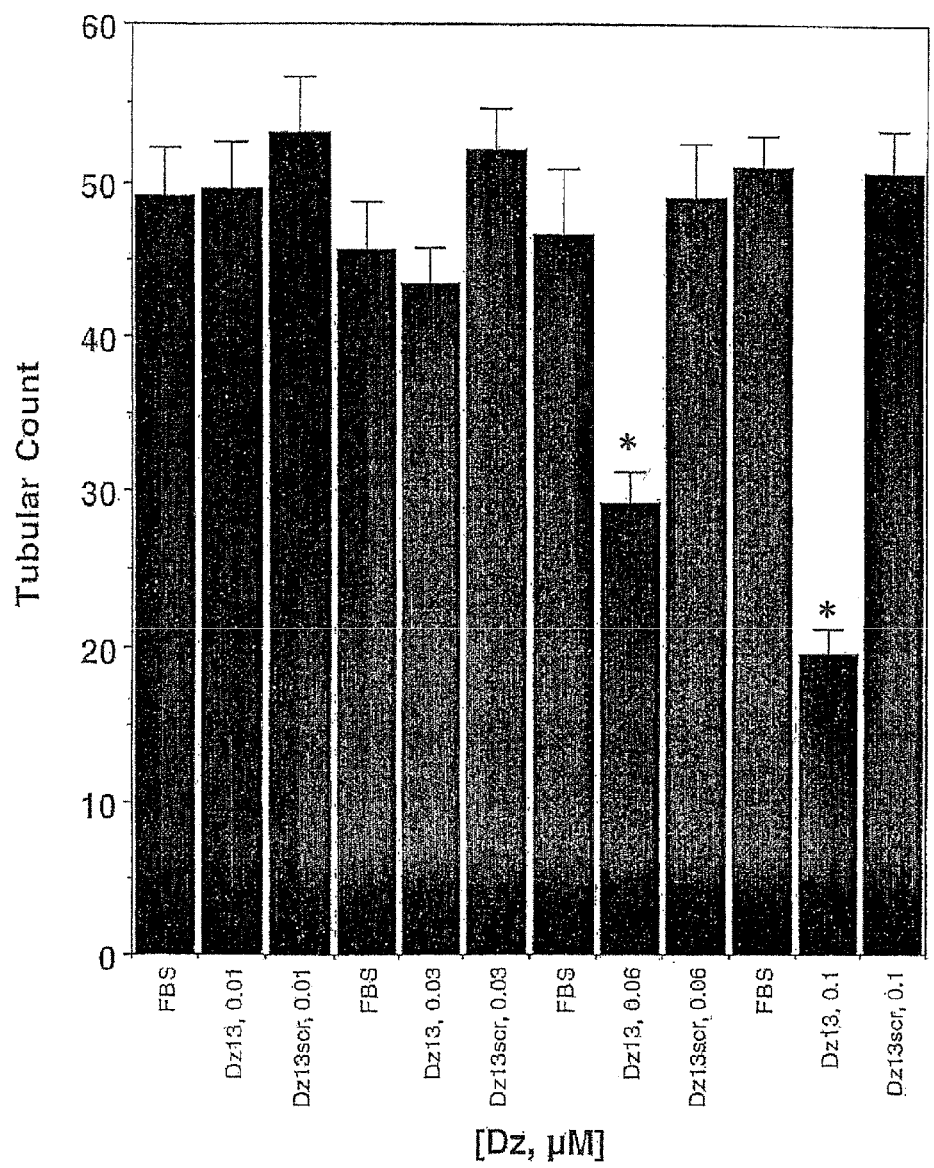
FIG. 6. Dz13 inhibits microvascular endothelial microtubule formation on reconstituted basement membranes. HMEC-1 cells, transfected previously with the indicated concentrations of Dz13 and Dz13scr, were plated into 96 wps containing matrigel and tubule formation was quantitated after 8 h. Asterisk indicates p<0.05 by Student's t-test relative to control. Western and EMSA revealed that Dz13 inhibits c-Jun expression and DNA-binding activity in microvascular endothelial cells (data not shown). (FBS denotes foetal bovine serum)

Endothelial cells spontaneously form a three-dimensional microtubular capillary-like network on matrigel. Endothelial cells align on the matrigel and form cords within hours of plating. Dz13 blocked tubulogenesis in a dose-dependent manner (FIG. 6). This process was unchanged by the presence of Dz13scr (FIG. 6). These findings demonstrate that c-Jun is required for endothelial network formation. The target site of Dz13 and other DNAzymes are shown in FIG. 7B.

Figure 8A:
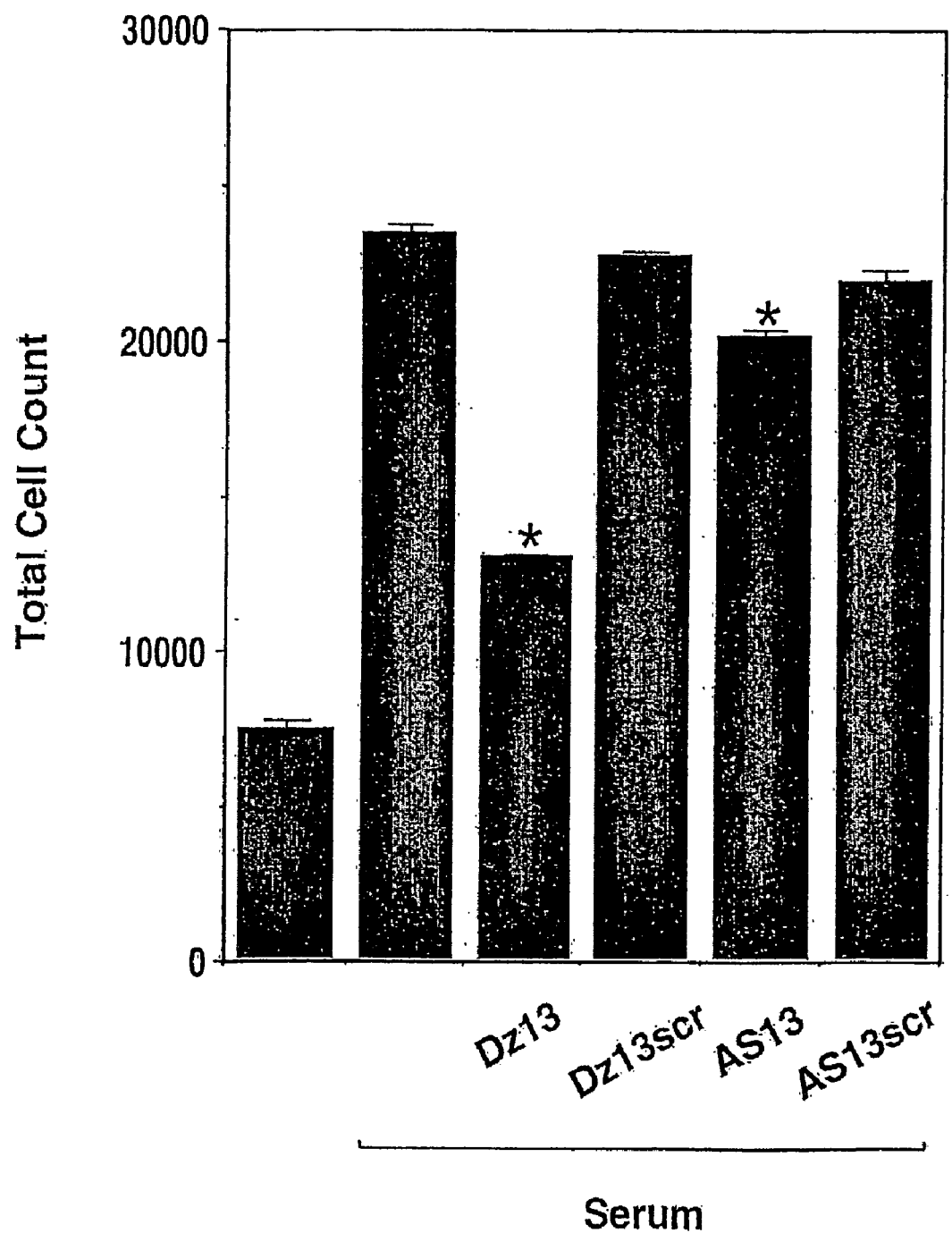
FIG. 8. Dz13 inhibits microvascular endothelial cell proliferation. A, Growth-quiescent HMEC-1 cells pre-treated with DNAzyme (0.2 µM) were exposed to serum and total cell counts were determined after 3 days using a Coulter counter. B, Dz13 inhibition of microvascular endothelial cell proliferation is dose-dependent. C, Effect of Dz13 variants (shorter and longer arm length) on proliferation. Sequences of Dz13 (11+11), Dz13(10+10) and Dz13(8+8) are 5'-GA CGG GAG GAA ggc tag cta caa cga GAG GCG TTG AG-Ti-3' (SEQ ID NO:7), 5'-A CGG GAG GAA ggc tag cta caa cga GAG GCG TTG A-Ti-3' (SEQ ID NO:8) and 5'-GG GAG GAA ggc tag cta caa cga GAG GCG TT-Ti-3' (SEQ ID NO:9), respectively. Sequences of Dz13(11+11)scr, Dz13(10+10)scr and Dz13 (8+8)scr are 5'-GA GCG ACG TGA ggc tag cta caa cga GTG GAG GAG AG-Ti-3' (SEQ ID NO:10), 5'-A GCG ACG TGA ggc tag cta caa cga GTG GAG GAG A-Ti-3' (SEQ ID NO:11) and 5'-CG ACG TGA ggc tag cta caa cga GTG GAG GA-Ti-3', respectively (SEQ ID NO:12). Ti is a 3'-3'-linked inverted T. Asterisk indicates p<0.05 by Student's t-test relate to control.
Figure 8B:
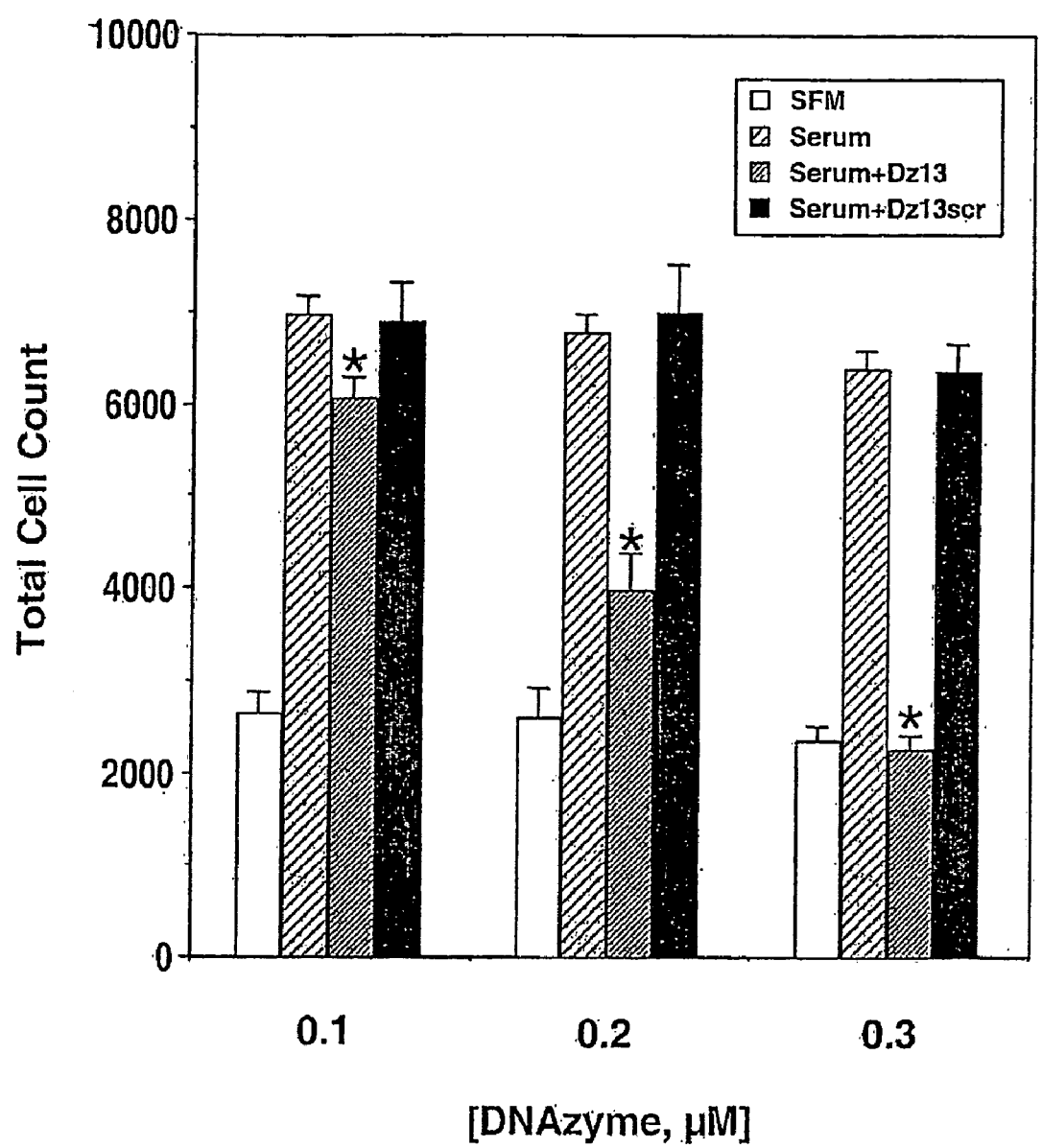

Endothelial cell growth in the presence of serum was inhibited by Dz13 (FIG. 8A) but not by Dz13scr (FIG. 8A). Dz13 inhibition was sequence-specific and dose-dependent maximal at 0.3 µM (FIG. 8B). As13 also attenuated endothelial proliferation (FIG. 8A), although with less potency than the c-Jun DNAzyme at the same concentration (FIG. 8A), consistent with the effect of these agents on the expression of c-Jun.

Figure 8C:
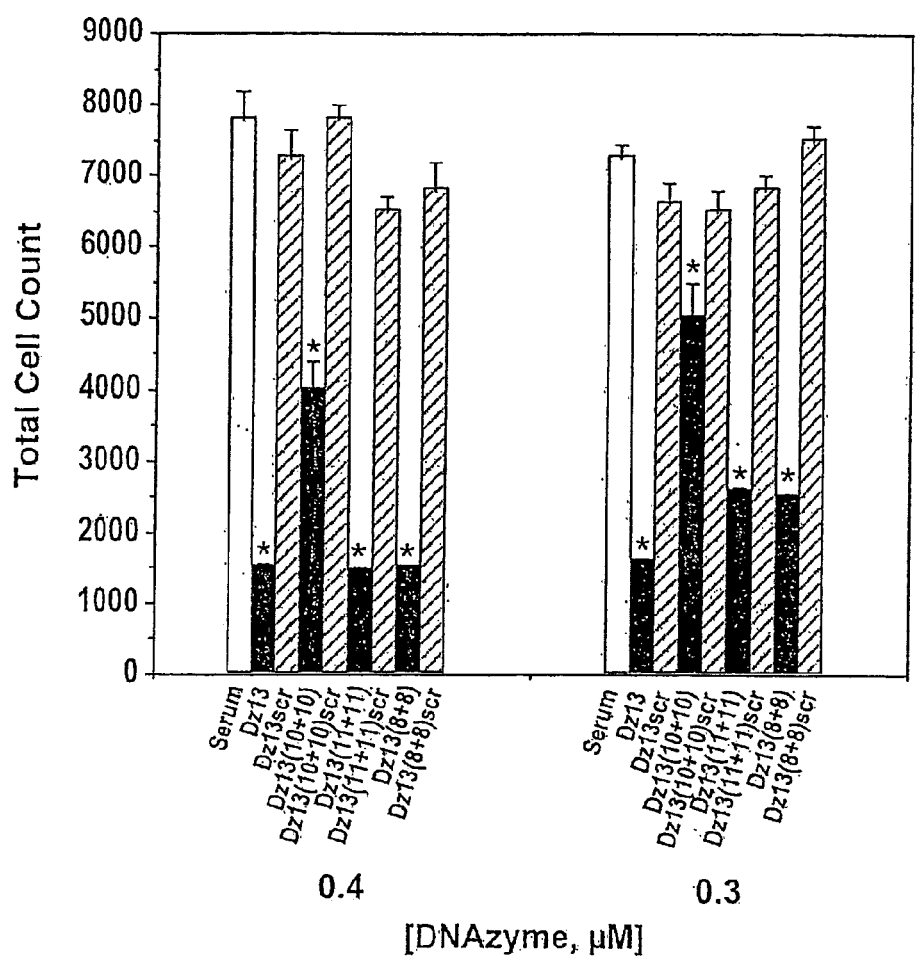

To determine effect of arm length on the biological activity of Dz13, bearing 9+9 nt arms, we synthesized a nested series of DNAzymes with 10+10, 11+11 and 8+8 nt arms (each with an 3' inverted T), together with their scrambled arm counterparts. At a concentration of 0.4 µM, Dz13(11+11) and Dz13(8+8) inhibited endothelial proliferation as effectively as native Dz13 (FIG. 8C). However, when these DNAzymes were used at a lower concentration (0.2 µM), it became apparent that Dz13(11+11) and Dz13(8×8) were less potent inhibitors of endothelial proliferation than Dz13 (FIG. 8C). Dz13 (10×10), in comparison to Dz13, Dz13(11×11) or Dz13(8×8), was a poor inhibitor.

Western blot analysis revealed that Dz13(11×11) and Dz13 (8×8), like Dz13, inhibited serum-inducible c-Jun expression, whereas-Dz13(10×10), Dz13(11×11)scr and Dz13(8×8)scr had little effect. Reprobing the stripped blot with antibodies to Sp1 revealed unaltered levels of this nuclear protein. In support of these data, Dz13(11×11) and Dz13(8×8), like Dz13, cleaved their 40 nt $^{32}$P-labeled synthetic RNA substrate in a time-dependent manner, whereas Dz13(10×10), Dz13(11×11)scr and Dz13(8×8)scr failed to cleave (data not shown).

Figure 9A:
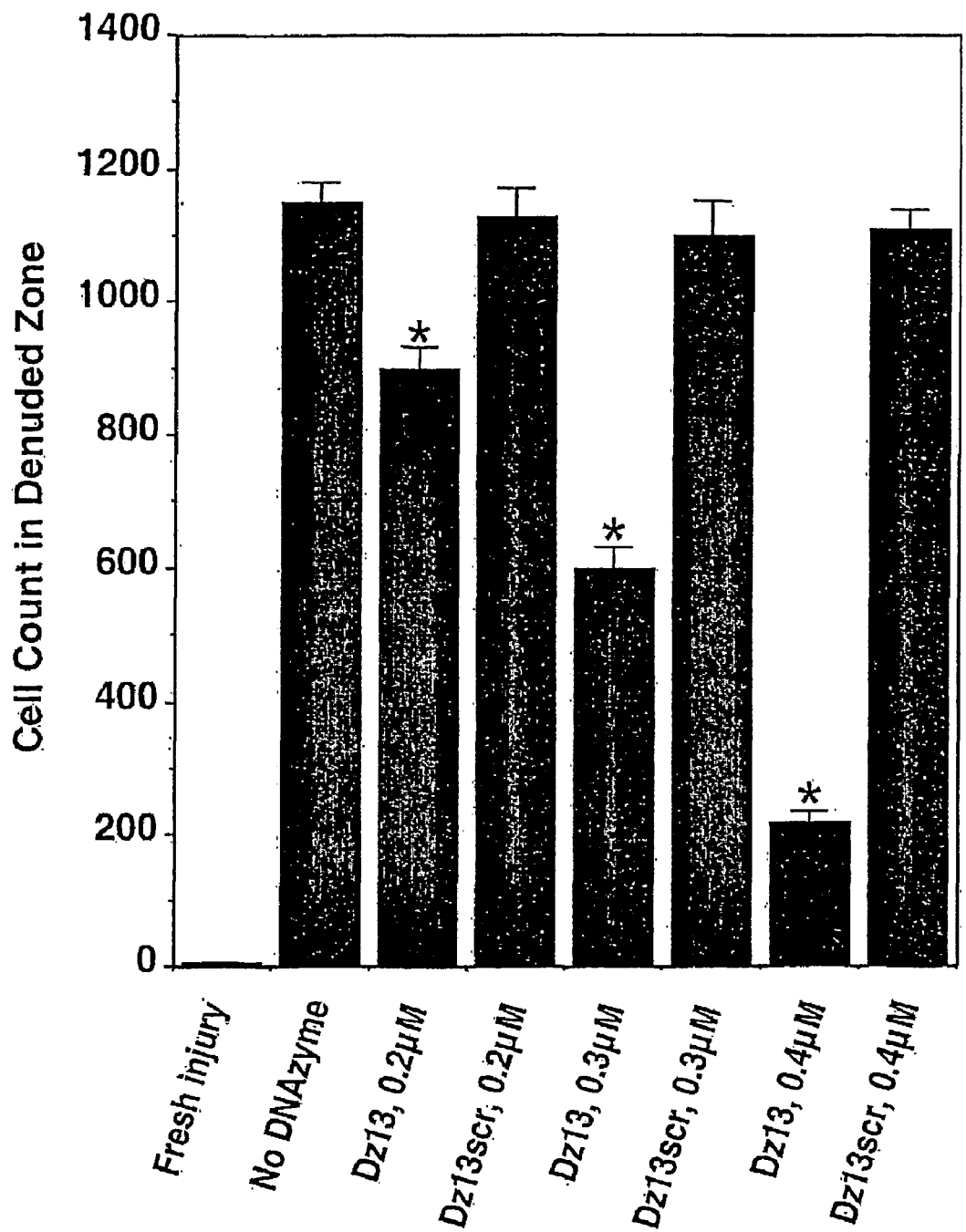
FIG. 9. Dz13 inhibits microvascular endothelial regrowth after scraping in vitro and migration in modified Boyden chambers. A, Growth-quiescent HMEC-1 cells pre-treated with DNAzyme (0.2, 0.3 or 0.4 µM) were scraped and the number of cells in the denuded zone was quantitated under microscopy. B, HMEC-1 were plated in modified Boyden chambers coated with matrigel or collagen type I (chemoattractant in lower chamber was FGF-2, 20 ng/ml) and the number of cells on the underside of the membrane was quantitated after 24 h. Asterisk indicates p<0.05 by Student's t-test relative to control.
Figure 9B:
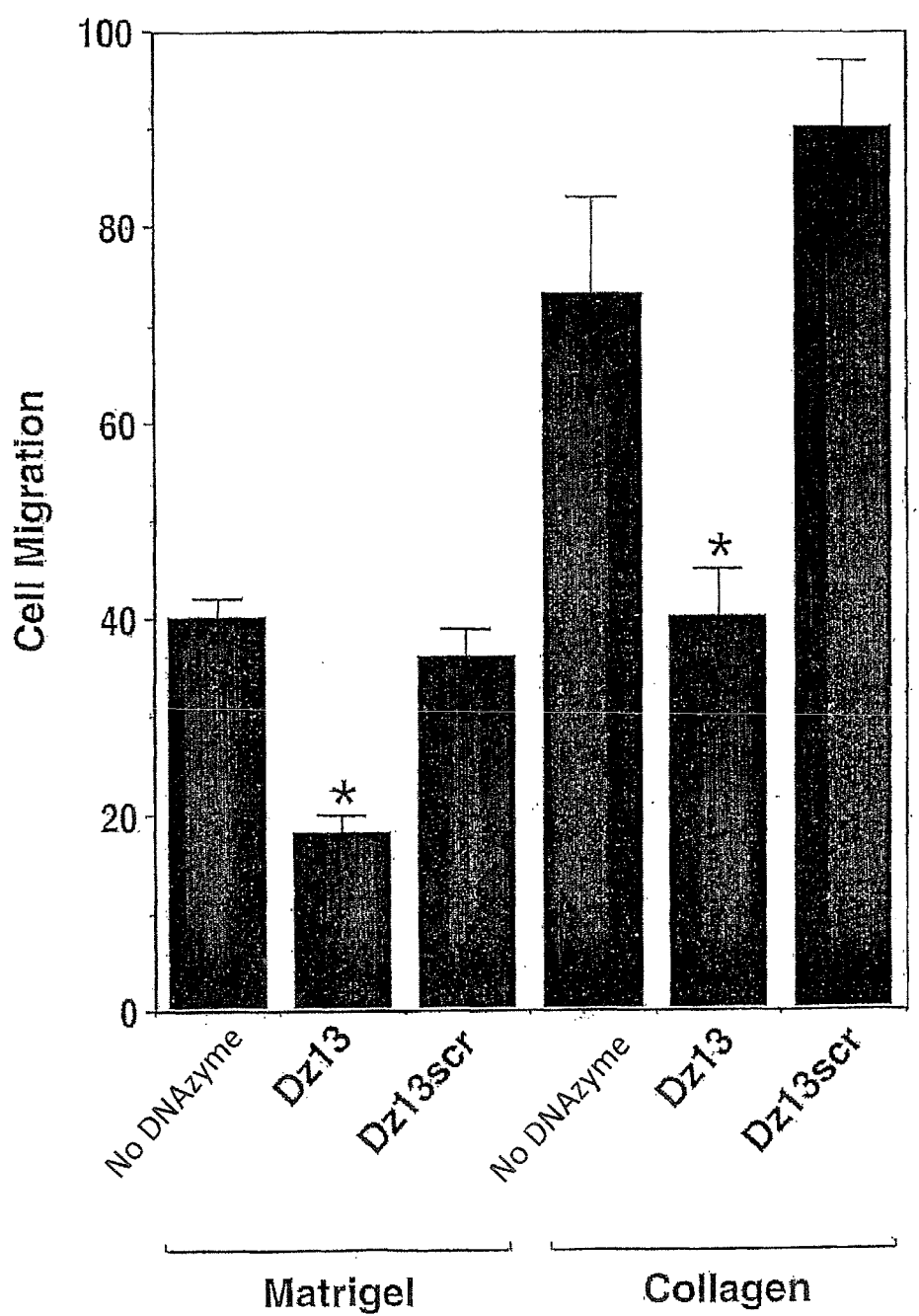

To demonstrate a role for c-Jun in microvascular endothelial cell migration, we scraped an endothelial monolayer in vitro and quantitated the population of cells in the denuded zone after 2 days, in the absence and presence of DNAzyme. Dz13 inhibited this reparative response to injury in a dose- and sequence-dependent manner. Modest inhibition of regrowth was apparent in the presence of 0.2 µM Dz13 (FIG. 9A) with almost complete inhibition observed at 0.4 µM (FIG. 9A). Dz13scr did not interfere with endothelial regrowth in this concentration range (FIG. 9A). These findings were confirmed using modified Boyden chambers coated with a reconstituted basement membrane (matrigel). Microvascular endothelial cell invasion through matrigel to the underside of the membrane was blocked 50% by Dz13 but not Dz13scr (FIG. 9B). Cell migration through filters coated with collagen type I was greater than with matrigel and also inhibited by 50% by Dz13, but not Dz13scr (FIG. 9B).

Dz13 Inhibits Microvascular Endothelial Cell MMP-2 mRNA, Protein Expression and Proteolytic Activity.

Figure 10:
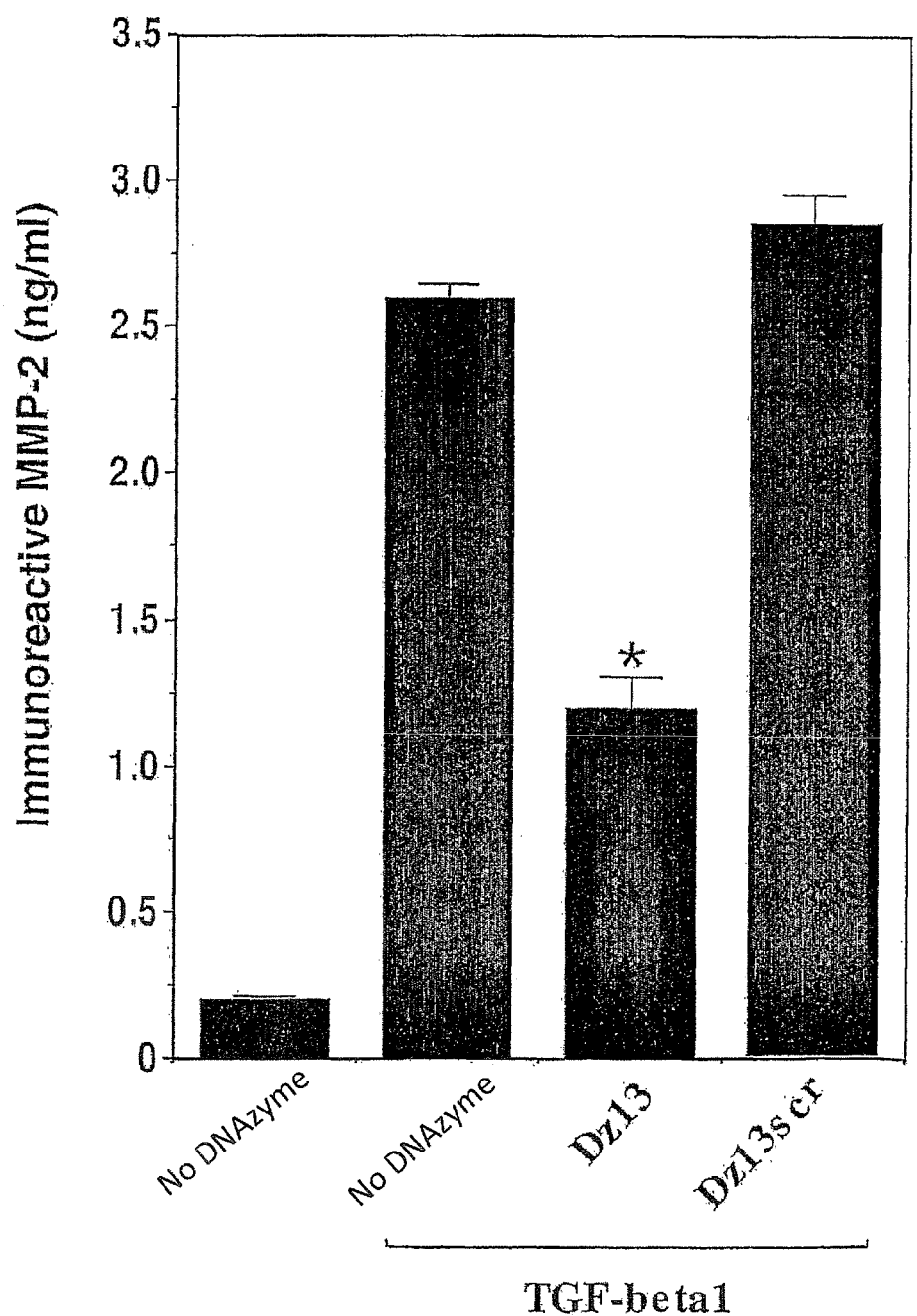
FIG. 10. Dz13 blocks MMP-2 expression and proteolysis. MMP-2 protein expression was quantitated by enzyme-linked immunosorbent assay. Endothelial cells transfected with DNAzyme were incubated with 10 ng/ml TGF-betal for 2 days in medium supplemented with 0.1% FBS. Conditioned media was harvested, centrifuged, normalized for equal protein, and levels of MMP-2 determined using commercial ELISA (Amersham Biosciences).

Matrix metalloproteinases (MMPs), proteinases that cleave basement membrane and extracellular matrix molecules, are key to the process of angiogenesis[45]. For example, mice deficient in MMP-2 (also known as gelatinase A) have compromised tumor-inducible angiogenesis and progression[46]. We hypothesised that Dz13 activity is mediated by its capacity to inhibit the expression of MMP-2. Assessment of MMP-2 mRNA and protein expression by semi-quantitative RT-PCR and enzyme-linked immunosorbent assay, respectively, demonstrated reduced MMP-2 expression upon treatment with Dz13 but no change using Dz13scr (FIG. 10). Analysis of MMP-2 activity secreted into the culture medium by gelatin zymography revealed significantly reduced MMP-2 proteolysis of gelatin by Dz13, which was rescued by overexpression of c-Jun. There was no change in MMP-2 activity in the presence of Dz13scr. Gelatin zymography demonstrated Dz13 inhibition of MMP-2 proteolysis and rescue by overexpression of c-Jun cDNA (data not shown). RT-PCR demonstrated that Dz13 blocked c-Jun mRNA expression (data not shown).

Dz13 Inhibits $VEGF_{165}$-induced Neovascularization in Rat Cornea.

Figure 11A:
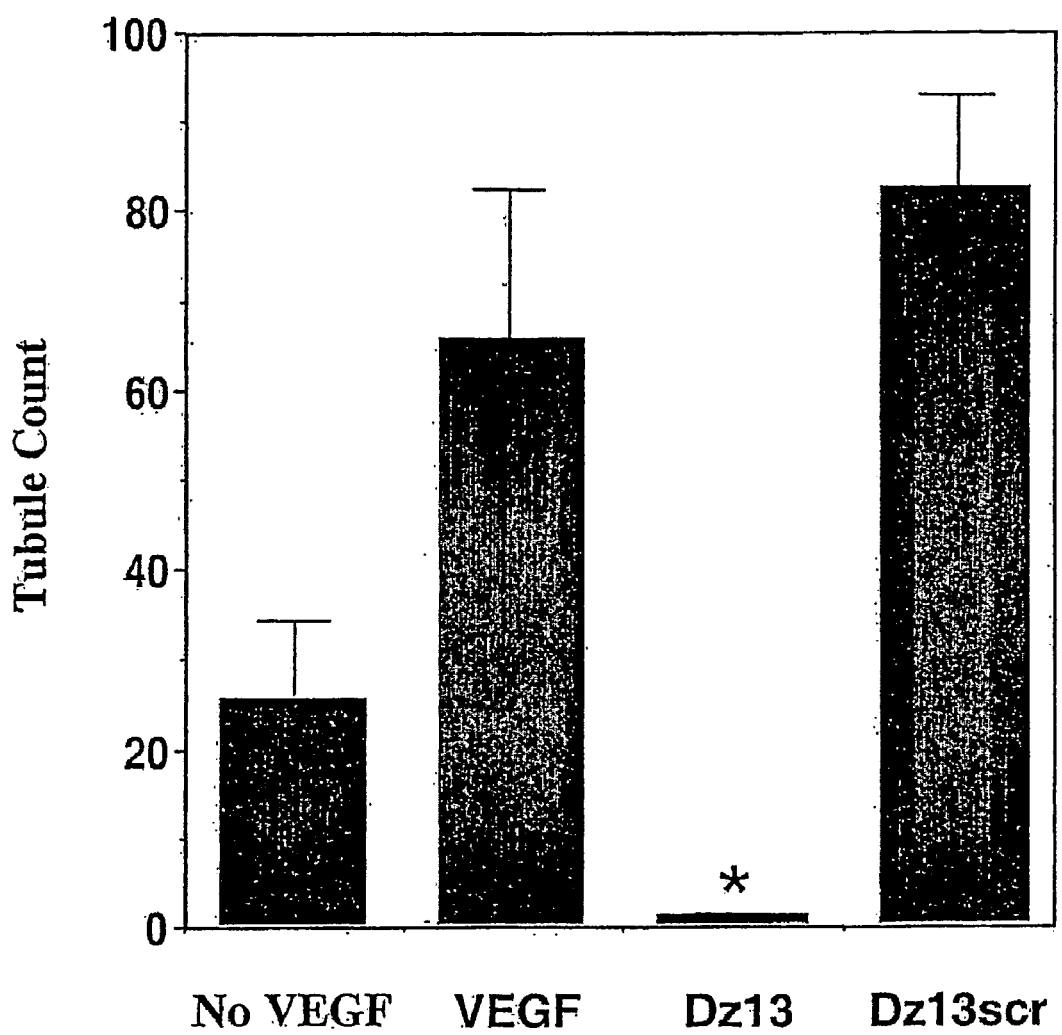
FIG. 11. Dz13 inhibits VEGF165-induced neovascularization in rat cornea. A, HMEC-1 cells (pre-transfected with 0.4 µM Dz13, and in medium containing 200 ng/ml of VEGF165) were plated into 96wps containing matrigel and tubule formation was quantitated under microscopy after 8 h. Quantitation of B, the number of blood vessels in the rat cornea and C, the corneal surface area occupied by these new vessels. Asterisk indicates p<0.05 by Student's t-test relative to control.
Figure 11B:
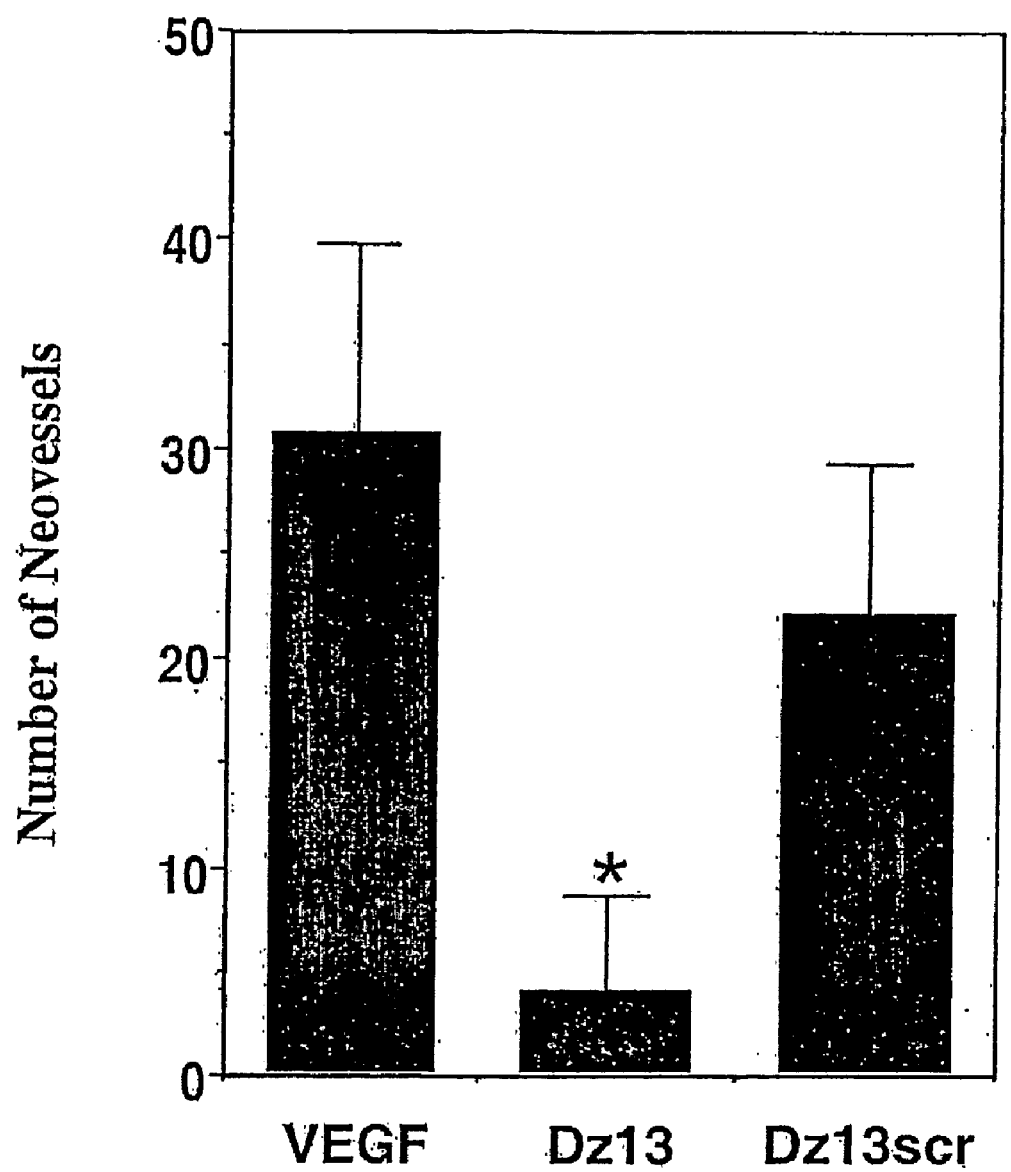
Figure 11C:
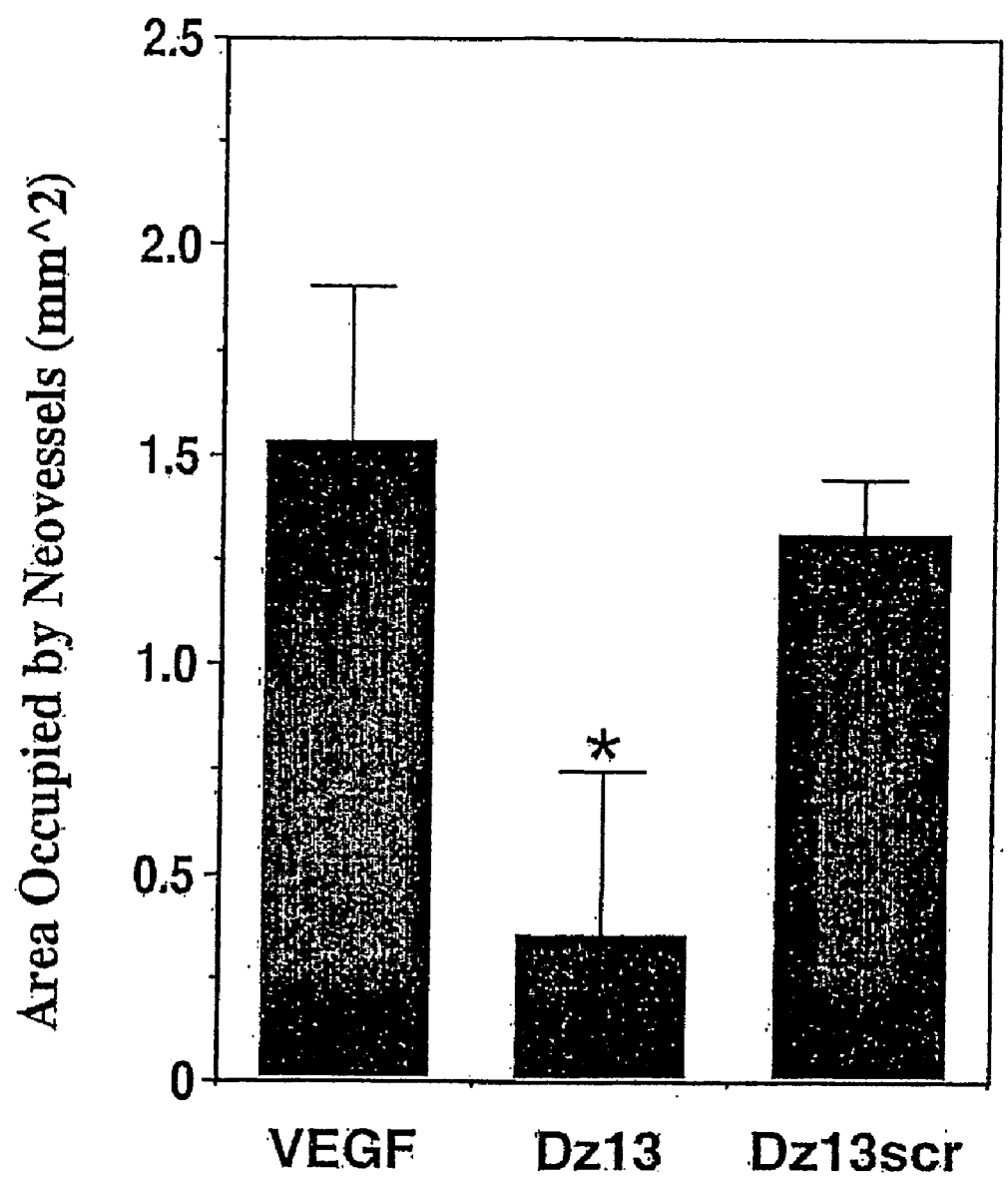

Corneal neovascularization is a sight-threatening condition usually associated with inflammatory or infectious disorders[47]. A hallmark process in corneal disease is the invasion of blood vessels into what is normally avascular tissue[48]. We evaluated the capacity of Dz13 to inhibit angiogenesis in rat model of corneal neovascularization, a process involving MMP-2 expression[49]. Implantation of vascular endothelial growth factor $(VEGF)_{165}$-soaked disks in the normally avascular rat cornea stimulates new blood vessel growth from the limbus toward the implant within 5 days. This growth factor is also strongly implicated in the pathogenesis of human corneal neovascularization[50]. Western blot analysis using polyclonal c-Jun antibodies and extracts of growth-quiescent HMEC-1 cells pre-treated with DNAzyme (0.4 µM) 2 h after exposure to $VEGF_{165}$ (100 µg/ml) demonstrated inhibition of c-Jun expression with no change in Sp1 expression (data not shown). Western blot analysis demonstrates that $VEGF_{165}$ can induce c-Jun expression and that this is blocked by Dz13 but not by Dz13scr (data not shown). Sp1 levels were unchanged. Dz13 also inhibited $VEGF_{165}$-inducible microvascular tubule formation in vitro. Slit lamp biomicroscopic visualization demonstrated that Dz13 blocked the corneal angiogenic response to $VEGF_{165}$ following its conjunctival administration in a sequence-specific manner. Quantitative determination of neovascularization revealed 81% inhibition in the number of blood vessels (FIG. 11 A). Dz13 inhibited the corneal surface area occupied by these new vessels by 74% (FIG. 11B).

Dz13 Inhibits Solid Melanoma Growth in Mice.

Aggressive melanoma lesions are associated with a significant increase in blood vessel density[51]. Previous studies have demonstrated that the in vivo growth of solid B16 melanoma is blocked by administration of anti-Flk-1 monoclonal antibodies[52] and MMP-2 inhibitors[53,54] indicating the dependence of tumor growth on angiogenesis and matrix degradation. Immunohistochemical analysis of primary human cutaneous malignant melanoma demonstrates that c-Jun is strongly expressed in endothelial cell-specific $CD31^+$ blood vessels and in surrounding melanoma cells (data not shown). Intense cytoplasmic staining in both cell types was also apparent using antibodies to MMP-2 (data not shown). c-Jun expression in primary melanoma has hitherto not been described.

Figure 12A:
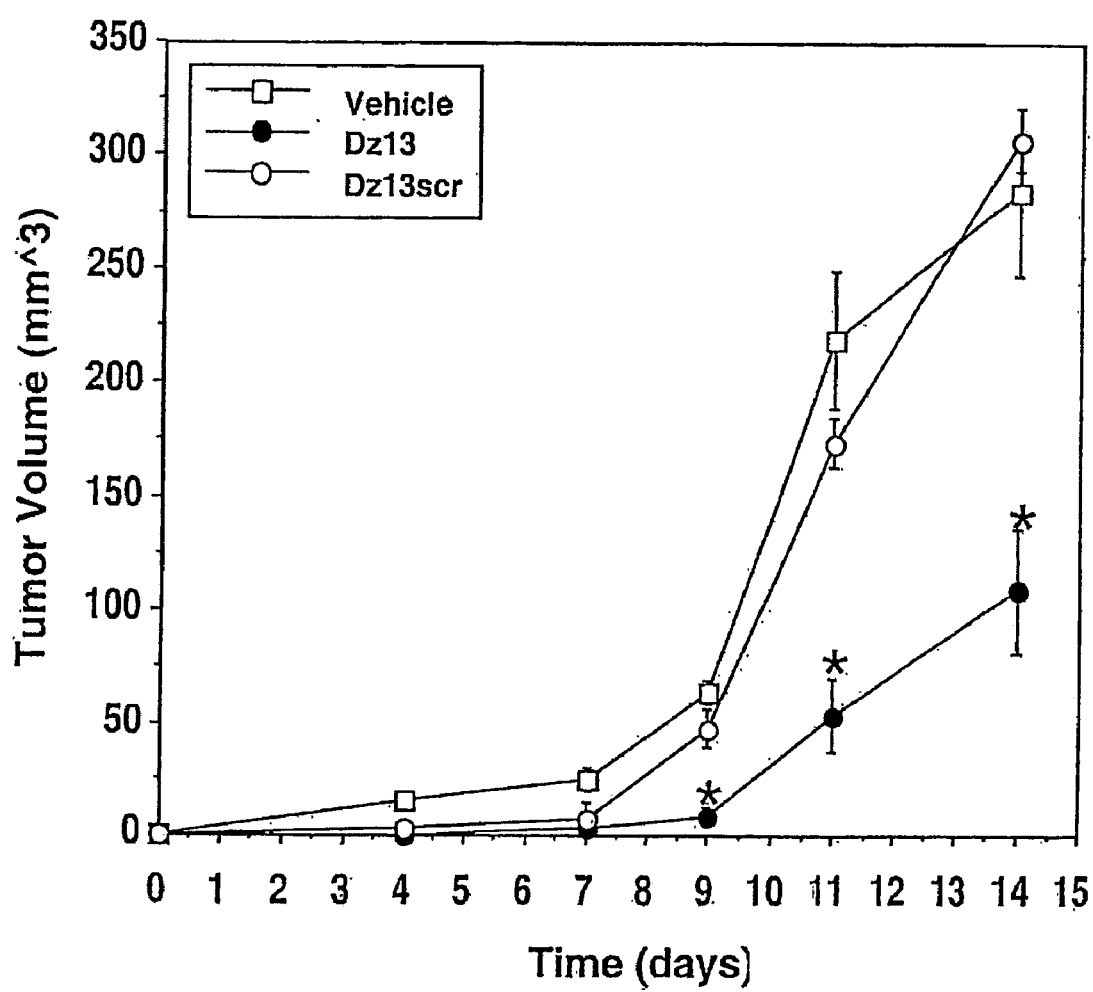
FIG. 12. Dz13 blockade of solid melanoma growth in mice. A, Dz13 inhibition of solid malignant B16 tumor growth in a sequence-specific manner. Tumour volumes were evaluated as indicated on the x-axis. B, Mean total body weight in the DNAzyme and vehicle-treated cohorts. C, Proliferation 2 days after exposure of growth-quiescent cultured microvascular endothelial cells pre-treated with DNAzyme (0.4 µM) to serum. Seventeen of the 18 nucleotides in the Dz13 target site in human c-Jun mRNA (5'-CAA CGC CUC G1311 ↓ UUC CUC CcG-3') (SEQ ID NO:30) are conserved in murine c-Jun mRNA (5'-CAA CGC CUC G ↓ UUC CUC CaG-3') (SEQ ID NO:14). Asterisk indicates p<0.05 by Student's t-test relative to control. Immunohistochemical analysis in vascularized human malignant cutaneous melanoma tissue revealed that c-Jun and MMP-2 are expressed in CD31+ endothelium and surrounding melanoma cells (data not shown). Western blot analysis demonstrated Dz13 inhibition of c-Jun protein 2 h after exposure of the cells to serum (data not shown).
Figure 12B:
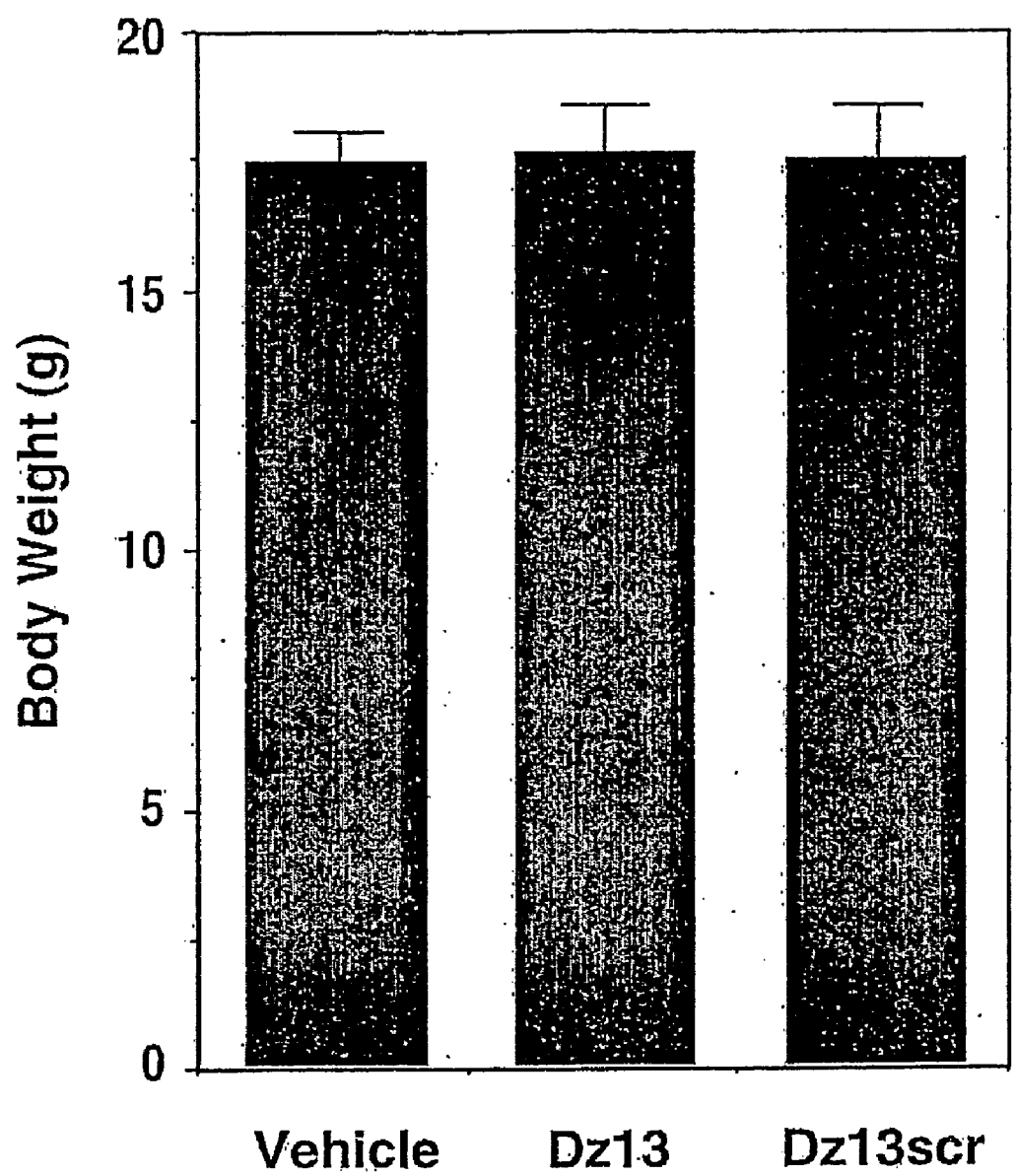
Figure 12C:
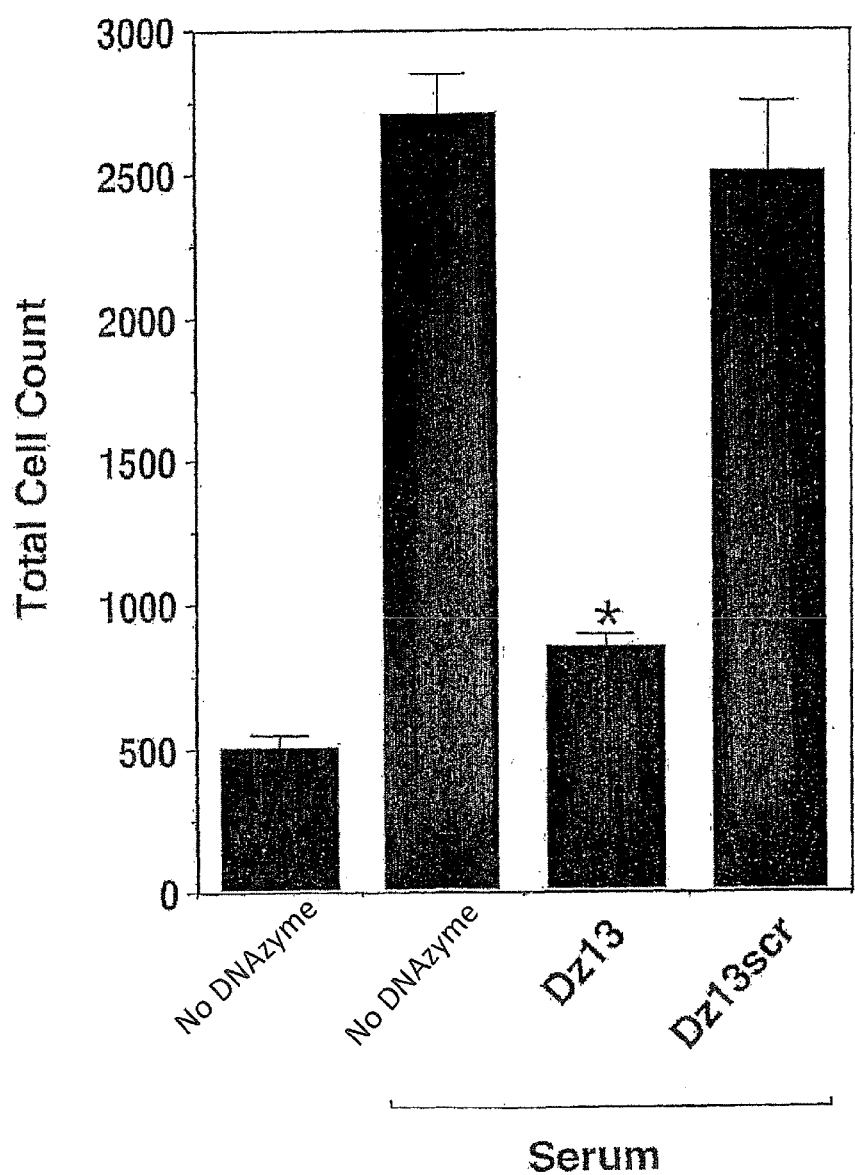

Dz13 blocked solid B16 growth in C57BL/J6 mice in both a time-dependent and sequence-specific manner (FIG. 12A). The c-Jun DNAzyme inhibited tumor growth by approximately 70% within 14 days, whereas Dz13scr-treated tumors were indistinguishable from the vehicle group (FIG. 12A). Dz13 efficacy was not associated with any difference in body weight relative to the other treatment groups (FIG. 12B). There was also no evidence of lethargy, ruffled fur, skin erythema, and soft faeces, consistent with the lack of a toxic effect. Dz13 blocked c-Jun protein expression (data not shown) and proliferation (FIG. 12C) of murine microvascular endothelial cells, whereas Dz13scr failed to inhibit either process.

Strategies that target specific genes in complex biological milieu may be achieved with synthetic agents including ribozymes, minizymes, antisense oligonucleotides, RNA interference and DNAzymes. DNAzymes have been used versatile tools that tease out the precise functions of the targeted gene in a variety of cellular processes[55]. These molecules have also been used as inhibitors of restenosis and in-stent restenosis, processes involving vascular smooth muscle cell hyperplasia[33,56,57]. This study has shown that DNAzymes targeting c-Jun can serve as potent inhibitors of microvascular endothelial cell mitogenesis, migration, corneal neovascularization and solid tumor growth. Accordingly, we provide here the first direct evidence for the key role of c-Jun in angiogenesis.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

1. Ross, R., Glomset, J. A., Kariya, B. & Harker, L. A platelet-dependent serum factor that stimulates the proliferation of arterial smooth muscle cells in vitro. *Proc. Natl. Acad. Sci. USA* 71, 1207-1210 (1974).
2. Miano, J. M., Tota, R. R., Vlasic, N., Danishefsky, K. J. & Stemerman, M. B. Early proto-oncogene expression in rat aortic smooth muscle cells following endothelial removal. *Am. J. Pathol.* 137, 761-765 (1990).
3. Watson, L. et al. JNK and c-Jun but not ERK and c-Fos are associated with sustained neointima-formation after balloon injury. *Eur. J. Clin. Invest.* 30, 11-17 (2000).
4. Wagner, E. F. AP-1. *Oncogene* 20, 2334-2335 (2001).
5. Kanatani et al., Transforming growth factor beta and dexamethasone cooperatively enhance c-Jun gene expression and inhibit the growth of human monocytoid leukemia cells. Cell Growth Differ 1996;7:187-196.
6. Nishio, H., Matsui, K., Tsuji, H. & Suzuki, K. Immunohistochemical study of the phosphoylated and activated form of c-Jun NH2-terminal kinase in human aorta. *Histochem. J.* 33, 167-171 (2001).
7. Metzler, B., Hu, Y., Dietrich, H. & Xu, Q. Increased expression and activation of stress-activated protein kinases/c-Jun NH2-terminal protein kinases in atherosclerotic lesions coincide with p53. *Am. J Pathol.* 156, 1875-1886 (2000).
8. Izumi, Y. et al. Gene transfer of dominant-negative mutants of extracellular signal-regulated kinase and c-Jun NH2-terminal kinase prevents neointimal formation in balloon-injured rat artery. *Circ. Res.* 88(2001).
9. Silverman et al., Vascular smooth muscle cells express the transcriptional corepressor NAB2 in response to injury. Am J Pathol 1999;155:1311-1317.
10. Khachigian et al., GC factor 2 represses platelet-derived growth factor A-chain gene transcription and is itself induced by arterial injury. Circ Res. 1999;11;84:1258-1267.
11. Santiago et al., Induction of the transcriptional repressor Yin Yang-1 by vascular cell injury. Autocrine/paracrine role of endogenous fibroblast growth factor-2. J Biol Chem. 2001;276:41143-1149.

12. Pessah et al., c-Jun interacts with the corepressor TG-interacting factor (TGIF) to suppress Smad2 transcriptional activity. Proc Natl Acad Sci USA 2001;98:6198-6203.
13. Dennler et al., c-Jun inhibits transforming growth factor beta-mediated transcription by repressing Smad3 transcriptional activity. J Biol Chem. 2000;275:28858-28865.
14. Hanahan, D., and Folkman, J. (1996). Patterns and emerging mechanisms of the angiogenic switch during tumorigenesis. Cell 86, 353-364.
15. Haseloff, J., Gerlach, W. L. (1988) Nature (334):585-591.
16. Breaker, R. R. and Joyce, G. (1994) Chemistry and Biology 1:223-229.
17. Koizumi, M., et al. (1989) Nucleic Acids Research 17:7059-7069.
18. Otsuka and Koizumi JP4235919.
19. Kashani-Sabet, M., et al. (1992) Antisense Research and Development 2:3-15.
20. Raillard, S. A. and Joyce, G. F. (1996) Biochemistry 35:11693-11701.
21. Carmi, N., et al. (1996) Chemistry and Biology 3:1039-1046.
22. Symons, R. H. (1992) Annu. Rev. Biochem. 61, 641-671.
23. Sun, L. Q., et al. (1997) Mol. Biotechnology 7:241-251.
24. Pan, T. and Uhlenbeck, O. C. (1996) Biochemistry 31:3887-3895.
25. Tsang, J. and Joyce, G. F. (1994) Biochemistry 33:5966-5973.
26. Breaker, R. R. and Joyce, G. F. (1995) Chem. Biol. 2, 655-660.
27. Santoro, S. W. & Joyce, G. F. A general purpose RNA-cleaving DNA enzyme. *Proc. Natl. Acad. Sci. USA* 94, 4262-4266 (1997).
28. Kuwabara, T. et al. Comparison of the specificities and catalytic activities of hammerhead ribozymes and DNA enzymes with respect to the cleavage of BCR-ABL chimeric L6 (b2a2) mRNA. *Nucleic Acid Res.* 25, 3074-3091 (1997).
29. Chiang et al. (1996) J Biol Chem 271:23999.
30. Lowe, H. C. et al. Catalytic oligodeoxynucleotides define a critical regulatory role for early growth response factor-1 in the porcine coronary artery model of in-stent restenosis. *Circulation Research* 89, 670-677 (2001).
31. Zuker, M. On finding all suboptimal foldings of an RNA molecule. *Science* 244, 48-52 (1989).
32. Santoro, S. W. & Joyce, G. F. Mechanism and utility of an RNA-cleaving DNA enzyme. *Biochemistry* 37, 13330-13342 (1998).
33. Santiago, F. S. et al. New DNA enzyme targeting Egr-1 mRNA inhibits vascular smooth muscle proliferation and regrowth factor injury. *Nature Med.* 11, 1264-1269 (1999).
34. Clowes, A. W., Reidy, M. A. & Clowes, M. M. Kinetics of cellular proliferation after arterial injury. *Lab. Invest.* 49, 327-333 (1983).
35. Autieri, M. V., Yue, T.-L., Ferstein, G. Z. & Ohlstein, E. Antisense oligonucleotides to the p65 subunit of NF-kB inhibit human vascular smooth muscle cell adherence and proliferation and prevent neointima formation in rat carotid arteries. *Biochem. Biophys. Res. Commun.* 213, 827-836 (1995).
36. Simons, M., Edelman, E. R., DeKeyser, J.-L., Langer, R. & Rosenberg, R. Antisense c-myb oligonucleotides inhibit intimal arterial smooth muscle cell accumulation in vivo. *Nature* 359, 67-70 (1992).
37. Bennett, M. R. et al. Inhibition of vascular smooth muscle cell proliferation in vitro and in vivo by c-myc antisense oligodeoxynucleotides. *J. Clin. Invest.* 93, 820-828 (1994).
38. Morishita, R. et al. Single intraluminal delivery of antisense cdc2 kinase and proliferating-cell nuclear antigen oligonucleotides results in chronic inhibition of neointimal hyperplasia. *Proc. Natl. Acad. Sci. USA* 90, 84748478 (1993).
39. Wakisaka, S. et al. Involvement of simultaneous multiple transcription factor expression, including cAMP responsive element binding protein and OCT-1, for synovial cell outgrowth in patients with rheumatoid arthritis. *Ann. Rheum. Dis.* 57, 487-494 (1998).
40. van Dam, H. & Castellazzi, M. Distinct roles of Jun:Fos and Jun:ATF dimers in oncogenesis. *Oncogene* 20, 2453-2464 (2001).
41. Chen, B. et al. Mesenchymal cells isolated after acute lung injury manifest an enhanced proliferative phenotype. *J. Clin. Invest.* 90, 1778-1785 (1992).
42. Kondo, T., Ohshima, T., Sato, Y., Mayama, T. & Eisenmenger, W. Immunohistochemical study on the expression of c-Fos and c-Jun in human skin wounds. *Histochem. J.* 32,509-514 (2000).
43. Gillardon, F., Zimmermann, M. & Uhlmann, E. Expression of c-Fos and c-Jun in the cornea, lens, and retina after ultraviolet irradiation of the rat eye and effects of topical antisense oligodeoxynucleotides. *Br. J. Ophthalmol.* 79, 277-281 (1995).
44. Shevde, N. K., Bendixen, A. C., Dienger, K. M. & Pike, J. W. Estrogens suppress RANK ligand-induced osteoclast differentiation via a stromal cell independent mechanism involving c-Jun repression. *Proc. Natl. Acad. Sci. USA* 97,7829-7834 (2000).
45. Haas, T. L., and Madri, J. A. (1999). Extracellular matrix-driven matrix metalloproteinase production in endothelial cells: implications for angiogenesis. Trends Cardiovasc. Med. 9,70-77.
46. Itoh, T., Tanioka, M., Yoshida, H., Yoshioka, T., Nishimoto, H., and Itohara, S. (1998). Reduced angiogenesis and tumor progression in gelatinase A-deficient mice. Cancer Res. 58, 1048-1051.
47. Chang, J. H., Gabison, E. E., Kato, T., and Azar, D. T. (2001). Corneal neovascularization. Curr. Opin. Ophthalmol. 12, 242-249.
48. Klintworth, G. K. (1977). The contribution of morphology to our understanding of the pathogenesis of experimentally produced corneal vascularization. Invest Ophthalmol. Vis. Sci. 16, 281-285.
49. Kvanta, A., Sarman, S., Fagerholm, P., Seregard, S., and Steen, B. (2000). Expression of matrix metalloproteinase-2 (MMP-2) and vascular endothelial growth factor (VEGF) in inflammation-associated corneal neovascularization. Exp Eye Res 70, 419-428.
50. Lai, C. M., Spilsbury, K., Brankov, M., Zaknich, T., and Rakoczy, P. E. (2002). Inhibition of corneal neovascularization by recombinant adenovirus mediated antisense VEGF RNA. Exp Eye Res. 75, 625-634.
51. de Waal, R. M., van Altena, M. C., Erhard, H., Weidle, U. H., Nooijen, P. T., and Ruiter, D. J. (1997). Lack of lymphangiogenesis in human primary cutaneous melanoma. Consequences for the mechanism of lymphatic dissemination. Am. J. Pathol. 150, 1951-1957.
52. Prewett, M., Huber, J., Li, Y., Santiago, A., O'Connor, W., King, K., Overholser, J., Hooper, A., Pytowski, B., Witte, L, Bohlen, P., and Hicklin, D. J. (1999). Antivascular endothelial growth factor receptor (fetal liver kinase 1) monoclonal antibody inhibits tumor angiogenesis and growth of several mouse and human tumors. Cancer Res. 59, 5209-5218.

53. Maekawa, R., Maki, H., Yoshida, H., Hojo, K., Tanaka, H., Wada, T., Uchida, N., Takeda, Y., Kasai, H., Okamoto, H., Tsuzuki, H., Kambayashi, Y., Watanabe, F., Kawada, K., Toda, K., Ohtani, M., Sugita, K., and Yoshioka, T. (1999). Correlation of antiangiogenic and anti tumor efficacy of N-biphenyl sulfonyl-phenylalanine hydroxiamic add (BPHA), an orally-active, selective matrix metalloproteinase inhibitor. Cancer Res 59, 1231-1235.
54. Shalinsky, D. R., Brekken, J., Zou, H., McDermott, C. D., Forsyth, P., Edwards, D., Margosiak, S., Bender, S., Truitt, G., Wood, A., Varki, N. M., and Appelt, K. (1999). Broad antitumor and antiangiogenic activities of AG3340, a potent and selective MMP inhibitor undergoing advanced oncology clinical trials. Ann N Y Acad Sd 878, 236-270.
55. Khachigian, L. M. (2002). DNAzymes: cutting a path to a new class of therapeutics. Curr. Opin. Mol. Therap. 4, 119-121.
56. Lowe, H. C., Fahmy, R. G., Kavurma, M. M., Baker, A., Chesterman, C. N., and Khachigian, L. M. (2001). Catalytic oligodeoxynucleotides define a key regulatory role for early growth response factor-1 in the porcine model of coronary in-stent restenosis. Circulation Research 89,670-677.
57. Lowe, H. C., Chesterman, C. N., and Khachigian, L. M. (2002). Catalytic antisense DNA molecules targeting Egr-1 inhibit neointima formation following permanent ligation of rat common cartoid arteries. Thromb. Haemost. 87, 134-140.

The invention claimed is:

1. A method of reducing ocular angiogenesis in a subject, the method comprising administering to the eye of the subject a pharmaceutical composition comprising an effective dose of a DNAzyme targeted against c-Jun, wherein the DNAzyme has the sequence of SEQ ID NO:5.

2. The method according to claim 1 wherein the DNAzyme incorporates a 3'-3' inversion at the 3' terminus.

* * * * *

SEQUENCE LISTING

<160> NUMBER OF SEQ ID NOS: 33

<210> SEQ ID NO 1
<211> LENGTH: 3622
<212> TYPE: DNA
<213> ORGANISM: Homo sapiens

<400> SEQUENCE: 1

```
cccggggagg ggaccgggga acagagggcc gagaggcgtg cggcagggg gagggtagga      60
gaaagaaggg cccgactgta ggagggcagc ggagcattac ctcatcccgt gagcctccgc     120
gggcccagag aagaatcttc tagggtggag tctccatggt gacgggcggg ccgccccc      180
tgagagcgac gcgagccaat gggaaggcct tggggtgaca tcatgggcta tttttagggg     240
ttgactggta gcagataagt gttgagctcg ggctggataa gggctcagag ttgcactgag     300
tgtggctgaa gcagcgaggc gggagtggag gtgcgcggag tcaggcagac agacagacac     360
agccagccag ccaggtcggc agtatagtcc gaactgcaaa tcttattttc ttttcaccttt    420
ctctctaact gcccagagct agcgcctgtg gctcccgggc tggtggttcg ggagtgtcca     480
gagagccttg tctccagccg gccccgggag gagagccctg ctgcccaggc gctgttgaca     540
gcggcggaaa gcagcggtac cccacgcgcc cgccggggga cgtcggcgag cggctgcagc     600
agcaaagaac tttcccggcg gggaggaccg gagacaagtg gcagagtccc ggagcgaact     660
tttgcaagcc tttcctgcgt cttaggcttc tccacgcgcg taaagaccag aaggcggcgg     720
agagccacgc aagagaagaa ggacgtgcgc tcagcttcgc tcgcaccggt tgttgaactt     780
gggcgagcgc gagccgcggc tgccgggcgc cctccccc tagcagcgga ggaggggaca      840
agtcgtcgga gtccgggcgg ccaagacccg ccgccggccg gccactgcag ggtccgcact     900
gatccgctcc gcggggagag ccgctgctct gggaagtgag ttcgcctgcg gactccgagg     960
aaccgctgcg cccgaagagc gctcagtgag tgaccgcgac ttttcaaagc cgggtagcgc    1020
gcgcgagtcg acaagtaaga gtgcgggagg catcttaatt aaccctgcgc tccctggagc    1080
gagctggtga ggagggcgca gcggggacga cagccagcgg gtgcgtgcgc tcttagagaa    1140
actttccctg tcaaaggctc cggggggcgc gggtgtcccc cgcttgccag agccctgttg    1200
cggccccgaa acttgtgcgc gcacgccaaa ctaacctcac gtgaagtgac ggactgttct    1260
atgactgcaa agatggaaac gaccttctat gacgatgccc tcaacgcctc gttcctcccg    1320
tccgagagcg gaccttatgg ctacagtaac cccaagatcc tgaaacagag catgacccctg   1380
aacctggccg acccagtggg gagcctgaag ccgcacctcc gcgccaagaa ctcggacctc    1440
ctcacctcgc ccgacgtggg gctgctcaag ctggcgtcgc ccgagctgga gcgcctgata    1500
```

-continued

```
atccagtcca gcaacgggca catcaccacc acgccgaccc ccacccagtt cctgtgcccc    1560 aagaaccgtga cagatgagca ggaggggttc gccgagggct tcgtgcgcgc cctggccgaa    1620
ctgcacagcc agaacacgct gcccagcgtc acgtcggcgg cgcagccggt caacggggca    1680
ggcatggtgg ctcccgcggt agcctcggtg gcagggggca gcggcagcgg cggcttcagc    1740
gccagcctgc acagcgagcc gccggtctac gcaaacctca gcaacttcaa cccaggcgcg    1800
ctgagcagcg gcggcgggc gccctcctac ggcgcggccg gctggccttt cccgcgcaa    1860 ccccagcagc agcagcagcc gccgcaccac ctgccccagc agatgcccgt gcagcacccg    1920
cggctgcagg ccctgaagga ggagcctcag acagtgcccg agatgcccgg cgagacaccg    1980
cccctgtccc ccatcgacat ggagtcccag gagcggatca aggcggagag gaagcgcatg    2040
aggaaccgca tcgctgcctc caagtgccga aaaaggaagc tggagagaat cgcccggctg    2100
gaggaaaaag tgaaaacctt gaaagctcag aactcggagc tggcgtccac ggccaacatg    2160
ctcagggaac aggtggcaca gcttaaacag aaagtcatga accacgttaa cagtgggtgc    2220
caactcatgc taacgcagca gttgcaaaca ttttgaagag agaccgtcgg gggctgaggg    2280
gcaacgaaga aaaaaaataa cacagagaga cagacttgag aacttgacaa gttgcgacgg    2340
agagaaaaaa gaagtgtccg agaactaaag ccaagggtat ccaagttgga ctgggttcgg    2400
tctgacggcg cccccagtgt gcacgagtgg aaggacttg gtcgcgccct cccttggcgt    2460
ggagccaggg agcggccgcc tgcgggctgc cccgcttgc ggacgggctg tccccgcgcg    2520
aacggaacgt tggactttcg ttaacattga ccaagaactg catggaccta acattcgatc    2580
tcattcagta ttaagggggg agggggagg gggttacaaa ctgcaataga gactgtagat    2640
tgcttctgta gtactcctta agaacacaaa gcgggggag ggttggggag gggcggcagg    2700
agggaggttt gtgagagcga ggctgagcct acagatgaac tctttctggc ctgctttcgt    2760
taactgtgta tgtacatata tatatttttt aatttgatta aagctgatta ctgtcaataa    2820
acagcttcat gcctttgtaa gttatttctt gtttgtttgt ttgggtatcc tgcccagtgt    2880
tgtttgtaaa taagagattt ggagcactct gagtttacca tttgtaataa agtatataat    2940 tttttatgt tttgtttctg aaaattccag aaaggatatt taagaaaata caataaacta    3000
ttggaaagta ctcccctaac ctcttttctg catcatctgt agatcctagt ctatctaggt    3060
ggagttgaaa gagttaagaa tgctcgataa aatcactctc agtgcttctt actattaagc    3120
agtaaaaact gttctctatt agacttagaa ataaatgtac ctgatgtacc tgatgctatg    3180
tcaggcttca tactccacgc tccccccagcg tatctatatg gaattgctta ccaaaggcta    3240
gtgcgatgtt tcaggaggct ggaggaaggg gggttgcagt ggagagggac agcccactga    3300
gaagtcaaac atttcaaagt ttggattgca tcaagtggca tgtgctgtga ccatttataa    3360
tgttagaaat tttacaatag gtgcttattc tcaaagcagg aattggtggc agattttaca    3420
aaagatgtat ccttccaatt tggaatcttc tctttgacaa ttcctagata aaagatggc    3480 ctttgtctta tgaatatttta taacagcatt ctgtcacaat aaatgtattc aaataccaat    3540
aacagatctt gaattgcttc cctttactac ttttttgttc ccaagttata tactgaagtt    3600 tttatttta gttgctgagg tt    3622
```

<210> SEQ ID NO 2
<211> LENGTH: 34
<212> TYPE: DNA
<213> ORGANISM: Artificial Sequence
<220> FEATURE:
<223> OTHER INFORMATION: Synthetic Construct (Dz13scr)
<220> FEATURE:

```
<221> NAME/KEY: misc_feature
<222> LOCATION: 34
<223> OTHER INFORMATION: n= 3'-3' linked inverted T

<400> SEQUENCE: 2
gcgacgtgag gctagctaca acgagtggag gagn                              34

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct (As13scr)
<220> FEATURE:
<221> NAME/KEY: misc_feature
<222> LOCATION: 20
<223> OTHER INFORMATION: n= 3'-3' linked inverted T

<400> SEQUENCE: 3
gcgacgtgac gtggaggagn                                              20

<210> SEQ ID NO 4
<211> LENGTH: 15
<212> TYPE: DNA
<213> ORGANISM: Artificial Sequence
<220> FEATURE:
<223> OTHER INFORMATION: Synthetic Construct (Catalytic domain of
      DNAzyme)

<400> SEQUENCE: 4
ggctagctac aacga                                                   15

<210> SEQ ID NO 5
<211> LENGTH: 33
<212> TYPE: DNA
<213> ORGANISM: Artificial Sequence
<220> FEATURE:
<223> OTHER INFORMATION: Synthetic Construct (DNAzyme)

<400> SEQUENCE: 5
cgggaggaag gctagctaca acgagaggcg ttg                               33

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct (Antisense oligonucleotide)

<400> SEQUENCE: 6
cgggaggaac gaggcgttg                                               19

<210> SEQ ID NO 7
<211> LENGTH: 38
<212> TYPE: DNA
<213> ORGANISM: Artificial Sequence
<220> FEATURE:
<223> OTHER INFORMATION: Synthetic Construct (Dz13(11+11) variant)
<220> FEATURE:
<221> NAME/KEY: misc_feature
<222> LOCATION: 38
<223> OTHER INFORMATION: n= 3'-3' linked inverted T

<400> SEQUENCE: 7
gacgggagga aggctagcta caacgagagg cgttgagn                          38

<210> SEQ ID NO 8
<211> LENGTH: 36
```

```
<212> TYPE: DNA
<213> ORGANISM: Artificial Sequence
<220> FEATURE:
<223> OTHER INFORMATION: Synthetic Construct (Dz13(10+10) variant)
<220> FEATURE:
<221> NAME/KEY: misc_feature
<222> LOCATION: 36
<223> OTHER INFORMATION: n= 3'-3' linked inverted T

<400> SEQUENCE: 8
acgggaggaa ggctagctac aacgagaggc gttgan                                    36

<210> SEQ ID NO 9
<211> LENGTH: 32
<212> TYPE: DNA
<213> ORGANISM: Artificial Sequence
<220> FEATURE:
<223> OTHER INFORMATION: Synthetic Construct (Dz13(8+8) variant)
<220> FEATURE:
<221> NAME/KEY: misc_feature
<222> LOCATION: 32
<223> OTHER INFORMATION: n= 3'-3' linked inverted T

<400> SEQUENCE: 9
gggaggaagg ctagctacaa cgagaggcgt tn                                        32

<210> SEQ ID NO 10
<211> LENGTH: 38
<212> TYPE: DNA
<213> ORGANISM: Artificial Sequence
<220> FEATURE:
<223> OTHER INFORMATION: Synthetic Construct (Dz13(11+11)scr)
<220> FEATURE:
<221> NAME/KEY: misc_feature
<222> LOCATION: 38
<223> OTHER INFORMATION: n= 3'-3' linked inverted T

<400> SEQUENCE: 10
gagcgacgtg aggctagcta caacgagtgg aggagagn                                  38

<210> SEQ ID NO 11
<211> LENGTH: 36
<212> TYPE: DNA
<213> ORGANISM: Artificial Sequence
<220> FEATURE:
<223> OTHER INFORMATION: Synthetic Construct (Dz13(10+10)scr)
<220> FEATURE:
<221> NAME/KEY: misc_feature
<222> LOCATION: 36
<223> OTHER INFORMATION: n= 3'-3' linked inverted T

<400> SEQUENCE: 11
agcgacgtga ggctagctac aacgagtgga ggagan                                    36

<210> SEQ ID NO 12
<211> LENGTH: 32
<212> TYPE: DNA
<213> ORGANISM: Artificial Sequence
<220> FEATURE:
<223> OTHER INFORMATION: Synthetic Construct (Dz13(8+8)scr)
<220> FEATURE:
<221> NAME/KEY: misc_feature
<222> LOCATION: 32
<223> OTHER INFORMATION: n= 3'-3' linked inverted T

<400> SEQUENCE: 12
cgacgtgagg ctagctacaa cgagtggagg an                                        32

<210> SEQ ID NO 13
<211> LENGTH: 21
```

```
<212> TYPE: RNA
<213> ORGANISM: Homo sapiens c-Jun mRNA

<400> SEQUENCE: 13
caacgccucg uuccucccgu c                                              21

<210> SEQ ID NO 14
<211> LENGTH: 19
<212> TYPE: RNA
<213> ORGANISM: Murine c-Jun mRNA

<400> SEQUENCE: 14
caacgccucg uuccuccag                                                 19

<210> SEQ ID NO 15
<211> LENGTH: 23
<212> TYPE: DNA
<213> ORGANISM: Artificial Sequence
<220> FEATURE:
<223> OTHER INFORMATION: Primer MMP-2 forward

<400> SEQUENCE: 15
gggacaagaa ccagatcaca tac                                            23

<210> SEQ ID NO 16
<211> LENGTH: 23
<212> TYPE: DNA
<213> ORGANISM: Artificial Sequence
<220> FEATURE:
<223> OTHER INFORMATION: Primer MMP-2 reverse

<400> SEQUENCE: 16
cttctcaaag ttgtaggtgg tgg                                            23

<210> SEQ ID NO 17
<211> LENGTH: 20
<212> TYPE: DNA
<213> ORGANISM: Artificial Sequence
<220> FEATURE:
<223> OTHER INFORMATION: Primer GAPDH forward

<400> SEQUENCE: 17
accacagtcc atgccatcac                                                20

<210> SEQ ID NO 18
<211> LENGTH: 20
<212> TYPE: DNA
<213> ORGANISM: Artificial
<220> FEATURE:
<223> OTHER INFORMATION: Primer GAPDH reverse

<400> SEQUENCE: 18
tccaccaccc tgttgctgta                                                20

<210> SEQ ID NO 19
<211> LENGTH: 21
<212> TYPE: RNA
<213> ORGANISM: pig c-Jun mRNA

<400> SEQUENCE: 19
caacgccucg uuccuccagu c                                              21

<210> SEQ ID NO 20
<211> LENGTH: 21
<212> TYPE: RNA
<213> ORGANISM: rat c-Jun mRNA
```

```
<400> SEQUENCE: 20
caacgccucg uuccuccagu c                                              21

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct (As13)
<220> FEATURE:
<221> NAME/KEY: misc_feature
<222> LOCATION: 20
<223> OTHER INFORMATION: n= 3'-3' linked inverted T

<400> SEQUENCE: 21
cgggaggaac gaggcgttgn                                                20

<210> SEQ ID NO 22
<211> LENGTH: 34
<212> TYPE: DNA
<213> ORGANISM: Artificial Sequence
<220> FEATURE:
<223> OTHER INFORMATION: Synthetic Construct (Dz13)
<220> FEATURE:
<221> NAME/KEY: misc_feature
<222> LOCATION: 34
<223> OTHER INFORMATION: n= 3'-3' linked inverted T

<400> SEQUENCE: 22
cgggaggaag gctagctaca acgagaggcg ttgn                                34

<210> SEQ ID NO 23
<211> LENGTH: 19
<212> TYPE: DNA
<213> ORGANISM: Homo sapiens- target site for Dz9 A1261 (9+9)

<400> SEQUENCE: 23
gactgttcta tgactgcaa                                                 19

<210> SEQ ID NO 24
<211> LENGTH: 19
<212> TYPE: DNA
<213> ORGANISM: Homo sapiens- target site for Dz10 A1273 (9+9)

<400> SEQUENCE: 24
actgcaaaga tggaaacga                                                 19

<210> SEQ ID NO 25
<211> LENGTH: 19
<212> TYPE: DNA
<213> ORGANISM: Homo sapiens- target site for Dz11 A1289 (9+9)

<400> SEQUENCE: 25
cgaccttcta tgacgatgc                                                 19

<210> SEQ ID NO 26
<211> LENGTH: 19
<212> TYPE: DNA
<213> ORGANISM: Homo sapiens- target site for Dz12 A1295 (9+9)

<400> SEQUENCE: 26
tctatgacga tgccctcaa                                                 19

<210> SEQ ID NO 27
<211> LENGTH: 19
```

```
<212> TYPE: DNA
<213> ORGANISM: Homo sapiens- target site for Dz13 G1311 (9+9)

<400> SEQUENCE: 27
caacgcctcg ttcctcccg                                                19

<210> SEQ ID NO 28
<211> LENGTH: 19
<212> TYPE: DNA
<213> ORGANISM: Homo sapiens- target site for Dz14 A1498 (9+9)

<400> SEQUENCE: 28
gagcgcctga taatccagt                                                19

<210> SEQ ID NO 29
<211> LENGTH: 19
<212> TYPE: DNA
<213> ORGANISM: Homo sapiens- target site for Dz15 A1501 (9+9)

<400> SEQUENCE: 29
cgcctgataa tccagtcca                                                19

<210> SEQ ID NO 30
<211> LENGTH: 19
<212> TYPE: RNA
<213> ORGANISM: Homo sapiens c-Jun mRNA

<400> SEQUENCE: 30
caacgccucg uuccucccg                                                19

<210> SEQ ID NO 31
<211> LENGTH: 1215
<212> TYPE: DNA
<213> ORGANISM: Homo sapiens

<400> SEQUENCE: 31
agagttgcac tgagtgtggc tgaagcagcg aggcgggagt ggaggtgcgc ggagtcaggc      60
agacagacag acacagccag ccagccaggt cggcagtata gtccgaactg caaatcttat     120
tttcttttca ccttctctct aactgcccag agctagcgcc tgtggctccc gggctggtgg     180
ttcgggagtg tccagagagc cttgtctcca gccggccccg ggaggagagc cctgctgccc     240
aggcgctgtt gacagcggcg gaaagcagcg gtaccccacg cgcccgccgg gggacgtcgg     300
cgagcggctg cagcagcaaa gaactttccc ggcggggagg accggagaca agtggcagag     360
tcccggagcg aacttttgca agcctttcct gcgtcttagg cttctccacg gcggtaaaga     420
ccagaaggcg gcggagagcc acgcaagaga agaaggacgt gcgctcagct tcgctcgcac     480
cggttgttga acttgggcga gcgcgagccg cggctgccgg gcgcccccct ccctagcag      540 cggaggaggg gacaagtcgt cggagtccgg gcggccaaga cccgccgccg gccggccact     600
gcagggtccg cactgatccg ctccgcgggg agagccgctg ctctgggaag tgagttcgcc     660
tgcggactcc gaggaaccgc tgcgcccgaa gagcgctcag tgagtgaccg cgacttttca     720
aagccgggta gcgcgcgcga gtcgacaagt aagagtgcgg gaggcatctt aattaaccct     780
gcgctccctg gagcgagctg gtgaggaggg cgcagcgggg acgacagcca gcgggtgcgt     840
gcgctcttag agaaactttc cctgtcaaag gctccggggg gcgcgggtgt ccccgcttg     900 ccagagccct gttgcggccc cgaaacttgt gcgcgcacgc caaactaacc tcacgtgaag     960
tgacggactt ttctatgact gcaaagatgg aaacgacctt ctatgacgat gccctcaacg    1020
cctcgttcct cccgtccgag agcggacctt atggctacag taaccccaag atcctgaaac    1080
```

-continued

```
agagcatgac cctgaacctg gccgacccag tggggagcct gaagccgcac ctccgcgcca    1140
agaactcgga cctcctcacc tcgcccgacg tggggctgct caagctggcg tcgcccgagc    1200
tggagcgcct gataa                                                     1215

<210> SEQ ID NO 32
<211> LENGTH: 202
<212> TYPE: DNA
<213> ORGANISM: Homo sapiens

<400> SEQUENCE: 32
tgccctcaac gcctcgttcc tcccgtccga gagcggacct tatggctaca gtaaccccaa     60
gatcctgaaa cagagcatga ccctgaacct ggccgaccca gtggggagcc tgaagccgca    120
cctccgcgcc aagaactcgg acctcctcac ctcgcccgac gtgggctgc tcaagctggc    180 gtcgcccgag ctggagcgcc tg                                             202

<210> SEQ ID NO 33
<211> LENGTH: 480
<212> TYPE: DNA
<213> ORGANISM: Homo sapiens

<400> SEQUENCE: 33
actttccctg tcaaaggctc cgggggggcgc gggtgtcccc cgcttgccag agccctgttg     60 cggcccgaa acttgtgcgc gcacgccaaa ctaacctcac gtgaagtgac ggactgttct    120
atgactgcaa agatggaaac gaccttctat gacgatgccc tcaacgcctc gttcctcccg    180
tccgagagcg gaccttatgg ctacagtaac cccaagatcc tgaaacagag catgaccctg    240
aacctggccg acccagtggg gagcctgaag ccgcacctcc gcgccaagaa ctcggacctc    300
ctcacctcgc ccgacgtggg gctgctcaag ctggcgtcgc ccgagctgga gcgcctgata    360
atccagtcca gcaacgggca catcaccacc acgccgaccc ccacccagtt cctgtgcccc    420
aagaacgtga cagatgagca ggagggttc gccgagggct tcgtgcgcgc cctggccgaa    480
```